(12) United States Patent
Corti et al.

(10) Patent No.: US 7,795,386 B2
(45) Date of Patent: Sep. 14, 2010

(54) PEPTIDES COMPRISING AN ISODGR MOTIF

(75) Inventors: Angelo Corti, Azzano San Paolo (IT); Flavio Curnis, Alzano Lombardo (IT)

(73) Assignees: Molmed SpA, Milan (IT); Fondazione Centro San Raffaele del Monte Tabor, Milan (IT)

( * ) Notice: Subject to any disclaimer, the term of this patent is extended or adjusted under 35 U.S.C. 154(b) by 0 days.

(21) Appl. No.: 11/793,417

(22) PCT Filed: Dec. 21, 2005

(86) PCT No.: PCT/IB2005/004058
§ 371 (c)(1), (2), (4) Date: Nov. 8, 2007

(87) PCT Pub. No.: WO2006/067633
PCT Pub. Date: Jun. 29, 2006

(65) Prior Publication Data
US 2009/0068106 A1 Mar. 12, 2009

Related U.S. Application Data

(60) Provisional application No. 60/638,158, filed on Dec. 23, 2004.

(51) Int. Cl.
| C07K 5/00 | (2006.01) |
| C07K 7/00 | (2006.01) |
| C07K 16/00 | (2006.01) |
| C07K 17/00 | (2006.01) |
| C07K 14/00 | (2006.01) |
| A61K 38/12 | (2006.01) |
| A61K 38/00 | (2006.01) |
| A61K 38/04 | (2006.01) |
| A61K 45/00 | (2006.01) |

(52) U.S. Cl. ............... 530/317; 424/85.1; 424/85.2; 514/18; 530/326; 530/327; 530/328; 530/329; 530/350; 530/402

(58) Field of Classification Search ............ None
See application file for complete search history.

(56) References Cited

U.S. PATENT DOCUMENTS

| 5,091,176 A | 2/1992 | Braatz et al. |
| 5,196,511 A | 3/1993 | Plow et al. |
| 5,214,131 A | 5/1993 | Sano et al. |
| 5,262,520 A | 11/1993 | Plow et al. |
| 5,536,814 A | 7/1996 | Ruoslahti et al. |
| 5,580,853 A | 12/1996 | Sytkowski |
| 5,753,230 A | 5/1998 | Brooks et al. |
| 5,811,512 A | 9/1998 | Hirschmann et al. |
| 5,891,418 A | 4/1999 | Sharma |
| 5,912,234 A | 6/1999 | Ruoslahti et al. |
| 6,177,542 B1 | 1/2001 | Ruoslahti et al. |
| 6,825,167 B1 | 11/2004 | Yokoyama et al. |
| 2002/0103130 A1 | 8/2002 | Ruoslahti et al. |
| 2003/0165825 A1 | 9/2003 | Balint et al. |
| 2004/0071689 A1 | 4/2004 | Ruoslahti et al. |
| 2004/0077828 A1 | 4/2004 | Rubin et al. |

FOREIGN PATENT DOCUMENTS

| EP | 0 089 676 A2 | 9/1983 |
| EP | 0 110 044 A1 | 6/1984 |
| EP | 0 077 670 B1 | 6/1989 |
| EP | 0 987 275 B1 | 1/2008 |
| WO | WO 95/14714 | 6/1995 |
| WO | WO 95/25543 | 9/1995 |
| WO | WO 97/10507 | 3/1997 |
| WO | WO 98/10795 | 3/1998 |
| WO | WO 00/67771 | 11/2000 |
| WO | WO 01/61017 A2 | 8/2001 |
| WO | WO 02/47537 A2 | 6/2002 |
| WO | WO 02/055547 | 7/2002 |
| WO | WO 02/085405 A2 | 10/2002 |
| WO | WO 03/009881 A2 | 2/2003 |
| WO | WO 03/092737 A1 | 11/2003 |
| WO | WO 03/093478 A1 | 11/2003 |

OTHER PUBLICATIONS

Wermuth et al., "Stereoisomerism and Biological Activity of the Selective and Superactive $a_v\beta_3$ Integrin Inhibitor cyclo(-RGDfV-) and Its Retro-Inverso Peptide," *J. Am. Chem. Soc.* 1997, 119, pp. 1328-1335.

Yamada et al., "Peptide Inhibitors of Fibronectin, Laminin, and Other Adhesion Molecules: Unique and Shared Features," *Journ. Of Cell. Phys.*, 1987, pp. 21-28.

Rusnati et al., "$a_v\beta_3$ Integrin Mediates the Cell-adhesive Capacity and Biological Activity of Basic Fibroblast Growth Factor (FGF-2) in Cultured Endothelial Cells," *Molecular Biology of the Cell*, vol. 8, 1997, pp. 2449-2461.

Fuzery et al., "Solution State Conformation and Degradation of Cyclopeptides Containing an NGR Motif," *Journ. Of Peptide Science*, 2005, pp. 53-59.

Colombo et al., "Structure-Activity Relationships of Linear and Cyclic Peptides Containing the NGR Tumor-homing Motif," *The Journ. Of Biological Chemistry*, vol. 277, No. 49, 2002, pp. 47891-47897.

Curnis et al., Differential Binding of Drugs Containing the NGR Motif to CD13 Isoforms in Tumor Vessels, Epithelia, and Myeloid Cells, 2002, pp. 867-874.

Curnis et al., "Targeted Deliver of IFN γ to Tumor Vessels Uncouples Antitumor from Counterregulatory Mechanisms," *Cancer Res.*, vol. 65, No. 7, pp. 2906-2913 (2005).

Curnis et al., "Spontaneous Formation of L-Isoaspartate and Gain of Function in Fibronectin," *J. Biol. Chem.*, vol. 281, No. 47, pp. 36466-36476 (2006).

Aswad, D. W. (1984). Stoichiometric methylation of porcine adrenocorticotropin by protein carboxyl methyltransferase requires deamidation of asparagine 25. Evidence for methylation at the alpha-carboxyl group of atypical L-isoaspartyl residues. J Biol. Chem., 259, pp. 10714-10721.

(Continued)

*Primary Examiner*—Robert Landsman
(74) *Attorney, Agent, or Firm*—Foley & Lardner LLP

(57) ABSTRACT

Disclosed herein are peptides which include an isoDGR motif and which selectively inhibit αvβ3 integrin. In some embodiments, the isoDGR motif results from the deamidation of an NGR motif.

40 Claims, 14 Drawing Sheets

OTHER PUBLICATIONS

Blood et al., (1990) "Tumor interactions with the vasculature: angiogenesis and tumor metastasis," Bioch. Biophys. Acta, 1032:89-118.

Boehm, U., T. Klamp, M. Groot, and J.C. Howard. (1997) Cellular responses to interferon-gamma. Annu. Rev. Immunol. 15:749-795.

Borgia and Fields, "Chemical Synthesis of Proteins," (2000) TibTech 18: 243-251.

Brooks, P. C, Montgomery, A. M., Rosenfeld, M., Reisfeld, R. A., Hu, T., Klier, G., and Cheresh, D. A. (1994). Integrin alpha v beta 3 antagonists promote tumor regression by inducing apoptosis of angiogenic blood vessels. Cell 79, 1157-1164. [Abstract Only].

Brooks, P. C, Stromblad, S., Klemke, R., Visscher, D., Sarkar, F. H., and Cheresh, D. A. (1995). Antiintegrin alpha v beta 3 blocks human breast cancer growth and angiogenesis in human skin. J Clin Invest 96, 1815-1822.

Busk, M., Pytela, R., and Sheppard, D. (1992). Characterization of the integrin alpha v beta 6 as a fibronectin-binding protein. J Biol Chem 267, 5790-5796.

Carswell, E. A., et al., (1975) An endotoxin-induced serum factor that causes necrosis of tumors. Proc. Natl. Acad. Sci. USA. 72:3666-70.

Colombo, P., et al., (1993) Immunoscintigraphy with anti-chromogranin A antibodies in patients with endocrine/neuroendocrine tumors. J. Endocr. Invest. 16:841-3.

Corti, A., Poiesi, C, Merli, S., and Cassani, G. (1994). Tumor necrosis factor (TNF) alpha quantification by ELISA and bioassay: effects of TNF alpha-soluble TNF receptor (p55) complex dissociation during assay incubations. Journal of Immunological Methods 777, 191-198.

Corti, A., et al., (1998) Tumor targeting with biotinylated tumor necrosis factor alpha: Structure activity relationships and mechanism of action on avidin pretargeted tumor cells. Cancer Res. 58:3866-3872.

Curnis, F., Sacchi, A., Borgna, L., Magni, F., Gasparri, A., and Corti, A. (2000). Enhancement of tumor necrosis factor alpha antitumor immunotherapeutic properties by targeted delivery to aminopeptidase N (CD 13). Nature Biotechnology 18, 1185-1190.

Debs, R. J., et al., (1989) Liposome-associated tumor necrosis factor retains bioactivity in the presence of neutralizing anti-tumor necrosis factor antibodies. J. Immunol. 143:1192-7.

Debs, R. J., et al., Immunomodulatory and toxic effects of free and liposome-encapsulated tumor necrosis factor alpha in rats. Cancer Res. 1990. 50:375-80.

Dedhar, S., and Gray, V. (1990). Isolation of a novel integrin receptor mediating Arg- Gly-Asp-directed cell adhesion to fibronectin and type I collagen from human neuroblastoma cells. Association of a novel beta 1-related subunit with alpha v. J Cell Biol 110, 2185-2193.

Devos et al., "Molecular Cloning of Human Immune Interferon cDNA and its Expression in Eukaryotic Cells," (1982) Nucleic Acids Res. 10:2487-2501.

Di Matteo, P., Curnis, F., Longhi, R., Colombo, G., Sacchi, A., Crippa, L., Protti, M. P., Ponzoni, M., Toma, S., and A., C. Immunogenic and structural properties of the Asn-Gly-Arg (NGR) tumor neovasculature-homing motif. Molecular Immunology pp. 1509-1518, 2006.

Ealick et al., "Three-Dimensional Structure of Recombinant Human Interferon-γ," (1991) Science 252:698-702.

Eggermont, A. M., et al., (1996) Isolated limb perfusion with tumor necrosis factor and melphalan for limb salvage in 186 patients with locally advanced soft tissue extremity sarcomas. The cumulative multicenter European experience. Ann. Surg. 224:756-65.

Farrar, M. A., and R.D. Schreiber. (1993). The molecular cell biology of interferon- gamma and its receptor. Annu. Rev. Immunol. 11:571-611.

Fraker, D.L., Alexander, H.R. & Pass, H.I., (1995). Biologic therapy with TNF: systemic administration and isolation-perfusion. In Biologic therapy of cancer: principles and practice, De Vita, V., Hellman, S. & Rosenberg, S. (eds) pp. 329-345. J.B. Lippincott Company: Philadelphia.

Fiers, W. Biologic therapy with TNF: preclinical studies. In V. De Vita, S. Hellman, and S. Rosenberg Eds. Biologic therapy of cancer: principles and practice. J.B. Lippincott Company, Philadelphia, 1995. p. 295-327.

Friedlander, M., Brooks, P. C, Shaffer, R. W., Kincaid, C. M., Varner, J. A., and Cheresh, D. A. (1995). Definition of two angiogenic pathways by distinct alpha v integrals. Science 270, 1500-1502.

Friedlander, M., Theesfeld, C. L., Sugita, M., Fruttiger, M., Thomas, M. A., Chang, S., and Cheresh, D. A. (1996). Involvement of integrins alpha v beta 3 and alpha v beta 5 in ocular neovascular diseases. Proc Natl Acad Sci U S A 93, 9764-9769.

Galletti, P., Ingrosso, D., Manna, C, Sica, F., Capasso, S., Pucci, P., and Marino, G. (1988). Enzymatic methyl esterification of synthetic tripeptides: structural requirements of the peptide substrate. Detection of the reaction products by fast-atom-bombardment mass spectrometry. Eur J Biochem 177, 233-239.

Gardner, J. M., and Hynes, R. 0. (1985). Interaction of fibronectin with its receptor on platelets. Cell 42, 439-448.

Gasparri, A., Moro, M., Curnis, F., Sacchi, A., Pagano, S., Veglia, F., Casorati, G., Siccardi, A. G., Dellabona, P., and Corti, A. (1999). Tumor pretargeting with avidin improves the therapeutic index of biotinylated tumor necrosis factor alpha in mouse models. Cancer Research 59, 2917-2923.

Gately et al., "The Interleukin-12/ Interleukin-12-Receptor System: Role in Normal and Pathologic Immune Responses," (1998) Ann. Rev. Immunol. 16:495-521.

Geiger, T., and Clarke, S. (1987). Deamidation, isomerization, and racemization at asparaginyl and aspartyl residues in peptides. Succinimide-linked reactions that contribute to protein degradation. J Biol Chem 262, 785-794.

Gray et al., "Structure of the Human Immunie Interferon Gene," Nature 298:859-863, 1982.

Hammes, H. P., Brownlee, M., Jonczyk, A., Sutter, A., and Preissner, K. T. (1996). Subcutaneous injection of a cyclic peptide antagonist of vitronectin receptor-type integrins inhibits retinal neovascularization. Nat Med 2, 529-533.

Helson, L., et al., Effect of tumor necrosis factor on cultured human melanoma cells. Nature 1975. 258:731-732.

Hill, S., et al., Low-dose tumour necrosis factor alpha and melphalan in hyperthermic isolated limb perfusion. Br. J. Sugr. 1993. 80:995-7.

Hocking, D. C, Sottile, J., and McKeown-Longo, P. J. (1998). Activation of distinct alpha5betal-mediated signaling pathways by fibronectin's cell adhesion and matrix assembly domains. J Cell Biol 141, 241-253.

Humphries, M. J., Obara, M., Olden, K., and Yamada, K. M. (1989). Role of fibronectin in adhesion, migration, and metastasis. Cancer Invest 7, 373-393.

Hynes, R. O. (2002). A revaluation of integrins as regulators of angiogenesis. Nat Med 5, 918-921.

Johansson, S., Svineng, G., Wennerberg, K., Armulik, A., and Lohikangas, L. (1997). Fibronectin-integrin interactions. Front Biosci 2, d 126-146.

Kobayashi, et al., Identification and Purification of Natural Killer Cell Stimulatory Factor (NKSF), a Cytokine with Multiple Biologic Effects of Human Lymphocytes, (1989) J:Exp Med. 170:827-845.

Koivunen, E., Gay, D. A., and Ruoslahti, E. (1993). Selection of peptides binding to the alpha 5 beta 1 integrin from phage display library. Journal of Biological Chemistry 268, 20205-20210.

Lanthier, J., and Desrosiers, R. R. (2004). Protein L-isoaspartyl methyltransferase repairs abnormal aspartyl residues accumulated in vivo in type-I collagen and restores cell migration. Exp Cell Res 293, 96-105.

Lienard, D., et al., In transit metastases of malignant melanoma treated by high dose rTNF alpha in combination with interferon-gamma and melphalan in isolation perfusion. World Journal of Surgery 1992. 16:234-40.

Ling, et al., "Human II-12 p40 Homodimer Binds to the IL-12 Receptor but does not Mediate Biologic Activity," (1995) J. Exp Med. 154:116-127.

Ljunggren, H. G., and Karre, K. (1985). Host resistance directed selectively against H-2-deficient lymphoma variants. Analysis of the mechanism. Journal of Experimental Medicine 162, 1745-1759.

Loetscher, H., et al., Human tumor necrosis factor alpha (TNF alpha) mutants with exclusive specificity for the 55-kDa or 75kDa TNF receptors. J. Biol. Chem. 1993. 268:26350-7.

Lowenson, J. D., and Clarke, S. (1992). Recognition of D-aspartyl residues in polypeptides by the erythrocyte L-isoaspartyl/D-aspartyl protein methyltransferase. Implications for the repair hypothesis. J Biol Chem 267, 5985-5995.

McFadden, P. N., and Clarke, S. (1987). Conversion of isoaspartyl peptides to normal peptides: implications for the cellular repair of damaged proteins. Proc Natl Acad Sci U S A W, 2595-2599.

Modorati, G., et al., Immunoscintigraphy with three step monoclonal pretargeting technique in diagnosis of uveal melanoma: preliminary results. Br. J. Ophtalm. 1994. 78:19-23.

Mohri, H. (1997). Interaction of fibronectin with integrin receptors: evidence by use of synthetic peptides. Peptides 18, 899-907.

Moro, M., et al., Tumor cell targeting with antibody-avidin complexes and biotinylated tumor necrosis factor alpha. Cancer Res. 1997. 57:1922-8.

Moyano, J. V., Carnemolla, B., Dominguez-Jimenez, C, Garcia-Gila, M., Albar, J. P., Sanchez-Aparicio, P., Leprini, A., Querze, G., Zardi, L., and Garcia-Pardo, A. (1997). Fibronectin type III5 repeat contains a novel cell adhesion sequence, KLDAPT, which binds activated alpha4beta1 and alpha4beta7 integrins. J Biol Chem 272, 24832-24836.

Murray, E. D., Jr., and Clarke, S. (1984). Synthetic peptide substrates for the erythrocyte protein carboxyl methyltransferase. Detection of a new site of methylation at isomerized L-aspartyl residues. J Biol Chem 259, 10722-10732.

Pankov, R., and Yamada, K. M. (2002). Fibronectin at a glance. J Cell Sci 115, 3861-3863.

Paganelli, G., et al., Clinical application of the avidin-biotin system for tumor targeting. In D. Goldenberg Ed. Cancer therapy with radiolabeled antibodies. CRC Press, Boca Raton, 1995. p. 239-253.

Pennica, D., et al., (1984). Human tumor necrosis factor: precursor, structure, expression and homology to lymphotoxin. Nature, 321, 724-729.

Plow, E. F., Haas, T. A., Zhang, L., Loftus, J., and Smith, J. W. (2000). Ligand binding to integrins. J Biol Chem 275, 21785-21788.

Plow, E. F., McEver, R. P., Coller, B. S., Woods, V. L., Jr., Marguerie, G. A., and Ginsberg, M. H. (1985). Related binding mechanisms for fibrinogen, fibronectin, von Willebrand factor, and thrombospondin on thrombin-stimulated human platelets. Blood 66, 724-727.

Podlaski, et al., "Molecular Characterization of Interleukin 12," (1992) Arch. Biochem. Biophys. 294:230-237.

Pytela, R., Pierschbacher, M. D., and Ruoslahti, E. (1985). Identification and isolation of a 140 kd cell surface glycoprotein with properties expected of a fibronectin receptor. Cell 40, 191-198.

Rathjen, D. A., et al., (1992). Selective enhancement of the tumour necrotic activity of TNF alpha with monoclonal antibody. Brit. J. Cancer 65:852.

Reissner, K. J., and Aswad, D. W. (2003). Deamidation and isoaspartate formation in proteins: unwanted alterations or surreptitious signals? Cell Mol Life Sci 60, 1281-1295.

Rinderknecht et al., "Natural Human Interferon-γ, Complete Amino Acid Sequence and Determination of Sites of Glycosylation," (J. Biol. Chem.), 259:6790-6797, 1984.

Robert, B., et al., 1996. Cytokine targeting in tumors using a bispecific antibody directed against carcinoembryonic antigen and tumor necrosis factor alpha. Cancer Res. 56:4758.

Robinson, A. B., McKerrow, J. H., and Gary, P. (1970). Controlled deamidation of peptides and proteins: an experimental hazard and a possible biological timer. Proc Natl Acad Sci U S A 66, 753-757.

Robinson, N. E., and Robinson, A. B. (2001). Molecular clocks. Proc Natl Acad Sci U S A 98, 944-949.

Robinson, N. E., Robinson, Z. W., Robinson, B. R., Robinson, A. L., Robinson, J. A., Robinson, M. L., and Robinson, A. B. (2004). Structure-dependent nonenzymatic deamidation of glutaminyl and asparaginyl pentapeptides. J Pept Res 63, 426-436.

Schraffordt Koops, et al., (1998) Hyperthermic isolated limb perfusion with tumour necrosis factor and melphalan as treatment of locally advanced or recurrent soft tissue sarcomas of the extremities. Radiothepray & Oncology. 48:1-4.

Seder, et al., "Interleukin 12 acts directly on CD4+ T cells to enhance priming for interfereon γ production and diminishes interleukin 4 inhibition of such priming," (1993) Proc. Natl. Acad. Sci. 90:10188-10192.

Smith, J. W., Vestal, D. J., Irwin, S. V., Burke, T. A., and Cheresh, D. A. (1990). Purification and functional characterization of integrin alpha v beta 5. An adhesion receptor for vitronectin. J Biol Chem 265, 11008-11013.

Stephenson, R. C, and Clarke, S. (1989). Succinimide formation from aspartyl and asparaginyl peptides as a model for the spontaneous degradation of proteins. J Biol Chem 264, 6164-6170.

Takada, Y., Huang, C, and Hemler, M. E. (1987). Fibronectin receptor structures in the VLA family of heterodimers. Nature 326, 607-609.

Tanzarella, S., Russo, V., Lionello, I., Dalerba, P., Rigatti, D., Bordignon, C, and Traversari, C. (1999). Identification of a promiscuous T-cell epitope encoded by multiple members of the MAGE family. Cancer Res 59, 2668-2674.

Taya et al., Cloning and structure of the human immune interferon-γ chromosomal gene, (1982) EMBO J. 1:953-958.

Tracey, K. J., and A. Cerami. (1993) Tumor necrosis factor, other cytokines and disease. Ann. Rev. Cell Biol, 9:317-43.

Tyler-Cross, R., and Schirch, V. (1991). Effects of amino acid sequence, buffers, and ionic strength on the rate and mechanism of deamidation of asparagine residues in small peptides. J Biol Chem 266, 22549-22556.

Van Ostade, X., et al., (1993) Human TNF mutants with selective activity on the p55 receptor. Nature. 361:266-9.

Vogel, B. E., Tarone, G, Giancotti, F. G., Gailit, J., and Ruoslahti, E. (1990). A novel fibronectin receptor with an unexpected subunit composition (alpha v beta 1). J Biol Chem 265, 5934-5937.

Weber, D. J., and McFadden, P. N. (1997b). Injury-induced enzymatic methylation of aging collagen in the extracellular matrix of blood vessels. J Protein Chem 16, 269-281.

Weinacker, A., Chen, A., Agrez, M., Cone, R. L, Nishimura, S., Wayner, E., Pytela, R., and Sheppard, D. (1994). Role of the integrin alpha v beta 6 in cell attachment to fibronectin. Heterologous expression of intact and secreted forms of the receptor. J Biol Chem 269, 6940-6948.

Wood and Wetzel, "Novel cyclization chemistry especially suited for biologically derived, unprotected peptides," (1992) Int'l J. Peptide Protein Res. 39: 533-39.

Yamada, K. M. (1989). Fibronectins: structure, functions and receptors. Curr Opin Cell Biol 1, 956-963.

Yang, J., et al., (1995) A genetically engineered single-chain FV/TNF molecule possesses the anti-tumor immunoreactivity of FV as well as the cytotoxic activity of tumor necrosis factor. Mol. Immunol. 32:873-81.

A

Asparagine → Succinimide Intermediate

B

Degradation of Succinimide Intermediate

Aspartic Acid

IsoAspartic Acid

SEQUENCE LISTING

```
<160> NUMBER OF SEQ ID NOS: 72

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu, Val, Ala, Cys, Gly, Tyr, Pro, His, Lys,
      Gln or Ile
<220> FEATURE:
<221> NAME/KEY: MOD_RES
<222> LOCATION: (5)..(5)
<223> OTHER INFORMATION: Cys, Gly, His, Leu, Glu, Thr, Gln, Arg, Ser or
      Pro

<400> SEQUENCE: 1

Xaa Asn Gly Arg Xaa
1               5
```

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Asn Gly Arg Cys Val Ser Gly Cys Ala Gly Arg Cys
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Gly Arg Ala His Ala
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Asn Gly Arg Gly
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Val Leu Asn Gly Arg Met Glu Cys
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Asn Gly Arg Cys
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 7

Cys Asn Gly Arg Cys Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Asn Gly Arg Glu
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Tyr Asn Gly Arg Thr
1               5

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Gln Cys Ile Cys Thr Gly Asn Gly Arg Gly Glu Trp Lys Cys Glu
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Gln Cys Ile Ser Thr Gly Asn Gly Arg Gly Glu Trp Lys Cys Glu
1               5                   10                  15

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Ile Cys Thr Gly Asn Gly Arg Gly Glu Trp Lys Cys
1               5                   10

<210> SEQ ID NO 13
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 13

Cys Ile Ser Thr Gly Asn Gly Arg Gly Glu Trp Lys Cys
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Arg Cys Thr Cys Val Gly Asn Gly Arg Gly Glu Trp Thr Cys Tyr
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Met Arg Cys Thr Ser Val Gly Asn Gly Arg Gly Glu Trp Thr Cys Tyr
1               5                   10                  15

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Thr Cys Val Gly Asn Gly Arg Gly Glu Trp Thr Cys
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Thr Ser Val Gly Asn Gly Arg Gly Glu Trp Thr Cys
1               5                   10

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu, Val, Ala, Cys, Gly, Tyr, Pro, His, Lys,
      Gln or Ile
```

-continued

```
<220> FEATURE:
<221> NAME/KEY: MOD_RES
<222> LOCATION: (5)..(5)
<223> OTHER INFORMATION: Cys, Gly, His, Leu, Glu, Thr, Gln, Arg, Ser or
      Pro

<400> SEQUENCE: 18

Xaa Asp Gly Arg Xaa
1               5

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys Asp Gly Arg Cys Val Ser Gly Cys Ala Gly Arg Cys
1               5                   10

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Gly Arg Ala His Ala
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Asp Gly Arg Gly
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Cys Val Leu Asp Gly Arg Met Glu Cys
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Cys Asp Gly Arg Cys
```

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Cys Asp Gly Arg Cys Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Asp Gly Arg Glu
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Tyr Asp Gly Arg Thr
1               5

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Leu Gln Cys Ile Cys Thr Gly Asp Gly Arg Gly Glu Trp Lys Cys Glu
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Leu Gln Cys Ile Ser Thr Gly Asp Gly Arg Gly Glu Trp Lys Cys Glu
1               5                   10                  15

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 29

Cys Ile Cys Thr Gly Asp Gly Arg Gly Glu Trp Lys Cys
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Ile Ser Thr Gly Asp Gly Arg Gly Glu Trp Lys Cys
1               5                   10

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Met Arg Cys Thr Cys Val Gly Asp Gly Arg Gly Glu Trp Thr Cys Tyr
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Met Arg Cys Thr Ser Val Gly Asp Gly Arg Gly Glu Trp Thr Cys Tyr
1               5                   10                  15

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Cys Thr Cys Val Gly Asp Gly Arg Gly Glu Trp Thr Cys
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Cys Thr Ser Val Gly Asp Gly Arg Gly Glu Trp Thr Cys
1               5                   10

<210> SEQ ID NO 35

```
<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly Gly Gly
1

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Cys Ala Arg Ala Cys
1               5

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ctggatccga aagtgttttt gatcatgctg ctggg                               35

<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tatattaagc tttcagtgcc tctcacactt cc                                  32

<210> SEQ ID NO 39
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tatattaagc tttcagtgcc tctcacactt ccactctcca ctgccgctg                49

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
caccatgggc aacggccgtg gcggcgtc                                       28
```

<210> SEQ ID NO 41
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tcaggatcct cacagggcaa tgatcccaaa gtagac                          36

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Cys Asn Gly Arg Cys Gly Val Arg Tyr
1               5

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
caccatgtgc gacggccgtt gcggc                                     25

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ctggatcctc acagagcaat gatcccaaag                                30

<210> SEQ ID NO 45
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Arg Cys Asn Asp Gln Asp Thr Arg Thr Ser Tyr Arg Ile Gly Asp
1               5                   10                  15

Thr Trp Ser Lys Lys Glu Asn Arg Gly Asn Leu Leu Gln Cys Ile Cys
            20                  25                  30

Thr Gly Asn Gly Arg Gly Glu Trp Lys Cys Glu Arg His Thr
        35                  40                  45

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic -continued peptide
<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Gln Cys Ile Ser Thr Gly Asn Gly Arg Gly Glu Trp Lys Cys Glu
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Gln Cys Ile Ser Thr Arg Gly Gly Asn Gly Glu Trp Lys Cys Glu
1               5                   10                  15

<210> SEQ ID NO 48
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Glu Ile Cys Thr Thr Asn Glu Gly Val Met Tyr Arg Ile Gly Asp Gln
1               5                   10                  15

Trp Asp Lys Gln His Asp Met Gly His Met Met Arg Cys Thr Cys Val
                20                  25                  30

Gly Asn Gly Arg Gly Glu Trp Thr Cys Tyr Ala Tyr
            35                  40

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Met Arg Cys Thr Cys Val Gly Asn Gly Arg Gly Glu Trp Thr Cys Tyr
1               5                   10                  15

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Gly Gly Asn Gly
1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

```
Pro His Ser Arg Asn
1               5

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Glu Asp Val
1

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Lys Leu Asp Ala Pro Thr
1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu, Val, Ala, Cys, Gly, Tyr, Pro, His, Lys,
      Gln or Ile
<220> FEATURE:
<221> NAME/KEY: MOD_RES
<222> LOCATION: (2)..(2)
<223> OTHER INFORMATION: Iso-Asp
<220> FEATURE:
<221> NAME/KEY: MOD_RES
<222> LOCATION: (5)..(5)
<223> OTHER INFORMATION: Cys, Gly, His, Leu, Glu, Thr, Gln, Arg, Ser or
      Pro

<400> SEQUENCE: 54

Xaa Asp Gly Arg Xaa
1               5

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Iso-Asp

<400> SEQUENCE: 55

Cys Asp Gly Arg Cys Val Ser Gly Cys Ala Gly Arg Cys
1               5                   10
```

```
<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Iso-Asp

<400> SEQUENCE: 56

Asp Gly Arg Ala His Ala
1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Iso-Asp

<400> SEQUENCE: 57

Gly Asp Gly Arg Gly
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Iso-Asp

<400> SEQUENCE: 58

Cys Val Leu Asp Gly Arg Met Glu Cys
1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Iso-Asp

<400> SEQUENCE: 59

Cys Asp Gly Arg Cys
1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: Iso-Asp

<400> SEQUENCE: 60

Cys Asp Gly Arg Cys Gly
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Iso-Asp

<400> SEQUENCE: 61

Leu Asp Gly Arg Glu
1               5

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Iso-Asp

<400> SEQUENCE: 62

Tyr Asp Gly Arg Thr
1               5

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Iso-Asp

<400> SEQUENCE: 63

Leu Gln Cys Ile Cys Thr Gly Asp Gly Arg Gly Glu Trp Lys Cys Glu
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Iso-Asp

<400> SEQUENCE: 64
```

```
Leu Gln Cys Ile Ser Thr Gly Asp Gly Arg Gly Glu Trp Lys Cys Glu
1               5                   10                  15
```

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Iso-Asp

<400> SEQUENCE: 65

```
Cys Ile Cys Thr Gly Asp Gly Arg Gly Glu Trp Lys Cys
1               5                   10
```

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Iso-Asp

<400> SEQUENCE: 66

```
Cys Ile Ser Thr Gly Asp Gly Arg Gly Glu Trp Lys Cys
1               5                   10
```

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Iso-Asp

<400> SEQUENCE: 67

```
Met Arg Cys Thr Cys Val Gly Asp Gly Arg Gly Glu Trp Thr Cys Tyr
1               5                   10                  15
```

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Iso-Asp

<400> SEQUENCE: 68

```
Met Arg Cys Thr Ser Val Gly Asp Gly Arg Gly Glu Trp Thr Cys Tyr
1               5                   10                  15
```

<210> SEQ ID NO 69
<211> LENGTH: 13
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Iso-Asp

<400> SEQUENCE: 69

Cys Thr Cys Val Gly Asp Gly Arg Gly Glu Trp Thr Cys
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Iso-Asp

<400> SEQUENCE: 70

Cys Thr Ser Val Gly Asp Gly Arg Gly Glu Trp Thr Cys
1               5                   10

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Cys Ala Arg Ala Cys Gly
1               5

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Val Arg Tyr
1
```

PEPTIDES COMPRISING AN ISODGR MOTIF

CROSS REFERENCE TO RELATED APPLICATIONS

This application is the National Phase of PCT/IB2005/004058, filed Dec. 21, 2005, and published as WO 2006/067633, and claims priority to U.S. Provisional Application No. 60/638,158, filed Dec. 23, 2004. The entirety of these applications are incorporated herein by reference.

FIELD OF THE INVENTION

The present invention relates to novel peptides which may be used in the treatment of diseases associated with angiogenesis and cancer. More particularly, the invention relates to extracellular matrix peptides and derivatives thereof, and, in particular to peptides comprising a DGR motif and isomers thereof. The present invention also relates to modified cytokines, in particular to cytokine derivatives capable of "homing" angiogenic vessels.

BACKGROUND TO THE INVENTION

The extracellular matrix is an important regulator of cell and tissue behaviour. Proteins of the extracellular matrix, such as fibronectin, vitronectin, collagens and laminin bind to a number of cell receptors that control many medically important biological phenomena, such as angiogenisis, cell migration, tissue repair, cancer cell differentiation, platelet aggregation and homing of immune system cells and neuronal processes to target sites. An important family of receptors that bind to the extracellular matrix are the integrins.

Fibronectins are large extracellular matrix glycoproteins (~450 KDa) that have been implicated in integrin binding. They are composed of two nearly identical disulfide bonded subunits, each subunit consisting of three types of repeating homologous modules termed FN-I, FN-II and FN-III repeats. In addition, alternatively spliced modules, called EDA, EDB and IIICS, can also be present (Mohri, 1997; Pankov and Yamada, 2002). Single modules or groups of modules may contain binding sites for different molecules, including sulfated glycosaminoglycans, DNA, gelatin, heparin and fibrin (Mohri, 1997; Pankov and Yamada, 2002; Yamada, 1989). Furthermore, fibronectins contains binding sites for about half of the known cell surface integrin receptors (Johansson et al., 1997; Plow et al., 2000). In particular, the FN-III$_{10}$ repeat contains an RGD site that can bind $\alpha_3\beta_1$, $\alpha_5\beta_1$, $\alpha_v\beta_3$, $\alpha_v\beta_5$, $\alpha_v\beta_6$, $\alpha_8\beta_1$ and $\alpha II_b\beta_3$ integrins, while the FN-II$_9$ repeat contains the so-called "synergy site" PHSRN (SEQ ID NO: 51) that cooperates with RGD in the binding of $\alpha_5\beta_1$ and $aII_b\beta_3$ (Busk et al., 1992; Dedhar and Gray, 1990; Gardner and Hynes, 1985; Johansson et al., 1997; Pankov and Yamada, 2002; Plow et al., 1985; Pytela et al., 1985; Smith et al., 1990; Takada et al., 1987; Vogel et al., 1990; Weinacker et al., 1994). The FN-III$_{14}$-IIICS region contains three sites (called CS$_1$, CS$_5$ and H$_1$) characterised by the presence of LDV motif and accessory REDV (SEQ ID NO: 52) and IDA sites involved in $\alpha_4\beta_1$, and $\alpha_4\beta_7$ recognition (Johansson et al., 1997; Pankov and Yamada, 2002). Moreover, the FN-III$_5$ repeat contains the KLDAPT (SEQ ID NO: 53) sequence that bind $\alpha_4\beta_1$ and $\alpha_4\beta_7$ (Moyano et al., 1997) whereas FN-I$_{19}$ and FN-II$_{1-2}$ contain sites, not yet identified, that can interact with $\alpha_5\beta_1$ (Hocking et al., 1998).

Primary and tertiary structure analysis of human fibronectin, showed that this protein contains two GNGRG (SEQ ID NO: 4) loops, located in FN-I$_5$ and FN-I$_7$ modules, that are conserved in bovine, murine, rat, amphibian and fish (Di Matteo et al.). Two additional NGR sites, less conserved, are also present in human FN-II$_1$ and FN-III$_9$. Recent experimental work showed that peptides containing the NGR motif can inhibit $\alpha_5\beta_1$ and $\alpha_v\beta_1$-mediated cell adhesion to fibronectin (Koivunen et al., 1993).

The interaction between cell surface anchored integrins and extracellular matrix components have been implicated in angiogenesis, an important process in neonatal growth and in the pathogenesis of a large variety of clinical diseases including tissue inflammation, arthritis, tumor growth, diabetic retinopathy, macular degeneration by neovascularization of retina and the like conditions. It is known that $\alpha_v\beta_3$ integrin, the vitronectin receptor, plays a critical role in angiogenesis (Hynes, 2002). Compounds able to inhibit the interaction of this integrin with extracellular matrix proteins are known to inhibit angiogenesis and tumor growth (Brooks et al., 1994; Brooks et al., 1995; Friedlander et al., 1995; Friedlander et al., 1996; Hammes et al., 1996). However, a problem associated with these inhibitors is their cross-reactivity with many integrin species.

In the light of increasing awareness of the role of the extracellular matrix in biological processes and disease development, there remains a need for novel therapeutics that target this area. The present invention addresses this need.

The antitumoral activity of some cytokines is well known and described. Some cytokines have already been used therapeutically also in humans (Fiers et al., 1995). For example, such cytokines as interleukine-2 (IL-2) and interferon $\alpha$ (IFN$\alpha$) have shown positive antitumoral activity in patients with different types of tumors, such as kidney metastatic carcinoma, hairy cell leukemia, Kaposi sarcoma, melanoma, multiple mieloma, and the like. Other cytokines like IFN$\beta$, the Tumor Necrosis Factor (TNF) $\alpha$, TNF$\beta$, IL-1, 4, 6, 12, 15 and the Colony Stimulating Factors (CFSs) have shown a certain antitumoral activity on some types of tumors and therefore are the object of further studies.

In general, the therapeutic use of cytokines is strongly limited by their systemic toxicity. TNF, for example, was originally discovered for its capacity of inducing the hemorrhagic necrosis of some tumors Carswell et al., 1975), and for its in vitro cytotoxic effect on different tumoral lines Helson et al., 1975), but it subsequently proved to have strong pro-inflammatory activity, which can, in case of overproduction conditions, dangerously affect the human body (Tracey et al., 1993).

As the systemic toxicity is a fundamental problem with the use of pharmacologically active amounts of cytokines in humans, novel derivatives and therapeutic strategies are now under evaluation, aimed at reducing the toxic effects of this class of biological effectors while keeping their therapeutic efficacy. For example, WO01/61017 discloses a conjugation product between TNF or IFN$\gamma$ and a ligand of the CD13 receptor; WO03/093478 discloses a pharmaceutical composition comprising a conjugate of a cytokine and a tumor targeting moiety wherein the cytokine is present in an amount which does not induce a negative feedback mechanism; and WO03/092737 discloses conjugates of various cytokines and tumor targeting moieties. The present invention provides novel cytokine conjugates that have therapeutic potential.

SUMMARY OF THE INVENTION

Asparagine (N) deamidation, a non-enzymatic protein post-translational modification, is generally viewed as a deleterious event associated with protein ageing. In the present application we show that an Asparagine-Glycine-Arginine (NGR) sequence of the extracellular matrix can promote endothelial cell adhesion via an unusual mechanism based on non-enzymatic deamidation of asparagine to aspartic acid and isoaspartic acid, generating a new cell adhesion motif. In particular, we show that this deamidation is associated with a "gain of function"; deamidated fragments being able to inhibit endothelial cell adhesion to vitronectin, inhibit αvβ3 integrin and inhibit tumor growth.

In particular, we have shown that the $_L$isoDGR and $_D$DGR isomers show enhanced cell adhesion binding and anti-cancer properties over other isomeric forms. This is surprising given that the vast majority of peptides will comprise the L enantiomer of aspartic acid. Peptide produced by gene expression will all comprise the L enantiomer.

We have also found that cytokines conjugated to deamidated NGR peptides have surprising activity. We have previously found that the therapeutic index of certain cytokines can be remarkably improved and their immunotherapeutic properties can be enhanced by coupling with a ligand comprising the NGR motif, such as a modified ligand of aminopeptidase-N receptor (CD13). CD13 is a trans-membrane glycoprotein of 150 kDa highly conserved in various species. It is expressed on normal cells as well as in myeloid tumor lines, in the angiogenic endothelium and is some epithelia. CD13 receptor is usually identified as "NGR" receptor, in that its peptide ligands share the amino acidic "NGR" motif. We have now surprisingly found that similar or indeed improved results may be achieved using a modified ligand in which the asparaginyl (Asn or N) residue in the NGR motif is modified to aspartyl (Asp or D), i.e. a "DGR" motif, by deamidation. TNF coupled with such a modified ligand of CD13 receptor and IFNγ may also act synergistically so that effective anti-tumor activity may be seen upon co-administration at dosages which are below the effective doses individually. In addition, we have found that the anti-tumor activity of a combination of the modified TNF and another anti-tumor agent, such as mephalan, or doxorubicin or cis-platin or gemcitabine or taxol, is increased by administration of IFNγ.

STATEMENTS OF THE INVENTION

According to a first aspect of the invention there is provided a peptide which selectively inhibits $α_v β_3$ integrin which comprises the deamidation product of a peptide comprising the NGR motif.

According to another aspect of the invention there is provided a peptide which inhibits endothelial cell adhesion to vitronectin which comprises the deamidation product of a peptide comprising the NGR motif.

According to another aspect of the invention there is provided a peptide comprising the deamidation product of an extracellular matrix protein such as, but not limited to, fibronectin, vitronectin, collagen or laminin or a fragment or derivative thereof. Preferably the fragment comprises at least 5, 10, 15, 20, 25, 30, 35, 40, 45, 50, or 100 consecutive amino acids of the deamidated matrix protein and preferably comprises a deamidated NGR motif of said protein.

Preferably the peptide comprises the deamidation product of fibronectin, more preferably the deamidation product of the FN-I$_5$, FN-I$_7$ FN-II$_1$ or FN-III$_9$ module of fibronectin, more preferably the deamidation product of the FN-I$_5$ module of fibronectin, or a fragment or derivative thereof or the deamidation product of the FN-I$_7$ module of fibronectin, or a fragment or derivative thereof. Preferably the fragment comprises at least 5, 10, 15, 20, 25, 30, 35, 40, 45, 50, or 100 consecutive amino acids of fibronectin and preferably comprises a deamidated NGR motif of said protein.

In one embodiment the peptide consists of the deamidation product of the extracellular matrix protein or fragment or derivative thereof.

According to another aspect of the invention there is provided the deamidation product of a peptide comprising the sequence XNGRX' (SEQ ID NO: 1) wherein X is selected from the group consisting of L, V, A, C, G, Y, P, H, K, Q and I and X' is selected from the group consisting of C, G, H, L, E, T, Q, R, S and P.

Preferably the peptide comprises the deamidation product of a peptide comprising a sequence selected from CNGRCVSGCAGRC (SEQ ID NO: 2), NGRAHA (SEQ ID NO: 3), GNGRG (SEQ ID NO: 4), CVLNGRMEC (SEQ ID NO: 5), CNGRC (SEQ ID NO: 6), CNGRCG (SEQ ID NO: 7), LNGRE (SEQ ID NO: 8), YNGRT (SEQ ID NO: 9), LQCICTGNGRGEWKCE (SEQ ID NO: 10), LQCISTGNGRGEWKCE (SEQ ID NO: 11), CICTGNGRGEWKC (SEQ ID NO: 12), CISTGNGRGEWKC (SEQ ID NO: 13), MRCTCVGNGRGEWTCY (SEQ ID NO: 14), MRCTSVGNGRGEWTCY (SEQ ID NO: 15), CTCVGNGRGEWTC (SEQ ID NO: 16) and CTSVGNGRGEWTC (SEQ ID NO: 17).

In one embodiment the peptide consists of the deamidation product of a peptide having a sequence selected from CNGRCVSGCAGRC (SEQ ID NO: 2), NGRAHA (SEQ ID NO: 3), GNGRG (SEQ ID NO: 4), CVLNGRMEC (SEQ ID NO: 5), CNGRC (SEQ ID NO: 6), CNGRCG (SEQ ID NO: 7), LNGRE (SEQ ID NO: 8), YNGRT (SEQ ID NO: 9), LQCICTGNGRGEWKCE (SEQ ID NO: 10), LQCISTGNGRGEWKCE (SEQ ID NO: 11), CICTGNGRGEWKC (SEQ ID NO: 12), CISTGNGRGEWKC (SEQ ID NO: 13), MRCTCVGNGRGEWTCY (SEQ ID NO: 14), MRCTSVGNGRGEWTCY (SEQ ID NO: 15), CTCVGNGRGEWTC (SEQ ID NO: 16) and CTSVGNGRGEWTC (SEQ ID NO: 17).

Preferably the peptide comprises the deamidation product of a peptide comprising a sequence selected from cycloCVLNGRMEC (SEQ ID NO: 5), linear CNGRC (SEQ ID NO: 6), cyclic CNGRC (SEQ ID NO: 6), linear CNGRCG (SEQ ID NO: 7) and cyclic CNGRCG (SEQ ID NO: 7).

In one embodiment the peptide consists of the deamidation product of a peptide having a sequence selected from cycloCVLNGRMEC (SEQ ID NO: 5), linear CNGRC (SEQ ID NO: 6), cyclic CNGRC (SEQ ID NO: 6), linear CNGRCG (SEQ ID NO: 7) and cyclic CNGRCG (SEQ ID NO: 7).

According to another aspect of the present invention there is provided a peptide comprising the DGR motif wherein said peptide selectively inhibits $α_v β_3$ integrin.

According to another aspect of the present invention there is provided a peptide comprising the DGR motif wherein said peptide inhibits endothelial cell adhesion to vitronectin.

Preferably the peptide comprises the sequence XDGR' (SEQ ID NO: 18) wherein X is selected from the group consisting of L, V, A, C, G, Y, P, H, K, Q and I and X' is selected from the group consisting of C, G, H, L, E, T, Q, R, S and P.

Preferably the peptide comprises a sequence selected from CDGRCVSGCAGRC (SEQ ID NO: 19), DGRAHA (SEQ ID NO: 20), GDGRG (SEQ ID NO: 21), CVLDGRMEC (SEQ ID NO: 22), CDGRC (SEQ ID NO: 23), CDGRCG (SEQ ID NO: 24), LDGRE (SEQ ID NO: 25), YDGRT (SEQ ID NO: 26), LQCICTGDGRGEWKCE (SEQ ID NO: 27), LQCISTGDGRGEWKCE (SEQ ID NO: 28), CICTGDGRGEWKC (SEQ ID NO: 29), CISTGDGRGEWKC (SEQ ID NO: 30), MRCTCVGDGRGEWTCY (SEQ ID NO: 31), MRCTSVGDGRGEWTCY (SEQ ID NO: 32), CTCVGDGRGEWTC (SEQ ID NO: 33) or CTS- VGDGRGEWTC (SEQ ID NO: 34), more preferably a sequence selected from cycloCVLDGRMEC (SEQ ID NO: 22X), linear CDGRC (SEQ ID NO: 23), cyclic CDGRC (SEQ ID NO: 23), linear CDGRCG (SEQ ID NO: 24) and cyclic CDGRCG (SEQ ID NO: 24).

In one embodiment the peptide consists of a sequence selected from CDGRCVSGCAGRC (SEQ ID NO: 19), DGRAHA (SEQ ID NO: 20), GDGRG (SEQ ID NO: 21), CVLDGRMEC (SEQ ID NO: 22), CDGRC (SEQ ID NO: 23), CDGRCG (SEQ ID NO: 24), LDGRE (SEQ ID NO: 25), YDGRT (SEQ ID NO: 26), LQCICTGDGRGEWKCE (SEQ ID NO: 27), LQCISTGDGRGEWKCE (SEQ ID NO: CICTGDGRGEWKC (SEQ ID NO: 29), CISTGDGRGEWKC (SEQ ID NO: 30), MRCTCVGDGRGEWTCY (SEQ ID NO: 31), MRCTSVGDGRGEWTCY (SEQ ID NO: 32), CTCVGDGRGEWTC (SEQ ID NO: 33) or CTSVGDGRGEWTC (SEQ ID NO: 34), more preferably a sequence selected from cycloCVLDGRMEC (SEQ ID NO: 22X), linear CDGRC (SEQ ID NO: 23), cyclic CDGRC (SEQ ID NO: 23), linear CDGRCG (SEQ ID NO: 24) and cyclic CDGRCG (SEQ ID NO: 24).

According to another aspect of the present invention there is provided a peptide comprising an isoDGR motif.

Preferably the peptide comprises the sequence XisoDGRX' (SEQ ID NO: 54) wherein X is selected from the group consisting of L, V, A, C, G, Y, P, H, K, Q and I and X' is selected from the group consisting of C, G, H, L, E, T, Q, R, S and P.

Preferably the peptide comprises a sequence selected from CisoDGRCVSGCAGRC (SEQ ID NO: 55), isoDGRAHA (SEQ ID NO: 56), GisoDGRG (SEQ ID NO: 57), CVLisoDGRMEC (SEQ ID NO: 58), CisoDGRC (SEQ ID NO: 59), CisoDGRCG (SEQ ID NO: 60), LisoDGRE (SEQ ID NO: 61), YisoDGRT (SEQ ID NO: 62), LQCICTGisoDGRGEWKCE (SEQ ID NO: 63), LQCISTGisoDGRGEWKCE (SEQ ID NO: 64), CICTGisoDGRGEWKC (SEQ ID NO: 65), CISTGisoDGRGEWKC (SEQ ID NO: 66), MRCTCVGisoDGRGEWTCY (SEQ ID NO: 67), MRCTSVGisoDGRGEWTCY (SEQ ID NO: 68), CTCVGisoDGRGEWTC (SEQ ID NO: 69) or CTSVGisoDGRGEWTC (SEQ ID NO: 70), more preferably a sequence selected from cycloCVLisoDGRMEC (SEQ ID NO: 58), linear CisoDGRC (SEQ ID NO: 59), cyclic CisoDGRC (SEQ ID NO: 59), linear CisoDGRCG (SEQ ID NO: 60) and cyclic CisoDGRCG (SEQ ID NO: 60).

In one embodiment the peptide consists of a sequence selected from CisoDGRCVSGCAGRC (SEQ ID NO: 55), isoDGRAHA (SEQ ID NO: 56), GisoDGRG (SEQ ID NO: 57), CVLisoDGRMEC (SEQ ID NO: 58), CisoDGRC (SEQ ID NO: 59), CisoDGRCG (SEQ ID NO: 60), LisoDGRE (SEQ ID NO: 61), YisoDGRT (SEQ ID NO: 62), LQCICTGisoDGRGEWKCE (SEQ ID NO: 63), LQCISTGisoDGRGEWKCE (SEQ ID NO: 64), CICTGisoDGRGEWKC (SEQ ID NO: 65), CISTGisoDGRGEWKC (SEQ ID NO: 66), MRCTCVGisoDGRGEWTCY (SEQ ID NO: 67), MRCTSVGisoDGRGEWTCY (SEQ ID NO: 68), CTCVGisoDGRGEWTC (SEQ ID NO: 69) or CTSVGisoDGRGEWTC (SEQ ID NO: 70), more preferably a sequence selected from cycloCVLisoDGRMEC (SEQ ID NO: 58), linear CisoDGRC (SEQ ID NO: 59), cyclic CisoDGRC (SEQ ID NO: 59), linear CisoDGRCG (SEQ ID NO: 60) and cyclic CisoDGRCG (SEQ ID NO: 60).

According to another aspect of the present invention there is provided a peptide comprising an $_L$isoDGR motif.

Preferably the peptide comprises the sequence $X_L$isoDGRX' (SEQ ID NO: 54) sequence wherein X is selected from the group consisting of L, V, A, C, G, Y, P, H, K, Q or I and X' is selected from the group consisting of C, G, H, L, E, T, Q, R, S or P, and wherein the isoD of SEQ ID NO: 54 is the $_L$isoD entantiomer.

Preferably the peptide comprises a sequence selected from $C_L$isoDGRCVSGCAGRC (SEQ ID NO: 55), $_L$isoDGRAHA (SEQ ID NO: 56), $G_L$isoDGRG (SEQ ID NO: 57), CVL$_L$isoDGRMEC (SEQ ID NO: 58), $C_L$isoDGRC (SEQ ID NO: 59), $C_L$isoDGRCG (SEQ ID NO: 60), $L_L$isoDGRE (SEQ ID NO: 61), $Y_L$isoDGRT (SEQ ID NO: 62), LQCICTG$_L$isoDGRGEWKCE (SEQ ID NO: 63), LQCISTG$_L$isoDGRGEWKCE (SEQ ID NO: 64), CICTG$_L$isoDGRGEWKC (SEQ ID NO: 65), CISTG$_L$isoDGRGEWKC (SEQ ID NO: 66), MRCTCVG$_L$isoDGRGEWTCY (SEQ ID NO: 67), MRCTSVG$_L$isoDGRGEWTCY (SEQ ID NO: 68), CTCVG$_L$isoDGRGEWTC (SEQ ID NO: 69) and CTSVG$_L$isoDGRGEWTC (SEQ ID NO: 70) more preferably a sequence selected from cycloCVL$_L$isoDGRMEC (SEQ ID NO: 58), linear $C_L$isoDGRC (SEQ ID NO: 59), cyclic $C_L$isoDGRC (SEQ ID NO: 59), linear $C_L$isoDGRCG (SEQ ID NO: 60) and cyclic $C_L$isoDGRCG (SEQ ID NO: 60), and wherein the isoD of each of the SEQ ID NOs: is the $_L$isoD enantiomer.

In one embodiment the peptide consists of a sequence selected from isoDGRCVSGCAGRC (SEQ ID NO: 55), $_L$isoDGRAHA (SEQ ID NO: 56), $G_L$isoDGRG (SEQ ID NO: 57), CVL$_L$isoDGRMEC (SEQ ID NO: 58), $C_L$isoDGRC (SEQ ID NO: 59), $C_L$isoDGRCG (SEQ ID NO: 60), $L_L$isoDGRE (SEQ ID NO: 61), $Y_L$isoDGRT (SEQ ID NO: 62), LQCICTG$_L$isoDGRGEWKCE (SEQ ID NO: 63), LQCISTG$_L$isoDGRGEWKCE (SEQ ID NO: 64), CICTG$_L$isoDGRGEWKC (SEQ ID NO: 65), CISTG$_L$isoDGRGEWKC (SEQ ID NO: 66), MRCTCVG$_L$isoDGRGEWTCY (SEQ ID NO: 67), MRCTSVG$_L$isoDGRGEWTCY (SEQ ID NO: 68), CTCVG$_L$isoDGRGEWTC (SEQ ID NO: 69) and CTSVG$_L$isoDGRGEWTC (SEQ ID NO: 70) more preferably a sequence selected from cycloCVL$_L$isoDGRMEC (SEQ ID NO: 58), linear $C_L$isoDGRC (SEQ ID NO: 59), cyclic $C_L$isoDGRC (SEQ ID NO: 59), linear $C_L$isoDGRCG (SEQ ID NO: 60) and cyclic $C_L$isoDGRCG (SEQ ID NO: 60), and wherein the isoD of each of the SEQ ID NOs: is the $_L$ isoD enantiomer.

According to another aspect of the present invention there is provided a peptide comprising a $_D$DGR motif.

Preferably the peptide comprises the sequence $X_D$DGRX' (SEQ ID NO: 18) wherein X is selected from L, V, A, C, G, Y, P, H, K, Q or I and X' is selected from C, G, H, L, E, T, Q, R, S or P, and wherein the "D" of the SEQ ID NO: 18 DGR motif is the $_D$D entantiomer.

Preferably the peptide comprises a sequence selected from $C_D$DGRCVSGCAGRC (SEQ ID NO: 19), $_D$DGRAHA (SEQ ID NO: 20), $G_D$DGRG (SEQ ID NO: 21), CVL$_D$DGRMEC (SEQ ID NO: 22), $C_D$DGRC (SEQ ID NO: 23), $C_D$DGRCG (SEQ ID NO: 24), $L_D$DGRE (SEQ ID NO: 25), $Y_D$DGRT (SEQ ID NO: 26), LQCICTG$_D$DGRGEWKCE (SEQ ID NO: 27), LQCISTG$_D$DGRGEWKCE (SEQ ID NO: 28), CICTG$_D$DGRGEWKC (SEQ ID NO: 29), CISTG$_D$DGRGEWKC (SEQ ID NO: 30), MRCTCVG$_D$DGRGEWTCY (SEQ ID NO: 31), MRCTSVG$_D$DGRGEWTCY (SEQ ID NO: 32), CTCVG$_D$DGRGEWTC (SEQ ID NO: 33) and CTSVG$_D$DGRGEWTC (SEQ ID NO: 34) more preferably a sequence selected from cycloCVL$_D$DGRMEC (SEQ ID NO: 22), linear $C_D$DGRC (SEQ ID NO: 23), cyclic $C_D$DGRC (SEQ ID NO: 23), linear $C_D$DGRCG (SEQ ID NO: 24) and cyclic C_DDGRCG (SEQ ID NO: 24), and wherein the "D" of the DGR motif of each of the SEQ ID NOs: is the _DD enantiomer.

In one embodiment the peptide consists of a sequence selected from C_DDGRCVSGCAGRC (SEQ ID NO: 19), _DDGRAHA (SEQ ID NO: 20), G_DDGRG (SEQ ID NO: 21), CVL_DDGRMEC (SEQ ID NO: 22), C_DDGRC (SEQ ID NO: 23), C_DDGRCG (SEQ ID NO: 24), L_DDGRE (SEQ ID NO: 25), Y_DDGRT (SEQ ID NO: 26), LQCICT-G_DDGRGEWKCE (SEQ ID NO: 27), LQCIST-G_DDGRGEWKCE (SEQ ID NO: 28), CICT-G_DDGRGEWKC (SEQ ID NO: 29), CISTG_DDGRGEWKC (SEQ ID NO: 30), MRCTCVG_DDGRGEWTCY (SEQ ID NO: 31), MRCTSVG_DDGRGEWTCY (SEQ ID NO: 32), CTCVG_DDGRGEWTC (SEQ ID NO: 33) and CTS-VG_DDGRGEWTC (SEQ ID NO: 34) more preferably a sequence selected from cycloCVL_DDGRMEC (SEQ ID NO: 22), linear C_DDGRC (SEQ ID NO: 23), cyclic C_DDGRC (SEQ ID NO: 23), linear C_DDGRCG (SEQ ID NO: 24) and cyclic C_DDGRCG (SEQ ID NO: 24), and wherein the "D" of the DGR motif of each of the SEQ ID NOs: is the _DD enantiomer.

In one embodiment the peptide comprising the isoDGR motif, _LisoDGR motif or _DDGR motif comprises a deamidation product of an extracellular matrix protein, such as, but not limited to fibronectin, vitronectin, collagen or laminin, more preferably a deamidation product fibronectin, more preferably a deamidation product of FN-I$_5$, FN-I$_7$, FN-II$_1$ or FN-III$_9$ module of fibronectin, or a fragment or derivative thereof.

Preferably the fragment comprises at least 5, 10, 15, 20, 25, 30, 35, 40, 45, 50, or 100 consecutive amino acids of the extracellular matrix protein or module.

Preferably the peptide of the present invention selectively inhibits $\alpha_v\beta_3$ integrin and/or inhibits endothelial cell adhesion to vitronectin. Preferably the peptide inhibits $\alpha_v\beta_3$ but does not inhibit $\alpha_v\beta_5$, $\alpha_5\beta_1$ and $\alpha_1\beta_1$.

Preferably the IC$_{50}$ of the peptide in respect of $\alpha_v\beta_3$ inhibition is <0.5 µM, preferably <0.2 µM. Preferably the assay used to determine the IC$_{50}$ is determined using streptavidin-peroxidase conjugate complexes as described in the materials and methods. Preferably the IC$_{50}$ of the peptide in respect of $\alpha_v\beta_5$ and/or $\alpha_5\beta_1$ and/or $\alpha_1\beta_1$, is >1.0 µM, more preferably >2.0 µM, >3.0 µM, >4.0 µM.

Preferably the peptide of the present invention inhibits tumor growth.

Preferably the peptide of the present invention inhibits angiogenisis.

In one embodiment the peptide of the present invention does not comprise an additional therapeutic agent, including an anticancer agent or cytokine.

Preferably the peptide of the present invention comprises a turn involving the G and R residues of the DGR motif.

In one embodiment the peptide of the present invention comprises up to 350, 100, 50, 25, 15, 10 or 5 amino acids.

According to another aspect of the present invention there is provided a conjugation product comprising a peptide of the present invention. Preferably the conjugation product is between a peptide of the present invention and a drug, cytokine, cytokine fragment toxin, apoptotic peptide, biological response modifier radionuclide, viral particle, gene or an imaging compound. In one embodiment the drug is an anticancer agent such as doxorubicin, melphalan, cis-platin, gemcitabine or taxol.

According to another aspect of the present invention there is provided a pharmaceutical composition comprising a pharmaceutically effective amount of a peptide or conjugation product of the present invention, preferably comprising a pharmaceutically acceptable carrier, diluent or excipient.

Preferably the composition comprises essentially no peptide or conjugate having an NGR motif. In particular, when the composition comprises a deamidated peptide, it preferably comprises essentially no precursor peptide i.e. essentially no starting material. Preferably the peptide or conjugate of the composition comprises less than 40, 30, 20, 15, 10, 5, 3 or 1% starting material.

Preferably compositions of the present invention comprising peptides and conjugates which contain DGR motifs are substantially free of the corresponding peptides and conjugates which contain the corresponding NGR motif. Preferably the proportion of DGR containing peptide relative to the total peptide (i.e., DGR and NGR containing peptide) is more than 60%, more preferably more than 70%, more preferably more than 80%, more preferably more than 85%, more preferably more than 90%, more preferably more than 95%, more preferably more than 97%, more preferably more than 99% w/w.

The composition of the present invention may be in the form of an injectable solution or suspension or a liquid for infusions.

The composition of the present invention may be in the form of liposomes.

According to another aspect of the present invention there is provided a method of treating or diagnosing a patient suffering from disorders involving $\alpha v\beta 3$ such as but not limited to osteoporosis, arthritis, diabetic retinopathy, macular degeneration, restenosis or hemangioma comprising administering the peptide, conjugation product or pharmaceutical composition of the invention.

According to another aspect of the present invention there is provided a method of treating or diagnosing a patient suffering from osteoporosis, arthritis, diabetic retinopathy, macular degeneration, restenosis or hemangioma comprising administering the peptide, conjugation product or pharmaceutical composition of the invention.

According to another aspect of the present invention there is provided a method of treating or diagnosing a patient suffering from a cancer, such as but not limited to lung, pancreas, breast, colon, larynx or ovary cancer, comprising administering the peptide, conjugation product or pharmaceutical composition of the invention.

According to another aspect of the present invention there is provided a conjugation product between a peptide of the present invention and a cytokine.

According to another aspect of the present invention there is provided a conjugation product between a cytokine and a targeting moiety comprising the deamidation product of the NGR motif.

According to another aspect of the present invention there is provided a conjugation product between a cytokine and a targeting moiety comprising the DGR motif, including but not limited to CDGRCVSGCAGRC (SEQ ID NO: 19), DGRAHA (SEQ ID NO: 20), GDGRG (SEQ ID NO: 21), CVLDGRMEC (SEQ ID NO: 22), CDGRC (SEQ ID NO: 23), CDGRCG (SEQ ID NO: 24), LDGRE (SEQ ID NO: 25), YDGRT (SEQ ID NO: 26), LQCICTGDGRGEWKCE (SEQ ID NO: 27), LQCISTGDGRGEWKCE (SEQ ID NO: 28), CICTGDGRGEWKC (SEQ ID NO: 29), CISTGDGRGEWKC (SEQ ID NO: 30), MRCTCVGDGRGEWTCY (SEQ ID NO: 31), MRCTSVGDGRGEWTCY (SEQ ID NO: 32), CTCVGDGRGEWTC (SEQ ID NO: 33) or CTSVGDGRGEWTC (SEQ ID NO: 34) more preferably cycloCVLDGRMEC (SEQ ID NO: 22), linear CDGRC (SEQ ID NO: 23), cyclic CDGRC (SEQ ID NO: 23), linear CDGRCG (SEQ ID NO: 24) or cyclic CDGRCG (SEQ ID NO: 24). Preferably the DGR motif is isoDGR motif, more preferably $_L$isoDGR. In one embodiment the DGR motif is $_D$DGR.

A non-limiting list of cytokines used in the conjugate of the present invention is TNFα, TNFβ, IFNα, IFNβ, IFNγ, IL-1, 2, 4, 6, 7, 12, 15, EMAP II, vascular endothelial growth factor (VEGF), PDGF, PD-ECGF or a chemokine. Preferably the cytokine of the conjugate is selected from TNF, IFNγ, IL-12 IP-10, IL-7 or EMAP II. More preferably the cytokine is selected from TNF, IFNγ or IL-12

Preferably the TNF is TNFα or TNFβ.

In one embodiment the cytokine is derivatized with polyethylene glycol or an acyl residue.

In another embodiment the cytokine is further conjugated with a compound selected from the group consisting of an antibody, an antibody fragment, and biotin, wherein said antibody or fragment thereof is directed to a compound selected from the group consisting of a tumoral antigen, a tumoral angiogenic marker or a component of the extracellular matrix.

In another embodiment the cytokine is TNF and is conjugated to both the targeting moiety and a compound selected from the group consisting of an antibody, and antibody fragment, and biotin.

According to another aspect of the present invention there is provided a pharmaceutical composition comprising an effective amount of a conjugation product of TNF of the present invention, and an effective amount of IFNγ or a polynucleotide encoding therefor.

Preferably the peptide or conjugate of the present invention is other than when formed in vivo by metabolism of a peptide or conjugate comprising an NGR motif.

According to another aspect of the present invention there is provided a peptide or conjugate of the present invention obtainable by heat treatment.

The composition of the present invention may further comprise another antitumor agent, such as, but not limited to doxorubicin or melphalan, or cis-platin or gemcitabine or taxol or a diagnostic tumor-imaging compound.

DETAILED DESCRIPTION

Various preferred features and embodiment of the present invention will now be described by way of non-limiting example.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

DGR Motif

It is well known that aspartic acid may exist in a different structural isomeric form, namely isoaspartic acid (see FIG. 14).

Aspartic acid and isoaspartic acid are each chiral molecules, and the different isomers can be referred to as $_L$-Asp ($_L$D), $_L$isoAsp ($_L$isoD), $_D$Asp ($_D$D) and $_D$isoAsp ($_D$isoD) where $_L$isoD and $_D$isoD represent the entantiomers of isoaspartic acid and $_L$D and $_D$D represent the enantiomers of aspartic acid.

When the prior art refers to DGR, it in essence refers to $_L$DGR. As used herein, the term DGR refers to a DGR motif that comprises $_D$D and/or $_L$isoD or mixtures thereof and which may further comprise $_L$D and $_D$isoD. Preferably, the DGR is generated by deamidation of the corresponding NGR motif. In one embodiment the DGR motif comprises at least 10 w/w % $_L$isoDGR. In another embodiment the DGR motif comprises at least 10 w/w % $_D$DGR By a peptide or targeting moiety comprising an isoDGR motif it is meant a peptide or targeting moiety wherein the DGR motif is substantially in the form of isoDGR. By substantially, it is meant the w/w % of peptide or targeting moiety comprising the isoDGR motif relative to total DGR containing peptide or targeting moiety is greater than 55%, more preferably greater than 60% more preferably greater than 65%, more preferably greater than 70%, more preferably greater than 75%, more preferably greater than 80%, more preferably greater than 85%, more preferably greater than 90%, more preferably greater than 95%, more preferably greater than 97%, more preferably greater than 99%. The isoDGR may comprise both enantiomers of $_{L/D}$isoD, but preferably comprises at least 5, more preferably at least 10, more preferably at least 30, more preferably at least 40, more preferably at least 50 w/w % of $_L$isoD.

By a peptide or targeting moiety comprising an $_L$isoDGR motif it is meant a peptide or targeting moiety wherein the DGR motif is substantially in the form of $_L$isoDGR. By substantially it is meant the w/w % of peptide or targeting moiety comprising the $_L$isoDGR motif relative to total DGR containing peptide or targeting moiety is greater than 55%, more preferably greater than 60% more preferably greater than 65%, more preferably greater than 70%, more preferably greater than 75%, more preferably greater than 80%, more preferably greater than 85%, more preferably greater than 90%, more preferably greater than 95%, more preferably greater than 97%, more preferably greater than 99%.

By a peptide or targeting moiety comprising a $_D$DGR motif it is meant a peptide or targeting moiety wherein the DGR motif is substantially in the form of $_D$DGR. By substantially it is meant the w/w % of peptide or targeting moiety comprising the $_D$DGR motif relative to total DGR containing peptide or targeting moiety is greater than 55%, more preferably greater than 60% more preferably greater than 65%, more preferably greater than 70%, more preferably greater than 75%, more preferably greater than 80%, more preferably greater than 85%, more preferably greater than 90%, more preferably greater than 95%, more preferably greater than 97%, more preferably greater than 99%.

The DGR motif of the present invention preferably comprises a turn involving the G and R residues. When the DGR motif is arrived at by deamidation of the corresponding NGR motif, it is preferable that the NGR motif comprises a turn involving the G and R residues. The structure-activity relationship of linear and cyclic peptides containing the NGR motif and their ability to target tumors is discussed in Colombo et al., J. Biol. Chem., 2002, 49, 47891-47897. The Experiments carried out in animal models showed that both GNGRG (SEQ ID NO: 4) and CNGRC (SEQ ID NO: 6) can target TNF to tumors. Molecular dynamic simulation of cyclic CNGRC (SEQ ID NO: 6) showed the presence of a bend geometry involving residues $Gly^3$-$Arg^g$, stabilised by the formation of a disulphide bridge. Molecular dynamic simulation of the same peptide without disulfide constraints showed that the most populated and thermodynamically favoured configuration is characterised by the presence of a β-turn involving residues $Gly^3$-$Arg^4$. These results suggest that the NGR motif has a strong propensity to form β-turn in linear peptides and may explain the finding that GNGRG (SEQ ID NO: 4) peptide can target TNF to tumors, albeit to a lower extent than CNGRC (SEQ ID NO: 6).

Three-dimensional structure analysis of the fibronectin domain FN-$I_5$ showed that the GNGRG (SEQ ID NO: 4) motif forms an exposed loop, likely accessible to water and to receptors (see FIG. 1B). The molecular dynamic simulation of an NGR-peptide with flanking cysteines (CNGRC (SEQ ID NO: 6)), used in the present application as a molecular surrogate of the fibronectin NGR motif, showed that its structure is superimposable to that of the FN loop (Di Matteo et al., 2002).

Deamidation

Deamidation of asparagine residues results in the conversion to isoaspartate and aspartate. The process is shown in FIG. 14.

The deamidation referred to herein may be carried under any suitable conditions readily identified by a person of skill in the art. The deamidation of the present invention is carried out in vitro.

In one embodiment, the deamidation is carried out by heating the NGR comprising peptide. The temperature required may vary depending on the exact nature of the peptide and are readily determinable by one skilled in the art. Preferably the temperature is sufficient to induce deamidation of the asparagine residue, but is not so high as to denature or damage the peptide. A suitable temperatures may be, for example, between 25-50, 30-40 or 35-40° C.

The deamidation may also be performed by incubating the peptide in basic conditions, usually about pH 8 e.g., by incubating in an ammonium bicarbonate solution. The exact nature of the basic conditions may vary depending on the exact nature of the peptide but are readily determinable by one skilled in the art. Preferably the basic conditions are sufficient to induce deamidation of the asparagine residue, but are not such that the remaining peptide is denatured or damaged. Suitable basic conditions may be, for example, between pH 7.5-9.0, 8.0-9.0 or 8.0-8.5.

In a preferred embodiment the deamidation is carried out under heating in a basic solvent.

Peptide

The term "peptide" as used herein includes polypeptides and proteins. The term "polypeptide" includes single-chain polypeptide molecules as well as multiple-polypeptide complexes where individual constituent polypeptides are linked by covalent or non-covalent means. The term "polypeptide" includes peptides of two or more amino acids in length, typically having more than 5, 10, 20, 30, 40, 50 or 100, amino acids.

Peptides of the present invention may be administered therapeutically to patients. It is preferred to use peptides that do not consisting solely of naturally-occurring amino acids but which have been modified, for example to reduce immunogenicity, to increase circulatory half-life in the body of the patient, to enhance bioavailability and/or to enhance efficacy and/or specificity.

A number of approaches have been used to modify peptides for therapeutic application. One approach is to link the peptides or proteins to a variety of polymers, such as polyethylene glycol (PEG) and polypropylene glycol (PPG)—see for example U.S. Pat. Nos. 5,091,176, 5,214,131 and U.S. Pat. No. 5,264,209.

Replacement of naturally-occurring amino acids with a variety of uncoded or modified amino acids such as D-amino acids and N-methyl amino acids may also be used to modify peptides Another approach is to use bifunctional crosslinkers, such as N-succinimidyl 3-(2 pyridyldithio)propionate, succinimidyl 6-[3-(2 pyridyldithio)propionamido]hexanoate, and sulfosuccinimidyl 6-[3-(2 pyridyldithio)propionamido]hexanoate (see U.S. Pat. No. 5,580,853).

It may be desirable to use derivatives of the peptides of the invention which are conformationally constrained. Conformational constraint refers to the stability and preferred conformation of the three-dimensional shape assumed by a peptide. Conformational constraints include local constraints, involving restricting the conformational mobility of a single residue in a peptide; regional constraints, involving restricting the conformational mobility of a group of residues, which residues may form some secondary structural unit; and global constraints, involving the entire peptide structure.

The active conformation of the peptide may be stabilised by a covalent modification, such as cyclization or by incorporation of gamma-lactam or other types of bridges. For example, side chains can be cyclized to the backbone so as create a L-gamma-lactam moiety on each side of the interaction site. See, generally, Hruby et al., "Applications of Synthetic Peptides," in Synthetic Peptides: A User's Guide: 259-345 (W.H. Freeman & Co. 1992). Cyclization also can be achieved, for example, by formation of cysteine bridges, coupling of amino and carboxy terminal groups of respective terminal amino acids, or coupling of the amino group of a Lys residue or a related homolog with a carboxy group of Asp, Glu or a related homolog. Coupling of the alpha-amino group of a polypeptide with the epsilon-amino group of a lysine residue, using iodoacetic anhydride, can be also undertaken. See Wood and Wetzel, 1992, Int'l J. Peptide Protein Res. 39: 533-39.

Another approach described in U.S. Pat. No. 5,891,418 is to include a metal-ion complexing backbone in the peptide structure. Typically, the preferred metal-peptide backbone is based on the requisite number of particular coordinating groups required by the coordination sphere of a given complexing metal ion. In general, most of the metal ions that may prove useful have a coordination number of four to six. The nature of the coordinating groups in the peptide chain includes nitrogen atoms with amine, amide, imidazole, or guanidino functionalities; sulfur atoms of thiols or disulfides; and oxygen atoms of hydroxy, phenolic, carbonyl, or carboxyl functionalities. In addition, the peptide chain or individual amino acids can be chemically altered to include a coordinating group, such as for example oxime, hydrazino, sulfhydryl, phosphate, cyano, pyridino, piperidino, or morpholino. The peptide construct can be either linear or cyclic, however a linear construct is typically preferred. One example of a small linear peptide is Gly-Gly-Gly-Gly (SEQ ID NO: 35) which has four nitrogens (an $N_4$ complexation system) in the back bone that can complex to a metal ion with a coordination number of four.

A further technique for improving the properties of therapeutic peptides is to use non-peptide peptidomimetics. A wide variety of useful techniques may be used to elucidating the precise structure of a peptide. These techniques include amino acid sequencing, x-ray crystallography, mass spectroscopy, nuclear magnetic resonance spectroscopy, computer-assisted molecular modelling, peptide mapping, and combinations thereof. Structural analysis of a peptide generally provides a large body of data which comprise the amino acid sequence of the peptide as well as the three-dimensional positioning of its atomic components. From this information, non-peptide peptidomimetics may be designed that have the required chemical functionalities for therapeutic activity but are more stable, for example less susceptible to biological degradation. An example of this approach is provided in U.S. Pat. No. 5,811,512.

Techniques for chemically synthesising therapeutic peptides of the invention are described in the above references and also reviewed by Borgia and Fields, 2000, TibTech 18: 243-251 and described in detail in the references contained therein.

Peptide Variants, Derivatives and Fragments

The terms "variant" or "derivative" in relation to the amino acid sequences of the present invention includes any substitution of, variation of, modification of, replacement of, deletion of or addition of one (or more) amino acids from or to the sequence providing the resultant amino acid sequence preferably has targeting activity, preferably having at least 25 to 50% of the activity as the polypeptides presented in the sequence listings, more preferably at least substantially the same activity.

Thus, sequences may be modified for use in the present invention. Typically, modifications are made that maintain the activity of the sequence. Thus, in one embodiment, amino acid substitutions may be made, for example from 1, 2 or 3 to 10, 20 or 30 substitutions provided that the modified sequence retains at least about 25 to 50% of, or substantially the same activity. However, in an alternative embodiment, modifications to the amino acid sequences of a polypeptide of the invention may be made intentionally to reduce the biological activity of the polypeptide. For example truncated polypeptides that remain capable of binding to target molecule but lack functional effector domains may be useful.

In general, preferably less than 20%, 10% or 5% of the amino acid residues of a variant or derivative are altered as compared with the corresponding region depicted in the sequence listings.

Amino acid substitutions may include the use of non-naturally occurring analogues, for example to increase blood plasma half-life of a therapeutically administered polypeptide (see below for further details on the production of peptide derivatives for use in therapy).

Conservative substitutions may be made, for example according to the Table below. Amino acids in the same block in the second column and preferably in the same line in the third column may be substituted for each other:

| ALIPHATIC | Non-polar | G A P |
|           |           | I L V |
|           | Polar - uncharged | C S T M |
|           |           | N Q |
|           | Polar - charged | D E |
|           |           | K R H |
| AROMATIC  |           | F W Y |

Polypeptides of the invention also include fragments of the above mentioned polypeptides and variants thereof, including fragments of the sequences. Preferred fragments include those which include an epitope or binding domain. Suitable fragments will be at least about 5, e.g. 10, 12, 15 or 20 amino acids in length. They may also be less than 200, 100 or 50 amino acids in length. Polypeptide fragments of the proteins and allelic and species variants thereof may contain one or more (e.g. 2, 3, 5, or 10) substitutions, deletions or insertions, including conserved substitutions. Where substitutions, deletion and/or insertions have been made, for example by means of recombinant technology, preferably less than 20%, 10% or 5% of the amino acid residues depicted in the sequence listings are altered.

Polypeptides and conjugates of the invention are typically made by recombinant means, for example as described below. However they may also be made by synthetic means using techniques well known to skilled persons such as solid phase synthesis. Various techniques for chemical synthesising peptides are reviewed by Borgia and Fields, 2000, TibTech 18: 243-251 and described in detail in the references contained therein.

Polynucleotides

Polynucleotides for use in the invention comprise nucleic acid sequences encoding peptides and conjugates of the invention. In particular, the polynucleotides may encode precursor peptides or conjugates comprising the NGR motif which, upon deamidation, renders peptides and conjugates comprising the corresponding DGR motif.

It will be understood by a skilled person that numerous different polynucleotides can encode the same polypeptide as a result of the degeneracy of the genetic code. In addition, it is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

Polynucleotides of the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the field of the invention.

Such modifications may be carried out in order to enhance the in vivo activity or life span of polynucleotides.

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells include bacteria such as *E. coli*, yeast, mammalian cell lines and other eukaryotic cell lines, for example insect Sf9 cells.

Preferably, a polynucleotide of the invention in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

The control sequences may be modified, for example by the addition of further transcriptional regulatory elements to make the level of transcription directed by the control sequences more responsive to transcriptional modulators.

Vectors of the invention may be transformed or transfected into a suitable host cell as described below to provide for expression of a protein of the invention. This process may comprise culturing a host cell transformed with an expression vector as described above under conditions to provide for expression by the vector of a coding sequence encoding the protein, and optionally recovering the expressed protein.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used, for example, to transfect or transform a host cell.

Control sequences operably linked to sequences encoding the protein of the invention include promoters/enhancers and other expression regulation signals. These control sequences may be selected to be compatible with the host cell for which the expression vector is designed to be used in. The term "promoter" is well-known in the art and encompasses nucleic acid regions ranging in size and complexity from minimal promoters to promoters including upstream elements and enhancers.

The promoter is typically selected from promoters which are functional in mammalian cells, although prokaryotic promoters and promoters functional in other eukaryotic cells may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of a-actin, b-actin, tubulin) or, alternatively, a tissue-specific manner (such as promoters of the genes for pyruvate kinase). Tissue-specific promoters specific for certain cells may also be used. They may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter or the human cytomegalovirus (CMV) IE promoter.

It may also be advantageous for the promoters to be inducible so that the levels of expression of the heterologous gene can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above.

Vectors and polynucleotides of the invention may be introduced into host cells for the purpose of replicating the vectors/polynucleotides and/or expressing the proteins of the invention encoded by the polynucleotides of the invention.

Although the proteins of the invention may be produced using prokaryotic cells as host cells, it is preferred to use eukaryotic cells, for example yeast, insect or mammalian cells, in particular mammalian cells.

Vectors/polynucleotides of the invention may introduced into suitable host cells using a variety of techniques known in the art, such as transfection, transformation and electroporation. Where vectors/polynucleotides of the invention are to be administered to animals, several techniques are known in the art, for example infection with recombinant viral vectors such as retroviruses, herpes simplex viruses and adenoviruses, direct injection of nucleic acids and biolistic transformation. Host cells comprising polynucleotides of the invention may be used to express conjugates of the invention. Host cells may be cultured under suitable conditions which allow expression of the polypeptides and conjugates of the invention. Expression of the products of the invention may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Conjugates

The present invention relates to a conjugate which is a molecule comprising a peptide or targeting moiety of the invention linked to at least one other agent, including, but not limited to, a drug, a cytokine, a toxin, an apoptotic peptide, a radionuclide, a viral particle, a gene or an imaging compound, formed through genetic fusion or chemical coupling. A non-limiting list of cytokines used in the conjugate of the present invention is TNFα, TNFβ, IFNα, IFNβ, IFNγ, IL-1, 2, 4, 6, 7, 12, 15, EMAP II, vascular endothelial growth factor (VEGF), PDGF, PD-ECGF or a chemokine.

Conjugates include fusion proteins in which the peptide or targeting moiety is linked to an agent via its polypeptide backbone through genetic expression of a DNA molecule encoding these proteins, directly synthesised proteins and coupled proteins in which pre-formed sequences are associated by a cross-linking agent. The term is also used herein to include associations, such as aggregates.

The peptide or targeting moiety can be coupled directly to the agent or indirectly through a spacer, which can be a single amino acid (e.g., G (glycine)), an amino acid sequence or an organic residue, such as 6-aminocapryl-N-hydroxysuccinimide.

In one embodiment the peptide or targeting moiety is linked to the cytokine N-terminus or C-terminus thus minimising any interference in the binding of the modified cytokine to its receptor. Alternatively, the peptide or targeting moiety can be linked to amino acid residues which are amido- or carboxylic-bond acceptors, which may be naturally occurring on the molecule or artificially inserted using genetic engineering techniques.

In one embodiment, the peptide ligand preferably is linked to the cytokine N-terminus or C-terminus thus minimizing any interference in the binding of the modified cytokine to its receptor. Alternatively, the peptide can be linked to amino acid residues which are amido- or carboxylic-bonds acceptors, naturally occurring on the molecule or artificially inserted with genetic engineering techniques. The modified cytokine is preferably prepared by use of a cDNA comprising a 5'-contiguous sequence encoding the peptide.

According to a preferred embodiment, there is provided a conjugation product between TNF and the CDGRC (SEQ ID NO: 23), CisoDGRC (SEQ ID NO: 59), $C_L$isoDGRC (SEQ ID NO: 59) or $C_D$DGRC peptide. Preferably the amino-terminal of TNF is linked to the peptide, preferably through a spacer. Preferably the spacer is G (glycine).

According to another preferred embodiment, there is provided a conjugation product between IFNγ and the CDGRC (SEQ ID NO: 23), CisoDGRC (SEQ ID NO: 59), $C_L$iso DGRC SEQ ID NO: 59) or $C_D$DGRC peptide. Preferably the amino-terminal of TNF is linked to the peptide, preferably through a spacer. Preferably the spacer is G (glycine).

According to another preferred embodiment, there is provided a conjugation product between IL-12 and the CDGRC (SEQ ID NO: 23), CisoDGRC (SEQ ID NO: 59), $C_L$iso DGRC (SEQ ID NO: 59) or $C_D$DGRC peptide.

Preferably the amino-terminal of TNF is linked to the peptide, preferably through a spacer. Preferably the spacer is G (glycine).

The therapeutic index of the TNF/DGR conjugates can be further improved by using a mutant form of TNF capable of selectively binding to one of the two TNF receptors, p75TNFR and p55TNFR. Said TNF mutant can be obtained by site-directed mutagenesis (Loetscher et al., 1993, Van Ostade et al., 1993).

The pharmacokinetic of the modified cytokines according to the invention can be improved by preparing polyethylene glycol derivatives, which allow to extend the plasmatic half-life of the cytokines themselves.

Bifunctional Derivatives

A further embodiment of the invention is provided by bifunctional derivatives in which peptides or conjugates of the invention are conjugated with antibodies, or their fragments, against tumoral antigens or other tumor angiogenic markers, e.g. αv integrins, metalloproteases or the vascular growth factor, or antibodies or fragments thereof directed against components of the extracellular matrix, such as anti-tenascin antibodies or anti-fibronectin EDB domain. The preparation of a fusion product between TNF and the hinge region of a mAb against the tumor-associated TAG72 antigen expressed by gastric and ovarian adenocarcinoma has recently been reported (Yang et al., 1995).

A further embodiment of the invention is provided by the tumoral pre-targeting with the biotin/avidin system. According to this approach, a ternary complex is obtained on the tumoral antigenic site, at different stages, which is formed by 1) biotinylated mAb, 2) avidin (or streptavidin) and 3) a peptide or conjugate of the invention and biotin. A number of papers proved that the pre-targeting approach, compared with conventional targeting with immunoconjugates, can actually increase the ratio of active molecule homed at the target to free active molecule, thus reducing the treatment toxicity (Colombo et al., 1993; Modorati et al., 1994; Paganelli et al., 1995, 1991). This approach produced favorable results with biotinylated TNF, which was capable of inducing cytotoxicity in vitro and decreasing the tumor cells growth under conditions in which normal TNF was inactive (Moro et al., 1997; Gasparri et al., 1999). The pre-targeting approach can also be carried out with a two-phase procedure by using a bispecific antibody which at the same time binds the tumoral antigen and the modified cytokine. The use of a bispecific antibody directed against a carcinoembryonic antigen and TNF has recently been described as a means for TNF tumoral pre-targeting (Robert et al., 1996).

According to a further embodiment, the invention comprises a TNF molecule conjugated to both a peptide of the invention (e.g., peptide comprising DGR) and an antibody, or a fragment thereof (directly or indirectly via a biotin-avidin bridge), on different TNF subunits, where the antibody or its fragments are directed against an antigen expressed on tumor cells or other components of the tumor stroma, e.g. tenascin and fibronectin EDB domain. This results in a further improvement of the tumor homing properties of the modified cytokine and in the slow release of the latter in the tumor microenvironment through trimer-monomer-trimer transitions. As shown in previous works, in fact, the modified subunits of TNF conjugates can dissociate from the targeting complexes and reassociate so as to form unmodified trimeric TNF molecules, which then diffuse in the tumor microenvironment. The release of bioactive TNF has been shown to occur within 24-48 hours after targeting (Corti et al., 1998).

Extracellular Matrix

The term "extracellular matrix component" (ECM), as used herein, means a molecule that occupies the extracellular spaces of tissues.

In one embodiment the ECM component is selected from fibronectin, vitronectin, collagen or laminin. Preferred ECM components are the $FN-I_5$, $FN-I_7$, $FN-II_1$ or $FN-III_9$ modules of fibronectin, or fragments thereof. Preferably the fragments comprise the NGR motif, or, following deamidation, the DGR motif.

Preferred components of the ECM according to the present invention are those which show modified properties, such as increased endothelial cell adhesion and/or increased integrin (e.g., αvβ3) binding following deamidation of asparagine residues. Particularly preferred ECM components are those that comprise an NGR motif that undergoes deamidation to DGR, preferably $_L$iso DGR or $_D$DGR.

Cytokines

Drug penetration into neoplastic cells is critical for the effectiveness of solid-tumor chemotherapy. To reach cancer cells in solid tumors, chemotherapeutic drugs must enter the drug blood vessels, cross the vessel wall and finally migrate through the interstitium. Heterogeneous tumor perfusion, vascular permeability and cell density, and increased interstitial pressure may represent critical barriers that may limit the penetration of drugs into neoplastic cells and, consequently, the effectiveness of chemotherapy. Cytokines which have the effect of affecting these factors are therefore useful in the present invention. A non-limiting list of cytokines which may be used in the present invention is: TNFα, TNFβ, IFNα, IFNβ, IFNγ, IL-1, 2, 4, 6, 7, 12, 15, IP-10, EMAP II, vascular endothelial growth factor (VEGF), PDGF, PD-ECGF or a chemokine.

TNF

TNF acts as an inflammatory cytokine and has the effect of inducing alteration of the endothelial barrier function, reducing of tumor interstitial pressure, and increasing chemotherapeutic drug penetration and tumor vessel damage.

The first suggestion that a tumor necrotizing molecule existed was made when it was observed that cancer patients occasionally showed spontaneous regression of their tumors following bacterial infections. Subsequent studies in the 1960s indicated that host-associated (or endogenous) mediators, manufactured in response to bacterial products, were likely responsible for the observed effects. In 1975 it was shown that a bacterially-induced circulating factor had strong anti-tumor activity against tumors implanted in the skin in mice. This factor, designated tumor necrosis factor (TNF), was subsequently isolated, cloned, and found to be the prototype of a family of molecules that are involved with immune regulation and inflammation. The receptors for TNF and the other members of the TNF superfamily also constitute a superfamily of related proteins.

TNF-related ligands usually share a number of common features. These features do not include a high degree of overall amino acid (aa) sequence homology. With the exception of nerve growth factor (NGF) and TNF-beta, all ligands are synthesised as type II transmembrane proteins (extracellular C-terminus) that contain a short cytoplasmic segment (10-80 aa residues) and a relatively long extracellular region (140-215 aa residues). NGF, which is structurally unrelated to TNF, is included in this superfamily only because of its ability to bind to the TNFRSF low affinity NGF receptor (LNGFR). NGF has a classic signal sequence peptide and is secreted. TNF-β, in contrast, although also fully secreted, has a primary structure much more related to type II transmembrane proteins. TNF-β might be considered as a type II protein with a non-functional, or inefficient, transmembrane segment. In general, TNFSF members form trimeric structures, and their monomers are composed of beta-strands that orient themselves into a two sheet structure. As a consequence of the trimeric structure of these molecules, it is suggested that the ligands and receptors of the TNSF and TNFRSF superfamilies undergo "clustering" during signal transduction.

TNF-α Human TNF-α is a 233 aa residue, nonglycosylated polypeptide that exists as either a transmembrane or soluble protein. When expressed as a 26 kDa membrane bound protein, TNF-α consists of a 29 aa residue cytoplasmic domain, a 28 aa residue transmembrane segment, and a 176 aa residue extracellular region. The soluble protein is created by a proteolytic cleavage event via an 85 kDa TNF-alpha converting enzyme (TACE), which generates a 17 kDa, 157 aa residue molecule that normally circulates as a homotrimer.

TNF-β/LT-α: TNF-β, otherwise known as lymphotoxin-α (LT-α) is a molecule whose cloning was contemporary with that of TNF-α. Although TNF-β circulates as a 171 aa residue, 25 kDa glycosylated polypeptide, a larger form has been found that is 194 aa residues long. The human TNF-β cDNA codes for an open reading frame of 205 aa residues (202 in the mouse), and presumably some type of proteolytic processing occurs during secretion. As with TNF-α, circulating TNF-β exists as a non-covalently linked trimer and is known to bind to the same receptors as TNF-α.

In one embodiment the TNF is a mutant form of TNF capable of selectively binding to one of the TNF receptors (Loetscher H et al (1993) J Biol Chem 268:26350-7; Van Ostade X et al (1993) Nature 361:266-9).

The maximum tolerated dose of bolus TNF in humans is 218-410 μg/m² (Fraker et al., 1995) about 10-fold lower than the effective dose in animals. Based on data from murine models it is believed that an at least 10 times higher dose is necessary to achieve anti-tumor effects in humans (Schraffordt Koops et al., 1998). In the first clinical study on hyperthermic isolated-limb perfusion, high response rates were obtained with the unique dose of 4 mg of TNF in combination with melphalan and interferon γ (Lienard et al., 1992). Other works showed that interferon γ can be omitted and that even lower doses of TNF can be sufficient to induce a therapeutic response (Hill et al., 1993; Eggermont et al., 1996). As the two cytokines exert synergistic effects on endothelial cells, their combined, selective targeting thereon is likely to result in stronger anti-tumor activity thus allowing to overcome the problems of systemic toxicity usually encountered in cancer therapy with the same cytokines used in combination. Furthermore, it is known that TNF can decrease the barrier function of the endothelial lining vessels, thus increasing their permeability to macromolecules. Taking advantage of the lower toxicity of treatment with the modified TNF molecules according to the invention, and of their tumor vessels homing properties, an alternative application is their use to increase the permeability of tumor vessels to other compounds, either for therapeutic or diagnostic purposes. For instance the modified TNF can be used to increase the tumor uptake of radiolabelled antibodies or hormones (tumor-imaging compounds) in radioimmunoscintigraphy or radioimmunotherapy of tumors. Alternatively, the uptake of chemotherapeutic drugs, immunotoxins, liposomes carrying drugs or genes, or other anticancer drugs could also be increased, so that their antitumor effects are enhanced.

Many other inflammatory cytokines also have the property of increasing endothelial vessel permeability, and it will be appreciated that the invention can be applied to such cytokines, together with agents which increase expression of such cytokines. Inflammatory cytokines, also known as pro-inflammatory cytokines, are a number of polypeptides and glycoproteins with molecular weights between 5 kDa and 70 kDa. They have a stimulating effect on the inflammatory response. The most important inflammatory cytokines are TNF, IL-1, IL-6 and IL-8.

A Table of some cytokines classified as inflammatory cytokines is shown below:

| Inflammatory Cytokines | |
|---|---|
| Group | Individual cytokines |
| Endogenous cytokines | IL-1, TNF-α, IL-6 |
| Up-regulation | IL-1, TNF-α, IL-6, IFN-α, INF-β, chemokines |
| Stimulation of the production of acute phase reactants | IL-1, IL-6, IL-11, TNF-α, INF-γ, TGF-β, LIF, OSM, CNTF |
| Chemoattractant cytokines | |
| CXC chemokines | IL-8, PF-4, PBP, NAP-2, β-TG |
| CC chemokines | MIP-1α, MIP-1β, MCP-1, MCP-2, MCP-3, RANTES |
| C chemokines | Lymphotactin |
| Stimulation of inflammatory cytokines | IL-12 |

TGF-β: transforming growth factor, LIF: leukemia inhibitory factor; OSM: oncostatin M; CNTF: ciliary neurotrophic factor; PF-4: platelet factor 4; PBP: platelet basic protein; NAP-2: neutrophil activating protein 2; β-TG: β-thromboglobulin; MIP: macrophage inflammatory protein; MCP: monocyte chemoattractant protein.

The up-regulation of inflammatory response is also performed by IL-11, IFN-α, IFN-β, and especially by the members of the chemokine superfamily. TGF-β in some situations has a number of inflammatory activities including chemoattractant effects on neutrophils, T lymphocytes and inactivated monocytes.

IFN-γ

A large body of evidence suggests that interferon-γ (IFNγ), a pleiotropic cytokine mainly produced by T-lymphocytes and natural killer cells (Farrar, et al., 1993; Boehm et al., 1997) can promote anti-tumor responses (Curnis et al., 2005). For instance, IFNγ can induce anti-proliferative and pro-apoptotic effects on many tumor cell types, can inhibit tumor angiogenesis and activate natural killer cells and macrophages to kill a variety of tumor cell targets. IFNγ is also an important regulator of CD4+ T helper cells, is the major physiological macrophage-activating factor and can augment the expression of MHC-I and II on cancer and endothelial cells. Within tumor stroma IFNγ can induce cytokine and chemokine secretion, including IP-10 (IFN-inducible Protein 10), an angiostatic protein and a chemoattractant factor for lymphocytes and monocytes. Evidence has been obtained to suggest that IFNγ produced by tumor-infiltrating macrophages plays a role in tumor blood vessel destruction. Combined treatment of endothelial cells with IFNγ and tumor necrosis factor-α (TNF) results in synergistic cytotoxic effects, likely important for tumor vasculature destruction. IFNγ can also increase the production of TNF by activated macrophages, as well as the expression of TNF-receptors in various cell types. As a consequence of these effects on tumor vasculature and on cells of the immune system IFNγ can activate inflammatory/immune responses against established tumors and inhibit tumor growth.

IFNγ exists as a homodimer of two noncovalently bound polypeptide subunits. The primary sequence of wildtype human IFNγ (huIFNG) was reported by Gray et al., 1982; Taya et al., 1982; Devos et al., 1982; and Rinderknecht et al., 1984, and in EP 77670, EP 89676 and EP 110044. The 3D structure of huIFNG was reported by Ealick et al., 1991.

IL-12

Interleukin 12 (IL-12), also referred to as natural killer cell stimulatory factor ("NKSF") or cytotoxic lymphocyte maturation factor ("CLMF"), is a potent immunoregulatory molecule that plays a role in a wide range of diseases. Human IL-12 has been characterized as a cytokine with a unique structure and pleiotropic effects (Kobayashi, et al., 1989; Seder, et al., 1993; Ling, et al., 1995; Podlaski, et al., 1992). IL-112 plays a critical role in the pathology associated with several diseases involving immune and inflammatory responses. A review of IL-12, its biological activities, and its role in disease can be found in Gately et al., 1998. An important role of IL-12 in vivo is its ability to induce IFNγ production by both natural killer (NK) and T cells.

Structurally, IL-12 is a heterodimeric protein comprising a 35 kDa subunit (p35) and a 40 kDa subunit (p40) which are both linked together by a disulfide bridge (referred to as the "p70 subunit"). The heterodimeric protein is produced primarily by antigen-presenting cells such as monocytes, macrophages and dendritic cells. These cell types also secrete an excess of the p40 subunit relative to p70 subunit.

IL-2

Because of the central role of the IL-2/IL-2R system in mediation of the immune and inflammatory responses, it is obvious that monitoring and manipulation of this system has important diagnostic and therapeutic implications. IL-2 has shown promise as an anti-cancer drug by virtue of its ability to stimulate the proliferation and activities of tumor-attacking LAK and TIL (tumor-infiltrating lymphocytes) cells. However, problems with IL-2 toxicity are still of concern and merit investigation. The present invention addresses this problem.

IL-15

Interleukin 15 (IL-15) is a novel cytokine that shares many biological properties with, but lacks amino acid sequence homology to, IL-2. IL-15 was originally identified in media conditioned by a monkey kidney epithelial cell line (CVI/EBNA) based on its mitogenic activity on the murine T cell line, CTLL-2. IL-15 was also independently discovered as a cytokine produced by a human adult T cell leukemia cell line (HuT-102) that stimulated T cell proliferation and was designated IL-T. By virtue of its activity as a stimulator of T cells, NK cells, LAK cells, and TILs, IL-2 is currently in clinical trials testing its potential use in treatments for cancer and for viral infections. Because of its similar biological activities, IL-15 should have similar therapeutic potential.

Chemokines

Chemokines are a superfamily of mostly small, secreted proteins that function in leukocyte trafficking, recruiting, and recirculation. They also play a critical role in many pathophysiological processes such as allergic responses, infectious and autoimmune diseases, angiogenesis, inflammation, tumor growth, and hematopoietic development. Approximately 80 percent of these proteins have from 66 to 78 amino acids (aa) in their mature form. The remainder are larger with additional aa occurring upstream of the protein core or as part of an extended C-terminal segment. All chemokines signal through seven transmembrane domain G-protein coupled receptors. There are at least seventeen known chemokine receptors, and many of these receptors exhibit promiscuous binding properties whereby several different chemokines can signal through the same receptor.

Chemokines are divided into subfamilies based on conserved aa sequence motifs. Most family members have at least four conserved cysteine residues that form two intramolecular disulfide bonds. The subfamilies are defined by the position of the first two cysteine residues:

The alpha subfamily, also called the CXC chemokines, have one aa separating the first two cysteine residues. This group can be further subdivided based on the presence or absence of a glu-leu-arg (ELR) aa motif immediately preceding the first cysteine residue. There are currently five CXC-specific receptors and they are designated CXCR1 to CXCR5. The ELR$^+$ chemokines bind to CXCR2 and generally act as neutrophil chemoattractants and activators. The ELR− chemokines bind CXCR3 to −5 and act primarily on lymphocytes. At the time of this writing, 14 different human genes encoding CXC chemokines have been reported in the scientific literature with some additional diversity contributed by alternative splicing.

In the beta subfamily, also called the CC chemokines, the first two cysteines are adjacent to one another with no intervening aa. There are currently 24 distinct human beta subfamily members. The receptors for this group are designated CCR1 to CCR11. Target cells for different CC family members include most types of leukocytes.

There are two known proteins with chemokine homology that fall outside of the alpha and beta subfamilies. Lymphotactin is the lone member of the gamma class (C chemokine) which has lost the first and third cysteines. The lymphotactin receptor is designated XCR1. Fractalkine, the only known member of the delta class ($CX_3C$ chemokine), has three intervening aa between the first two cysteine residues. This molecule is unique among chemokines in that it is a transmembrane protein with the N-terminal chemokine domain fused to a long mucin-like stalk. The fractalkine receptor is known as $CX_3CR1$.

VEGF

The present invention is also applicable to Vasculature Endothelial Growth Factor (VEGF). Angiogenesis is a process of new blood vessel development from pre-existing vasculature. It plays an essential role in embryonic development, normal growth of tissues, wound healing, the female reproductive cycle (i.e., ovulation, menstruation and placental development), as well as a major role in many diseases. Particular interest has focused on cancer, since tumors cannot grow beyond a few millimeters in size without developing a new blood supply. Angiogenesis is also necessary for the spread and growth of tumor cell metastases.

One of the most important growth and survival factors for endothelium is VEGF. VEGF induces angiogenesis and endothelial cell proliferation and it plays an important role in regulating vasculogenesis. VEGF is a heparin-binding glycoprotein that is secreted as a homodimer of 45 kDa. Most types of cells, but usually not endothelial cells themselves, secrete VEGF. Since the initially discovered VEGF, VEGF-A, increases vascular permeability, it was known as vascular permeability factor. In addition, VEGF causes vasodilatation, partly through stimulation of nitric oxide synthase in endothelial cells. VEGF can also stimulate cell migration and inhibit apoptosis. There are several splice variants of VEGF-A. The major ones include: 121, 165, 189 and 206 amino acids (aa), each one comprising a specific exon addition.

EMAP II

Endothelial-Monocyte Activating Polypeptide-II (EMAP-II) is a cytokine that is an antiangiogenic factor in tumor vascular development, and strongly inhibits tumor growth. Recombinant human EMAP-II is an 18.3 kDa protein containing 166 amino acid residues. EMAP II has also been found to increase endothelial vessel permeability.

PDGF

It has also been proposed that platelet-derived growth factor (PDGF) antagonists might increase drug-uptake and therapeutic effects of a broad range of anti-tumor agents in common solid tumors. PDGF is a cytokine of 30 kDA and is released by platelets on wounding and stimulates nearby cells to grow and repair the wound.

PD-ECGF

As its name suggests, platelet-derived endothelial cell growth factor (PD-ECGF) was originally isolated from platelets based on its ability to induce mitosis in endothelial cells. Its related protein is gliostatin.

Antibodies

As used herein, an "antibody" refers to a protein consisting of one or more polypeptides substantially encoded by immunoglobulin genes or fragments of immunoglobulin genes. Antibodies may exist as intact immunoglobulins or as a number of fragments, including those well-characterised fragments produced by digestion with various peptidases. While various antibody fragments are defined in terms of the digestion of an intact antibody, one of skill will appreciate that antibody fragments may be synthesised de novo either chemically or by utilising recombinant DNA methodology. Thus, the term antibody, as used herein also includes antibody fragments either produced by the modification of whole antibodies or synthesised de novo using recombinant DNA methodologies. Antibody fragments encompassed by the use of the term "antibodies" include, but are not limited to, Fab, Fab', F(ab') 2, scFv, Fv, dsFv diabody, and Fd fragments.

The invention also provides monoclonal or polyclonal antibodies to the surface proteins. Thus, the present invention further provides a process for the production of monoclonal or polyclonal antibodies to polypeptides of the invention.

If polyclonal antibodies are desired, a selected mammal (e.g., mouse, rabbit, goat, horse, etc.) is immunised with an immunogenic polypeptide bearing an epitope(s). Serum from the immunised animal is collected and treated according to known procedures. If serum containing polyclonal antibodies to an epitope contains antibodies to other antigens, the polyclonal antibodies can be purified by immunoaffinity chromatography. Techniques for producing and processing polyclonal antisera are known in the art. In order that such antibodies may be made, the invention also provides polypeptides of the invention or fragments thereof haptenised to another polypeptide for use as immunogens in animals or humans.

Monoclonal antibodies directed against binding cell surface epitopes in the polypeptides can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against epitopes can be screened for various properties; i.e., for isotype and epitope affinity.

An alternative technique involves screening phage display libraries where, for example the phage express scFv fragments on the surface of their coat with a large variety of complementarity determining regions (CDRs). This technique is well known in the art.

For the purposes of this invention, the term "antibody", unless specified to the contrary, includes fragments of whole antibodies which retain their binding activity for a target antigen. As mentioned above such fragments include Fv, F(ab') and F(ab')$_2$ fragments, as well as single chain antibodies (scFv). Furthermore, the antibodies and fragments thereof may be humanised antibodies, for example as described in EP-A-239400.

Agent

As used herein, the term "agent" includes, but is not limited to, a compound, such as a test compound, which may be obtainable from or produced by any suitable source, whether natural or not. The agent may be designed or obtained from a library of compounds which may comprise peptides, as well as other compounds, such as small organic molecules and particularly new lead compounds. By way of example, the agent may be a natural substance, a biological macromolecule, or an extract made from biological materials such as bacteria, fungi, or animal (particularly mammalian) cells or tissues, an organic or an inorganic molecule, a synthetic test compound, a semi-synthetic test compound, a structural or functional mimetic, a peptide, a peptidomimetics, a derivatised test compound, a peptide cleaved from a whole protein, or a peptides synthesised synthetically (such as, by way of example, either using a peptide synthesizer) or by recombinant techniques or combinations thereof, a recombinant test compound, a natural or a non-natural test compound, a fusion protein or equivalent thereof and mutants, derivatives or combinations thereof.

The agent can be an amino acid sequence or a chemical derivative thereof. The substance may even be an organic compound or other chemical. The agent may even be a nucleotide sequence—which may be a sense sequence or an antisense sequence.

Pharmaceutical Formulations

The present invention also provides a pharmaceutical composition for treating an individual wherein the composition comprises a therapeutically effective amount of a peptide, polynucleotide, conjugate and drug combinations of the present invention.

A composition of the present invention comprising a peptide or conjugate comprising an isoDGR motif is substantially free of peptides or conjugates comprising other forms of DGR. By substantially free, it is meant the w/w % of isoDGR containing peptide or conjugate (i.e., peptide or conjugate wherein the DGR motif is all in the isoDGR form) present in the composition relative to total DGR containing peptide or conjugate (i.e. in all isomeric forms) present in the composition is greater than 50%, more preferably greater than 55% more preferably greater than 60%, more preferably greater than 65%, more preferably greater than 70%, more preferably greater than 75%, more preferably greater than 80%, more preferably greater than 85%, more preferably greater than 90%, more preferably greater than 95%, more preferably greater than 97%, more preferably greater than 99%.

A composition of the present invention comprising a peptide or conjugate comprising an $_L$isoDGR motif is substantially free of peptides or conjugates comprising other forms of DGR. By substantially free, it is meant the w/w % of the $_L$isoDGR containing peptide or conjugate (i.e., peptide or conjugate wherein the DGR motif is all in the $_L$isoDGR form) present in the composition relative to total DGR containing peptide or conjugate (i.e. in all isomeric forms) present in the composition is greater than 50%, more preferably greater than 55%, more preferably greater than 60% more preferably greater than 65%, more preferably greater than 70%, more preferably greater than 75%, more preferably greater than 80%, more preferably greater than 85%, more preferably greater than 90%, more preferably greater than 95%, more preferably greater than 97%, more preferably greater than 99%.

A composition of the present invention comprising a peptide or conjugate comprising a $_D$DGR motif is substantially free of peptides or conjugates comprising other forms of DGR. By substantially free, it is meant the w/w % of the $_D$DGR containing peptide or conjugate (i.e., peptide or conjugate wherein the DGR motif is all in the $_D$DGR form) present in the composition relative to total DGR containing peptide or conjugate (i.e. in all isomeric forms) present in the composition is greater than 50%, more preferably greater than 55%, more preferably greater than 60% more preferably greater than 65%, more preferably greater than 70%, more preferably greater than 75%, more preferably greater than 80%, more preferably greater than 85%, more preferably greater than 90%, more preferably greater than 95%, more preferably greater than 97%, more preferably greater than 99%.

The pharmaceutical composition may be for human or animal usage. Typically, a physician will determine the actual dosage which will be most suitable for an individual subject and it will vary with the age, weight and response of the particular individual.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s), and other carrier agents that may aid or increase the viral entry into the target site (such as for example a lipid delivery system). Suitable carriers and diluents include isotonic saline solutions, for example phosphate-buffered saline. Details of excipients may be found in The Handbook of Pharmaceutical Excipients, 2nd Edn, Eds Wade & Weller, American Pharmaceutical Association.

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Formulations for oral or parenteral administration are preferred. Formulations for parenteral administration comprise injectable solutions or suspensions and liquids for infusions. For the preparation of the parenteral forms, an effective amount of the active ingredient will be dissolved or suspended in a sterile carrier, optionally adding excipients such as solubilizers, isotonicity agents, preservatives, stabilizers, emulsifiers or dispersing agents, and it will be subsequently distributed in sealed vials or ampoules.

The composition may be formulated such that administration daily, weekly or monthly will provide the desired daily dosage. It will be appreciated that the composition may be conveniently formulated for administrated less frequently, such as every 2, 4, 6, 8, 10 or 12 hours.

Polynucleotides/vectors encoding polypeptide components may be administered directly as a naked nucleic acid construct, preferably further comprising flanking sequences homologous to the host cell genome.

Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example Lipofectam™ and Transfectam™). Typically, nucleic acid constructs are mixed with the transfection agent to produce a composition.

Preferably the polynucleotide or vector of the invention is combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular or transdermal administration.

The routes of administration and dosage regimens described are intended only as a guide since a skilled practitioner will be able to determine readily the optimum route of administration and dosage regimens for any particular patient and condition.

The preparation of peptides, and in particular cytokines, in form of liposomes can improve the biological activity thereof. It has, in fact, been observed that acylation of the TNF amino groups induces an increase in its hydrophobicity without loss of biological activity in vitro. Furthermore, it has been reported that TNF bound to lipids has unaffected cytotoxicity in vitro, immunomodulating effects and reduced toxicity in vivo (Deb et al., 1989, 1990).

Preferably compositions of the present invention comprising peptides and conjugates which contain DGR motifs according to the present invention are substantially free of the corresponding peptides and conjugates which contain the corresponding NGR motif. Preferably the proportion of DGR containing peptide relative to the total peptide (i.e., DGR and NGR containing peptide) is more than 60%, more preferably 70%, more preferably 80%, more preferably 85%, more preferably 90%, more preferably 95%, more preferably 97%, more preferably 99% w/w.

Treatment

The peptides, conjugates and compositions of the invention may be used in therapeutic treatment.

It is to be appreciated that all references herein to treatment include curative, palliative and prophylactic treatment.

The patient treated in the present invention in its many embodiments is desirably a human patient, although it is to be understood that the principles of the invention indicate that the invention is effective with respect to all mammals, which are intended to be included in the term "patient". In this context, a mammal is understood to include any mammalian species in which treatment of diseases associated with angiogenesis is desirable, particularly agricultural and domestic mammalian species.

In one embodiment the peptides, conjugates or pharmaceutical compositions may be used to treat or prevent cancer including but not limited to cancer of the lung, pancreas, breast, colon, larynx or ovary. Preferably the cancer comprises a solid tumor.

In another embodiment, the peptides and/or conjugates may be used to treat or prevent diseases involving angiogenisis, such as diseases associated with $\alpha v\beta 3$ expression.

Angiogenesis is a process of tissue vascularization that involves the growth of new developing blood vessels into a tissue, and is also referred to as neo-vascularization. The process is mediated by the infiltration of endothelial cells and smooth muscle cells. The process is believed to proceed in any one of three ways: the vessels can sprout from pre-existing vessels, de-novo development of vessels can arise from precursor cells (vasculogenesis), or existing small vessels can enlarge in diameter (Blood et al., 1990).

There are a variety of diseases in which angiogenesis is believed to be important, referred to as angiogenic diseases, including but not limited to, inflammatory disorders such as immune and non-immune inflammation, arthritis, disorders associated with inappropriate or inopportune invasion of vessels such as diabetic retinopathy, macular degeneration, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma and the like which require neovascularization to support tumor growth.

Thus, methods which inhibit angiogenesis in a diseased tissue ameliorates symptoms of the disease and, depending upon the disease, can contribute to cure of the disease.

In another related embodiment, a tissue to be treated is a retinal tissue of a patient with diabetic retinopathy, macular degeneration or neovascular glaucoma and the angiogenesis to be inhibited is retinal tissue angiogenesis where there is neovascularization of retinal tissue.

In an additional related embodiment, a tissue to be treated is a tumor tissue of a patient with a solid tumor, a metastases, a skin cancer, a breast cancer, a hemangioma or angiofibroma and the like cancer, and the angiogenesis to be inhibited is tumor tissue angiogenesis where there is neovascularization of a tumor tissue. Typical solid tumor tissues treatable by the present methods include lung, pancreas, breast, colon, laryngeal, ovarian, and the like tissues. Exemplary tumor tissue angiogenesis, and inhibition thereof, is described in the Examples.

Inhibition of tumor tissue angiogenesis is a particularly preferred embodiment because of the important role neovascularization plays in tumor growth. In the absence of neovascularization of tumor tissue, the tumor tissue does not obtain the required nutrients, slows in growth, ceases additional growth, regresses and ultimately becomes necrotic resulting in killing of the tumor.

The methods are also particularly effective against the formation of metastases because (1) their formation requires vascularization of a primary tumor so that the metastatic cancer cells can exit the primary tumor and (2) their establishment in a secondary site requires neovascularization to support growth of the metastases.

In a related embodiment, the invention contemplates the practice of the method in conjunction with other therapies such as conventional chemotherapy directed against solid tumors and for control of establishment of metastases. The administration of angiogenesis inhibitor is typically conducted during or after chemotherapy, although it is preferably to inhibit angiogenesis after a regimen of chemotherapy at times where the tumor tissue will be responding to the toxic assault by inducing angiogenesis to recover by the provision of a blood supply and nutrients to the tumor tissue. In addition, it is preferred to administer the angiogenesis inhibition methods after surgery where solid tumors have been removed as a prophylaxis against metastases.

Insofar as the present methods apply to inhibition of tumor neovascularization, the methods can also apply to inhibition of tumor tissue growth, to inhibition of tumor metastases formation, and to regression of established tumors.

Restenosis is a process of smooth muscle cell (SMC) migration and proliferation at the site of percutaneous transluminal coronary angioplasty which hampers the success of angioplasty. The migration and proliferation of SMC's during restenosis can be considered a process of angiogenesis which is inhibited by the present methods. Therefore, the invention also contemplates inhibition of restenosis by inhibiting angiogenesis according to the present methods in a patient following angioplasty procedures.

The peptides, conjugates and pharmaceutical compositions of the invention can be used in combined, separated or sequential preparations, also with other diagnostic or therapeutic substances.

TNF/IFN Combinations

Another aspect of the present invention relates to the use of a combination of the modified TNF, and IFNγ. This combination can be used in combined, separated or sequential preparations. Advantageously the combination is also with other diagnostic or therapeutic substances, in the treatment or in the diagnosis of cancer, such as doxorubicin and mephalan. Thus the present invention provides a pharmaceutical composition comprising a combination of the modified TNF and IFNγ, and optionally another tumor-diagnostic or anti-tumor therapeutic substance. Again, this combination can be used in combined, separated or sequential preparations.

In our International patent publication number WO03/093478, we found targeted delivery of picogram doses of cytokines enhances the penetration of chemotherapeutic drugs, providing a novel and surprising strategy for increasing the therapeutic index of chemotherapeutic drugs. International patent publication number WO03/093478 is hereby incorporated by reference in its entirety. In more detail, we have found that delivery of very low doses of cytokines to tumors and the tumor-associated environment including tumor vasculature represents a new approach to avoiding negative feedback mechanisms and to preserve its ability to alter drug-penetration barriers.

In one embodiment of this aspect of the present invention, a conjugate of the present invention may be administered at a dose of from in the range of 0.5 to 500 ng/kg, preferably in the range of 1 to 50 ng/kg, more preferably in the range of 5 to 15 ng/kg.

In an alternative embodiment of this aspect of the invention there is provided a pharmaceutical composition comprising a conjugate of the present invention in combination with IFNγ, wherein the conjugate is present in an amount such that the conjugate or a metabolite thereof is provided to the blood plasma of the subject to be treated in an amount of no greater than about 35,000 ng/day, preferably about 3,500 ng/day, more preferably about 1,000 ng/day.

The above dosage relate to a dosage for a 70 kg subject. A person skilled in the art would readily be able to modify the recited dosage for a subject having as mass other than 70 kg.

The routes of administration and dosage regimens described are intended only as a guide since a skilled practitioner will be able to determine readily the optimum route of administration and dosage regimens for any particular patient and condition.

(A) The repeats in each fragments and in fibronectin subunit are schematically represented: type I repeats (rectangles); type II repeats (ovals); type III repeats (squares). Modules containing NGR and RGD sequences are indicated (SEQ ID NOS 4, 9, 4 and 8 disclosed, respectively, in order of appearance). Natural fragments obtained by proteolytic digestion with cathepsin (FN-70 KDa) or cathepsin-trypsin (FN-45 and FN-30 KDa) are schematically shown. Retronectin, recombinant FN-I$_{4-5}$ fragment, and synthetic FN-I$_5$ are also represented.

(B) Three dimensional PDB-structure of FN-I$_{4-5}$ (Protein Data Bank code: 1FBR.pdb). The side-chains of the NGR motif (Asn$^{263}$, Gly$^{264}$ and Arg$^{265}$) are shown.

Figure 1:
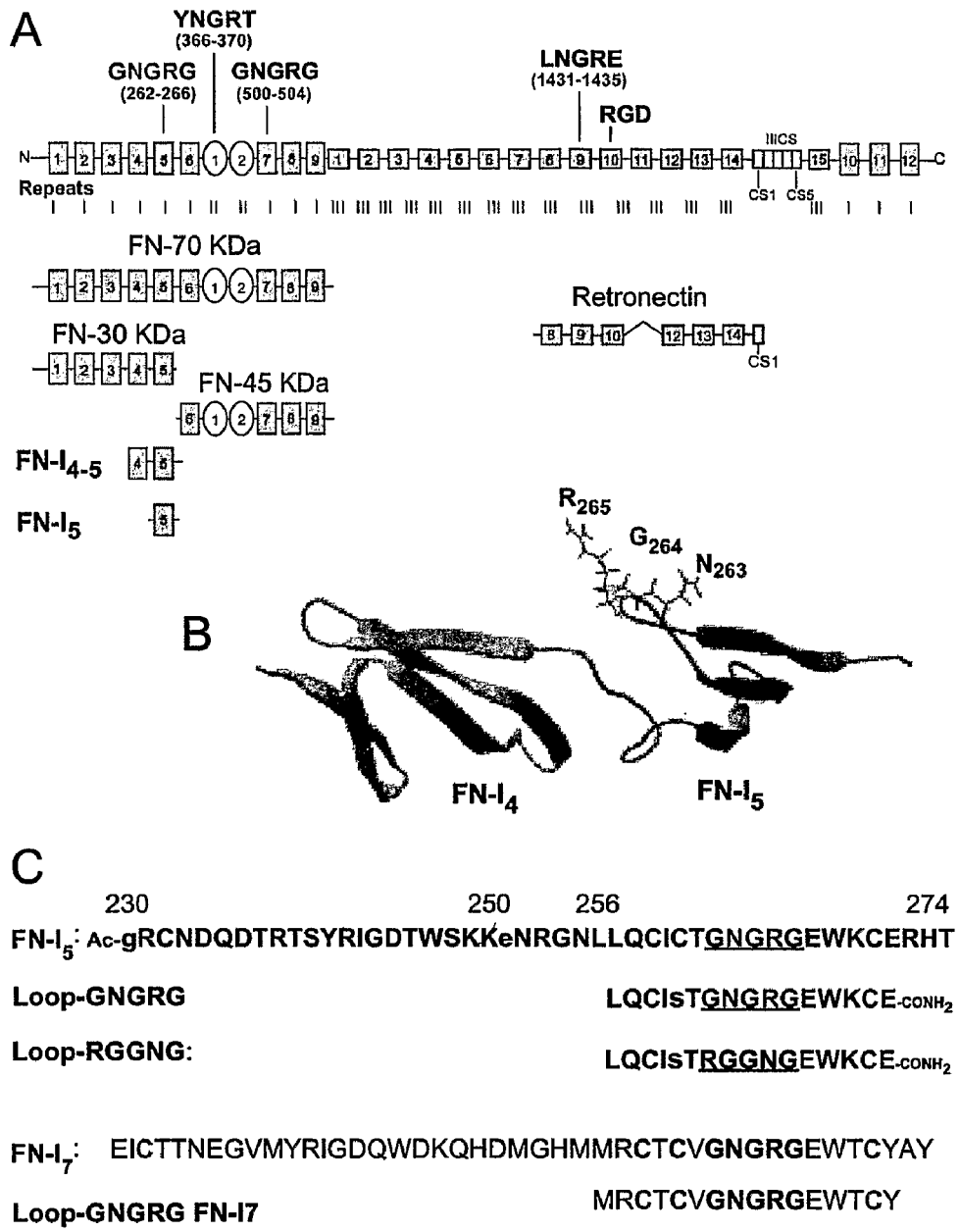
FIGS. 1A-1C. Schematic representation, three-dimensional structure and primary sequence of fibronectin fragments.

(C) Primary sequence of synthetic FN-I$_5$ and Loop-GN-GRG and Loop-RGGNG peptides, and FN-I$_7$ and Loop-GN-GRG peptide (see Methods). The sequences presented in FIG. 1C are, from top to bottom and left to right, SEQ ID NO: 45, SEQ ID NO: 4, SEQ ID NO: 46, SEQ ID NO: 50, SEQ ID NO: 47, SEQ ID NO: 48, SEQ ID NO: 4 and SEQ ID NO: 49.

Figure 2:
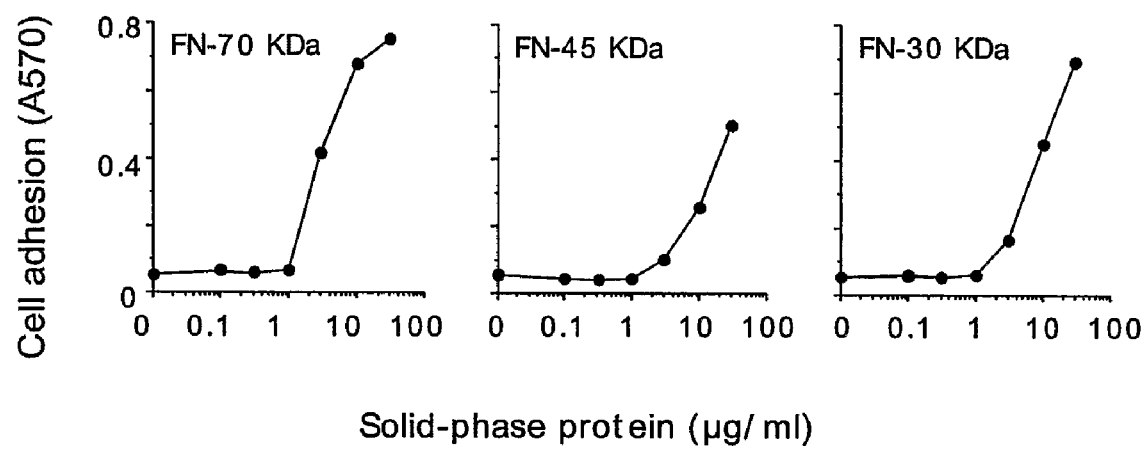

FIG. 2. Cell adhesion promoting properties of natural fibronectin fragments.

Microtiter plates coated with natural proteolytic fragments (FN-70 KDa, FN-45 KDa and FN-30 KDa) promote the adhesion of endothelial EA.hy926 cells.

FIGS. 3A-3D. Accelerated aging of FN fragments increase their pro-adhesive properties.

Adhesion of EA.hy926 cells to microtiter plates coated with various peptides and proteins before and after accelerated aging. Accelerated aging was performed by peptide incubation in 0.1 M ammonium bicarbonate buffer, pH 8.5, for 16 h at 37° C. ("heat-treatment"). Adhesion to: recombinant FN-I$_{4-5}$ or control protein (FN-I$_{4-5}$ (SGS)) (A), synthetic FN-I$_5$ (B), recombinant CNGRC-TNF, CNGRC-TNF$_{1-11}$ and control CARAC-TNF$_{1-11}$ peptide (C), CDGRC-TNF (D). Heat-treated (37° C.) and untreated (−20° C.) products were adsorbed onto the plastic surface of microtiter wells (overnight at 4° C.). Microphotograph of wells coated with 30 μg/ml of heat-treated FN-I$_5$ or BSA (B, right) or with 10 μg/ml of recombinant CNGRC-TNF or CDGRC-TNF (C, right), ×200. Cell adhesion assay was carried out as described in Materials and Methods. The TNF fusion constructs, including the TNF$_{1-11}$ fusion constructs, were made as described Materials and Methods, and include a "G" linker.

Figure 4:
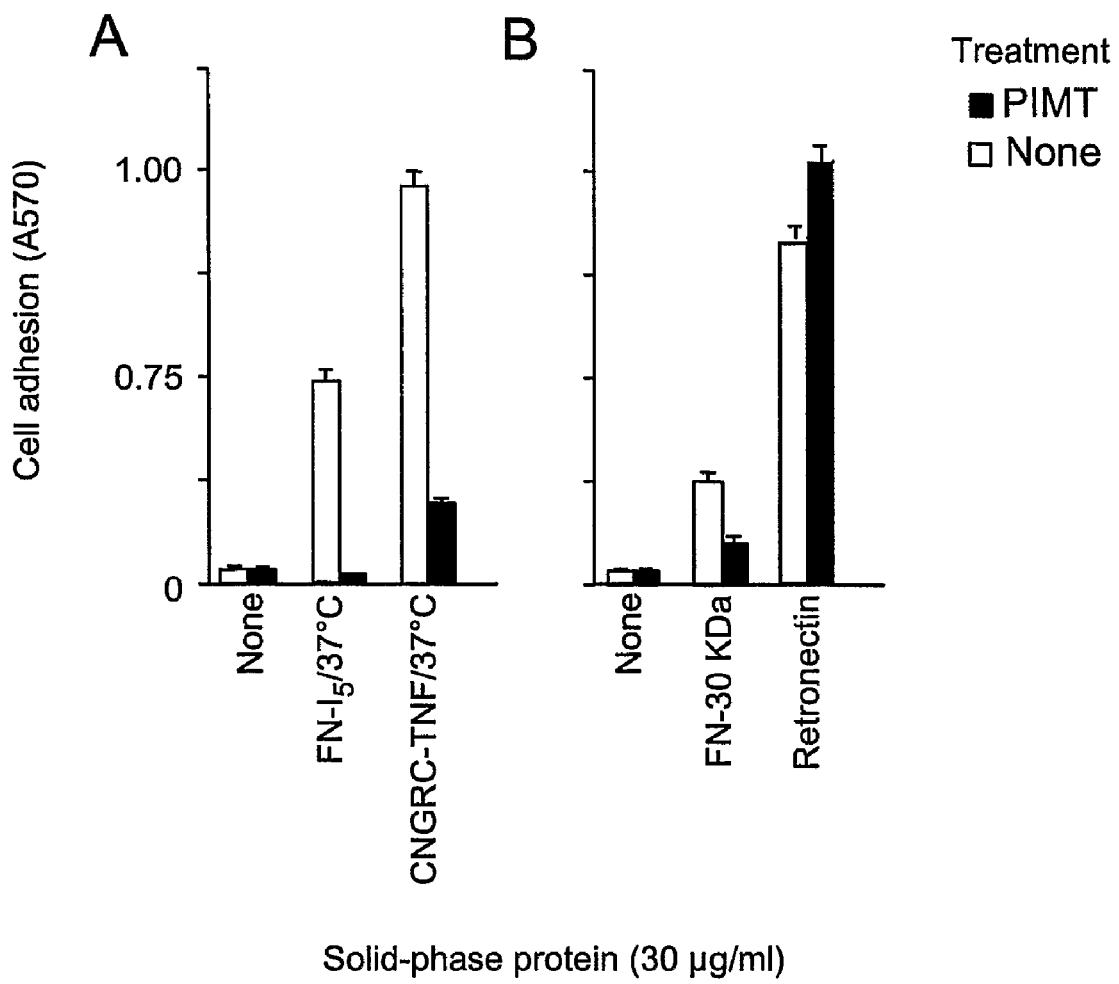

FIG. 4. The pro-adhesive properties of FN fragments are inhibited by PIMT.

Microtiterplates were coated with heat-treated FN-I$_5$ or NGR-TNF (A), or with natural FN-30 KDa, FN-45 KDa or retronectin (RN) (CNGRC disclosed as SEQ ID NO: 6) (B). The adsorbed proteins were then treated with PIMT enzyme for 16 h at 37° C. After incubation the enzyme solution was removed by washing. EA.hy926 cell adhesion assay was then performed as described in Materials and Methods.

Figure 5:
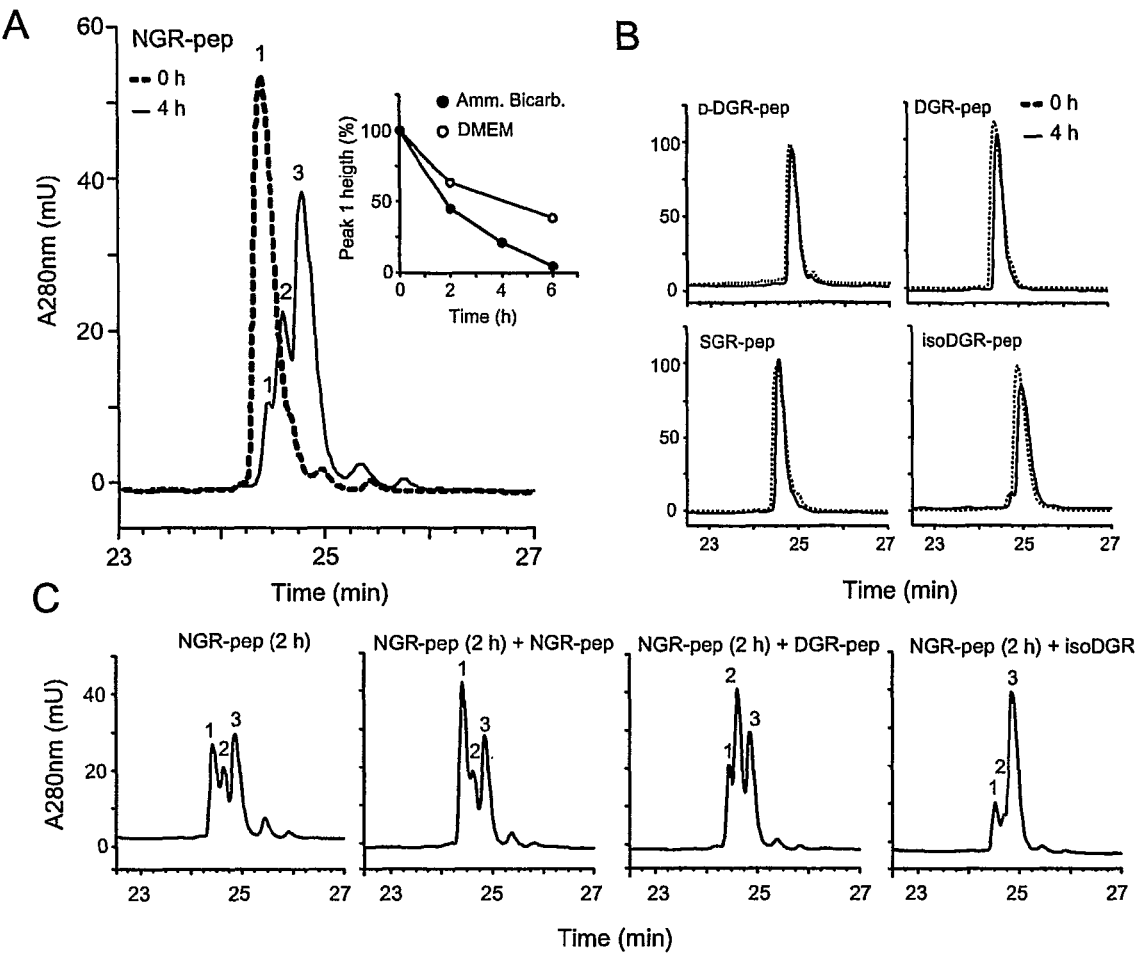

FIG. 5. Stability of NGR, DGR and isoDGR motives.

RP-HPLC analysis of NGR-pep and its synthetic deamidation products (DGR-pep and isoDGR-pep) before and after incubation for 4 h at 37° C. in 0.1 M ammonium bicarbonate buffer, pH 8.5 (A and B) and in DMEM, pH 7.3 (A, inset). RP-HPLC was performed on a C-18 column (PepMap C18, PerSeptive Biosystem) as follows: buffer A, 0.1% trifluoroacetic acid (TFA) in water; buffer B, 95% acetonitrile, 0.1% TFA; 0% B for 10 min, linear gradient 20-40% B in 30 min, 100% B for 10 min; 0% B for 15 min (flow rate, 0.5 ml/min). Peak 1, 2 and 3 were identified by spiking the NGR-pep, after 2 h of incubation, with equal amount of the indicated peptide (C). NGR-pep (peak 1) rapidly converts to compounds corresponding to DGR-pep (peak 2) and isoDGR-pep (peak 3) (half-life, 2-4 h).

Figure 6:
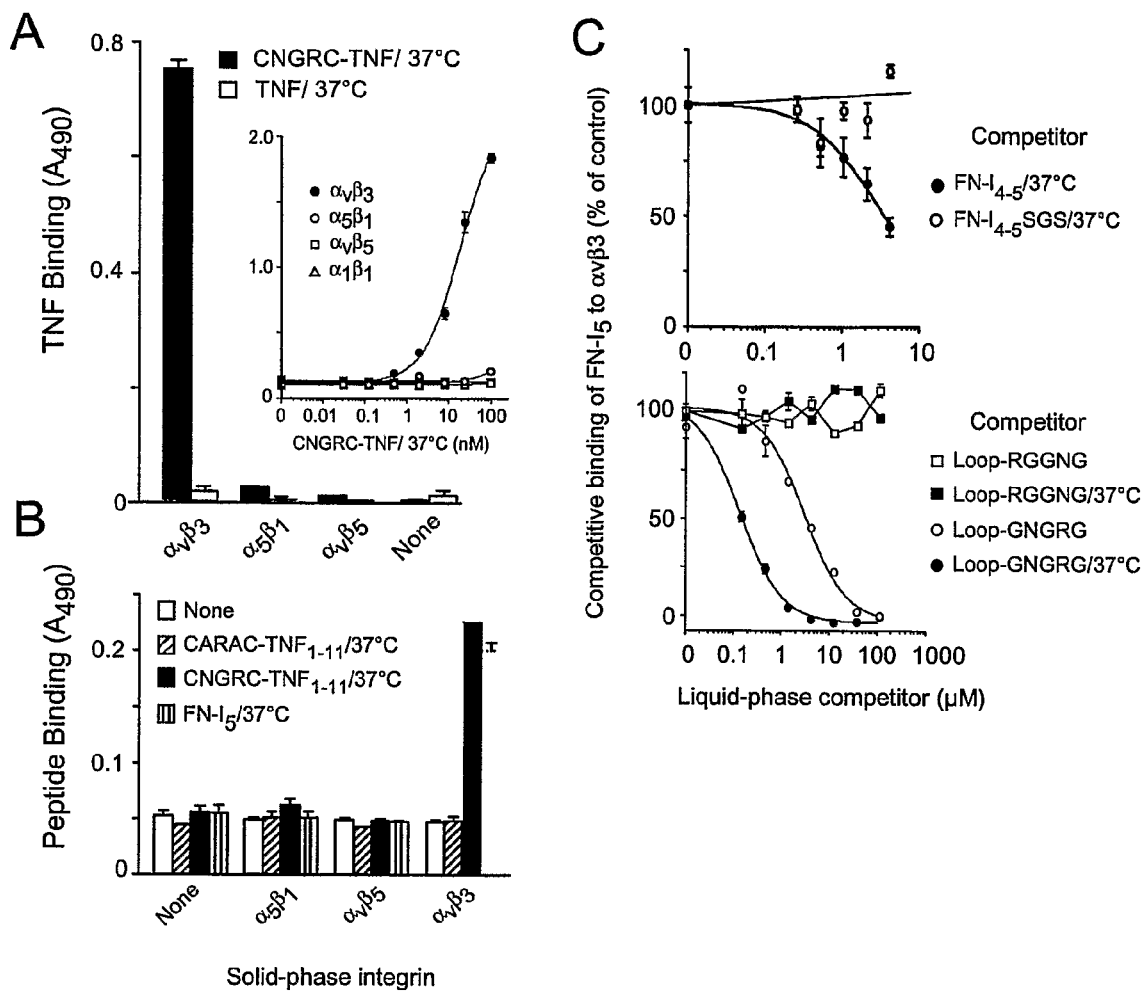

FIG. 6. FN-I$_5$ and peptides containing the NGR motif bind to α$_v$β$_3$ integrin after accelerated aging.

(A) Binding of heat-treated CNGRC-TNF and TNF to solid phases coated with purified human integrins. Single concentration (5 μg/ml) or various concentrations (inset) of CNGRC-TNF and TNF were used. Binding was detected with anti-TNF antibodies as described in Materials and Methods.

(B) Binding of biotinylated CNGRC-TNF$_{1-11}$, CARAC-TNF$_{1-11}$ and FN-I$_5$ (complexed with streptavidin-peroxidase) to purified human integrins. Binding was detected by chromogenic reaction with o-phenylendiammine.

(C) Competitive binding of biotinylated FN-I$_5$/streptavidin-peroxidase complexes to α$_v$β$_3$-coated plates with various amounts of FN-I$_{4-5}$ or FN-I$_{4-5}$SGS (upper panel or peptides corresponding to the NGR loop (residues 258-271) of FN-I$_5$ before and after heat treatment (lower panel).

Figure 7:
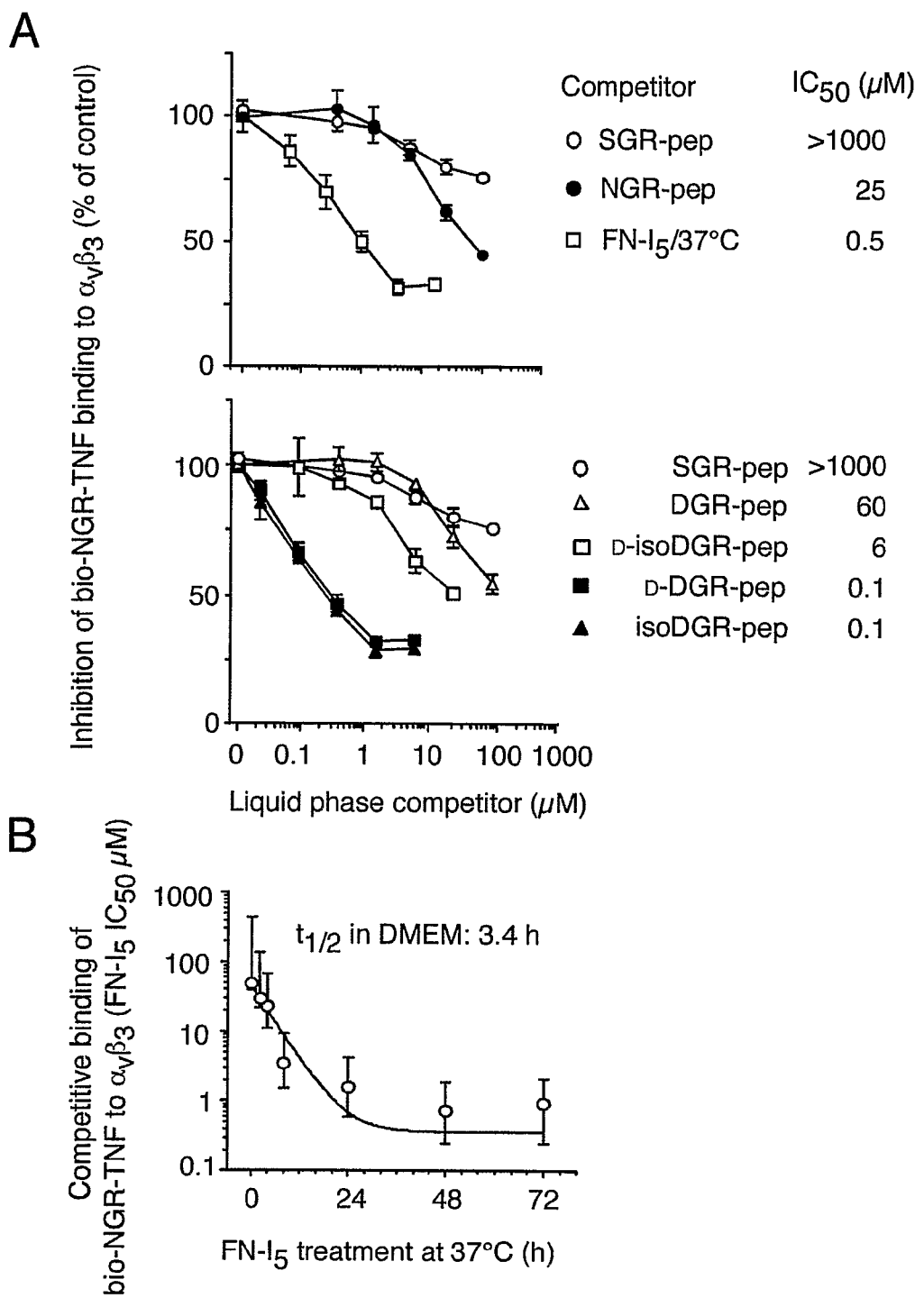

FIG. 7 Competitive binding of NGR-TNF to α$_v$β$_3$ with NGR-pep and its deamidated products to α$_v$β$_3$.

Biotinylated NGR-TNF (4 μg/ml) was mixed with different amount of the indicated peptides and added to α$_v$β$_3$ coated plates. Binding was detected as described in Materials and Methods. IC$_{50}$ was determined by nonlinear regression analysis using the GraphPad Prism software. The kinetics of deamidation of FN-I$_5$ was determined by plotting the inhibitory concentration (IC$_{50}$) versus the incubation times. Bars represent the confidence intervals for each determined IC$_{50}$.

Figure 8:
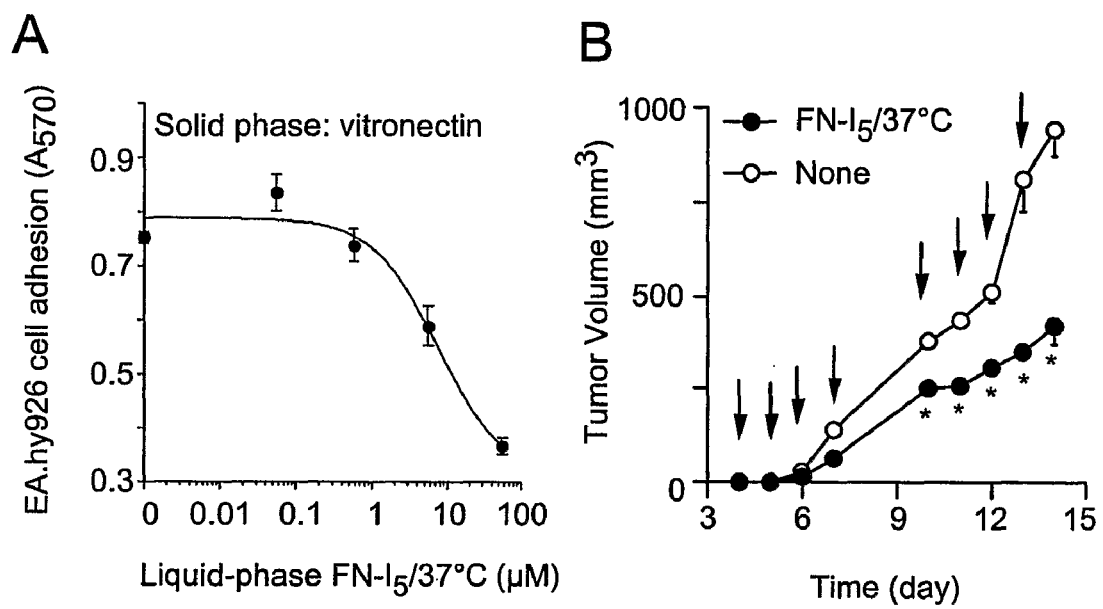

FIG. 8. Deamidated FN-I$_5$ fragment inhibits in vitro cell adhesion to vitronectin and tumor growth in a mouse model.

(A) Inhibition of EA.hy926 cell adhesion to vitronectin by heat-treated FN-I$_5$. Vitronectin (3 μg/ml) was adsorbed to microtiter plate and cell adhesion assay was performed as described in Materials and Methods.

(B) Anti-tumor effects of repeated administration of "heat-treated" FN-I$_5$ to RMA-tumor bearing mice. Animals (5/group) were treated with 200 μg of "heat-treated" FN-I$_5$ (i.p.) at the indicated times (arrows) starting 4 days after tumor implantation. * p=0.0003 at day 14, statistical analysis by two tailed t-test.

Figure 9:
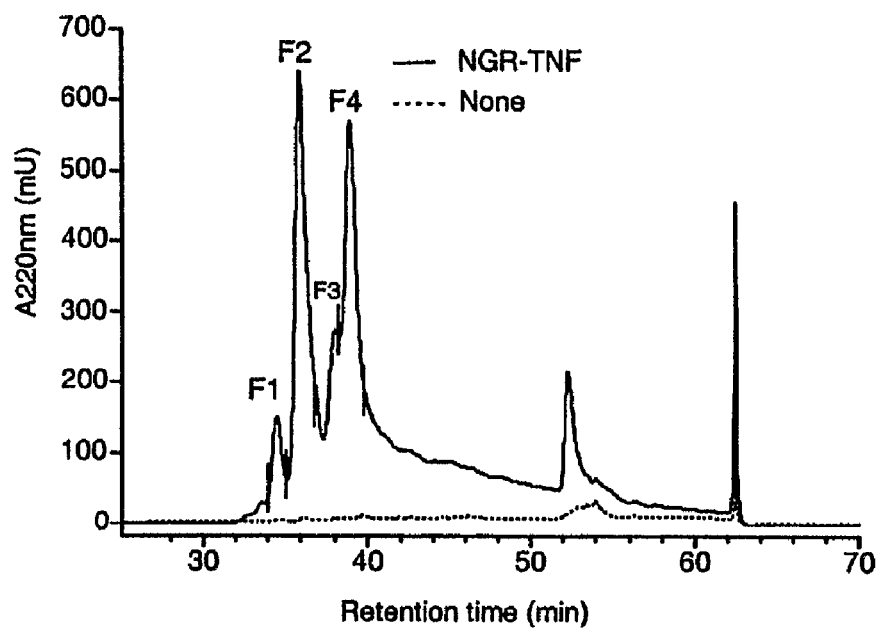

FIG. 9. RP-HPLC analysis of NGR-TNF.

RP-HPLC of NGR-TNF revealed two major peaks, F2 and F4, and two minor peaks F1 and F3. The presence of deamidated forms in these peaks was identified by measuring the amount of isoAsp in these fraction. The results showed that F2 contained much more isoAsp then F4 (Table 1).

Figure 10:
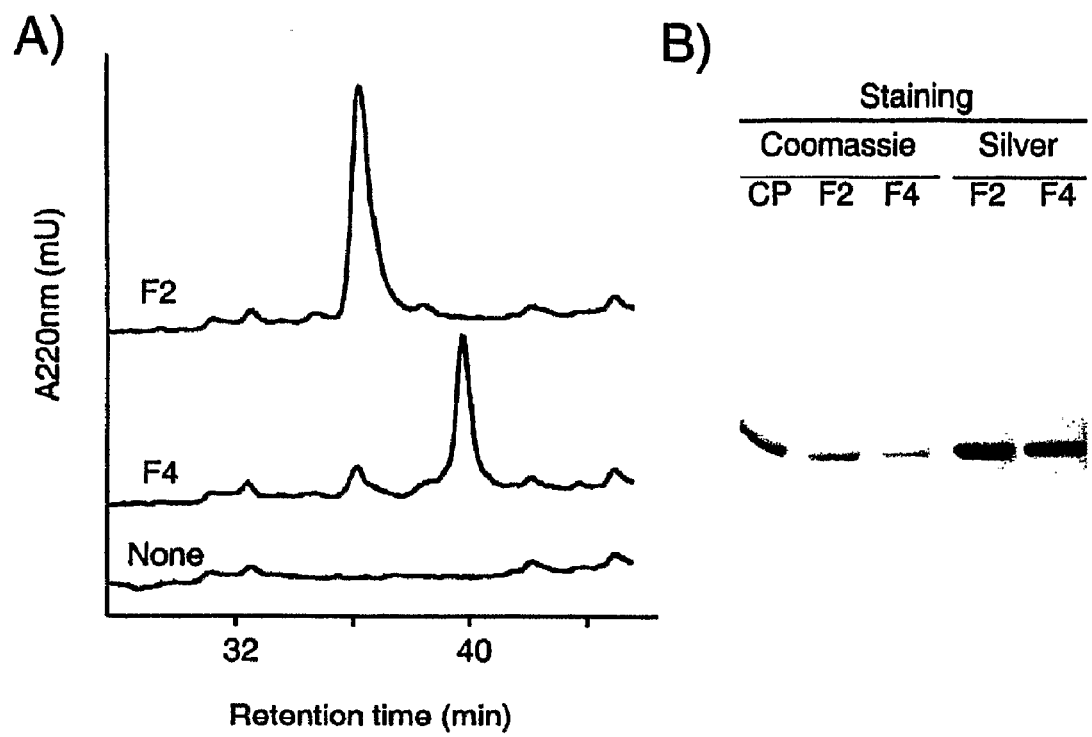

FIG. 10. RP-HPLC and SDS-PAGE of F2 and F4.

A) Re-chromatography of F2 and F4 by RP-HPLC showed that the retention time did not change after separation. B) Coomassie staining of non-reducing SDS-PAGE revealed a major band of 17-18 kDa in both F2 and F4 products, as expected for TNF monomers.

Figure 11:
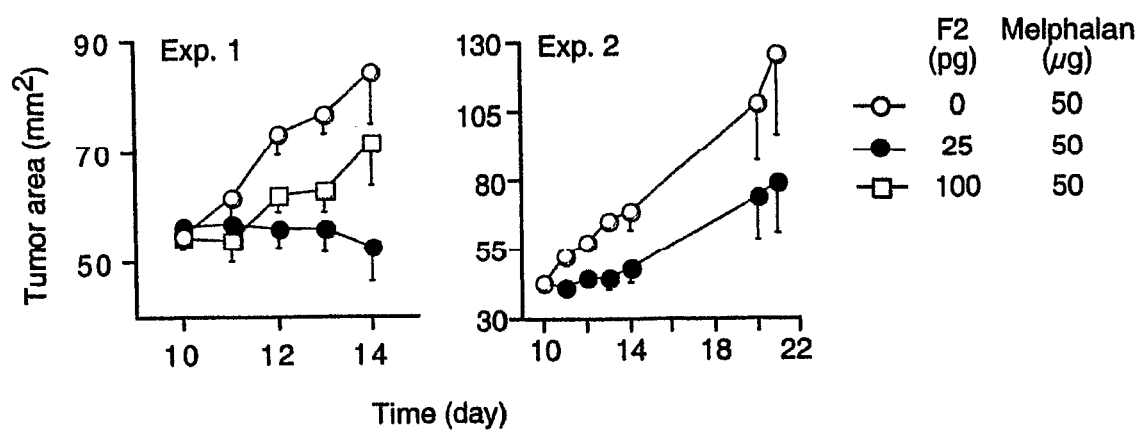

FIG. 11. Anti-tumor activity of F2 in the RMA lymphoma model.

Two experiments were performed (Exp. 1 and Exp. 2). C57BL/6 mice (Charles River Laboratories, Calco, Italy) weighing 16-18 g were challenged with subcutaneous injection in the left flank of $7 \times 10^4$ RMA living cells; 10 days later, mice were treated with 0, 25 or 100 pg of F2 (100 µl) followed 2 h later by administration of melphalan (50 µg in 100 µl). Tumor sizes are shown as mean±SE (5 animals/group).

Figure 12:
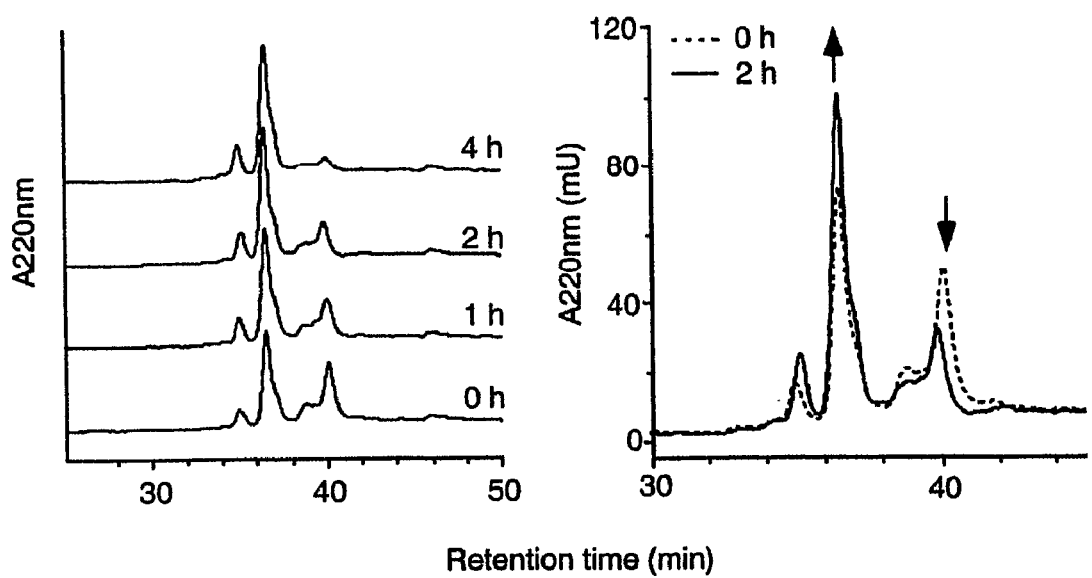

FIG. 12. RP-HPLC of NGR-TNF after treatment at 37° C. in ammonium bicarbonate pH 8.5 for various times.

NGR-TNF was diluted in 0.1 M ammonium bicarbonate buffer, pH 8.5 and incubated at 37° C. for various time. The heat treated NGR-TNF was analyzed by RP-HPLC.

Figure 13:
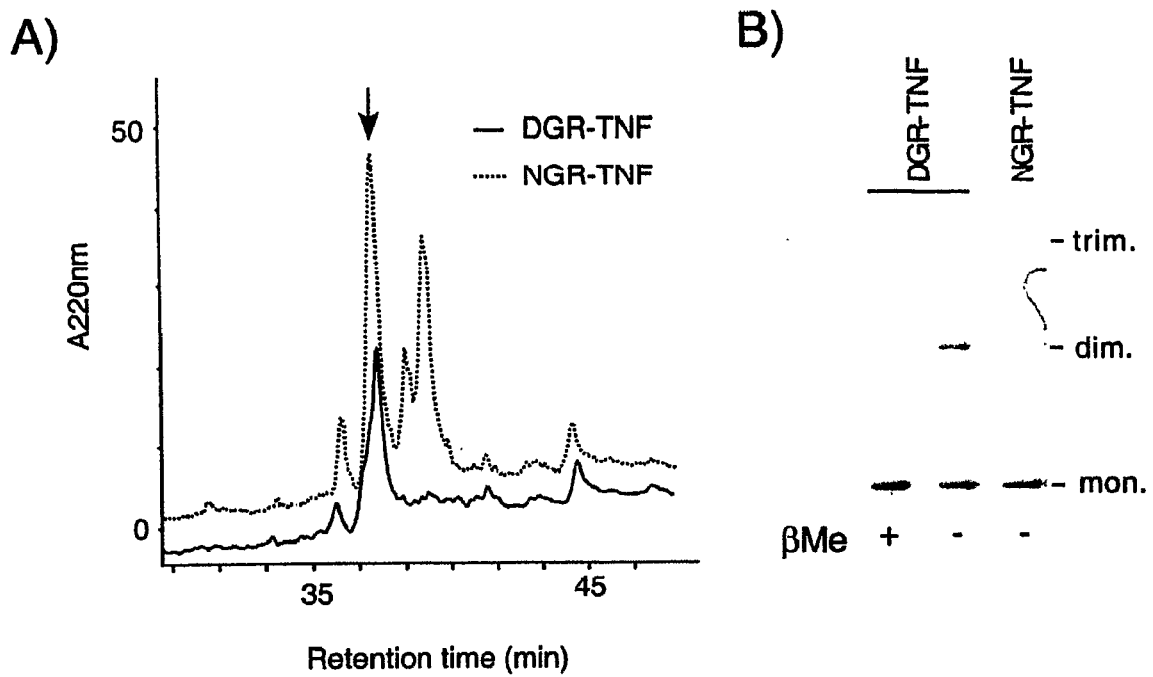

FIG. 13. RP-HPLC (A) and SDS-PAGE (B) of recombinant DGR-TNF and NGR-TNF.

Figure 14:
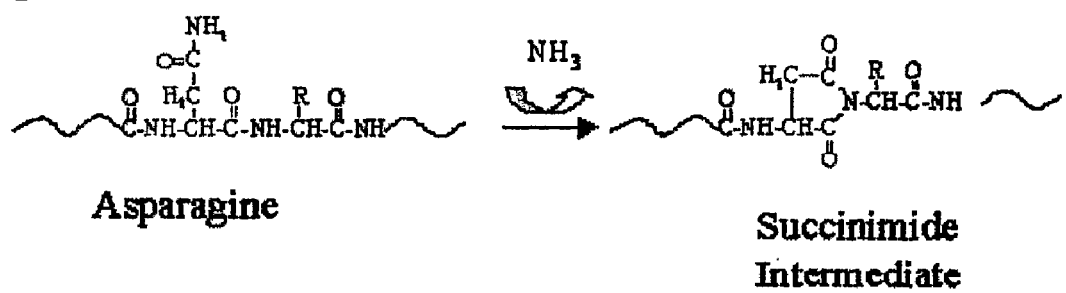
Figure 14:
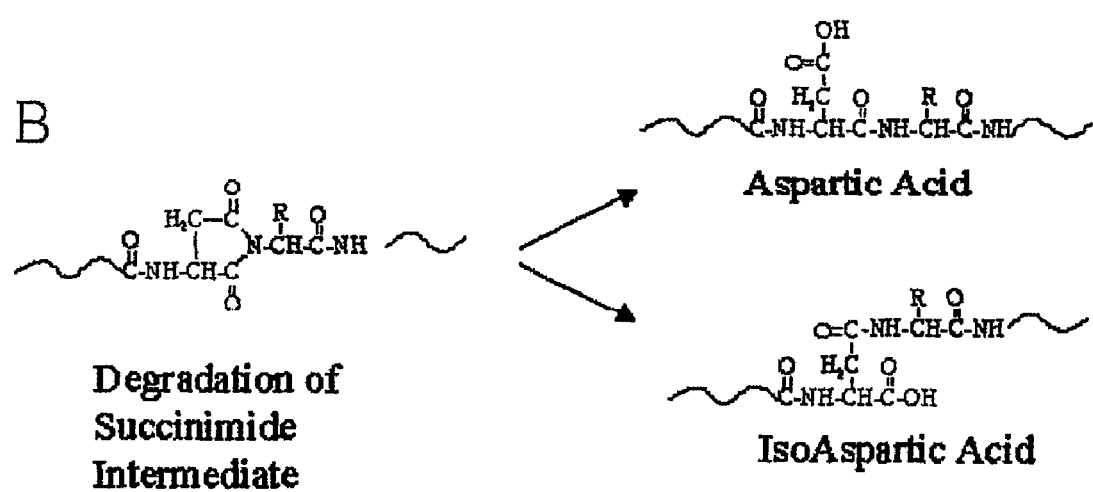

FIG. 14 shows a different structural isomeric form of aspartic acid, namely isoaspartic acid.

The following examples further illustrate the invention.

EXAMPLE 1

Materials and Methods for Examples 1 to 7

Cell Lines and Reagents

Mouse RMA lymphoma cells and EA.hy926 cells human endothelial cells fused with human lung carcinoma A549 cells) were cultured as described previously (Curnis et al., 2005; Ljunggren and Karre, 1985). Crystal violet (Fluka Chemie); bovine serum albumin (BSA), goat anti-rabbit IgG horseradish peroxidase conjugate, FN-70 KDa, FN-45 KDa and FN-30 KDa fragments (Sigma); RetroNectin (Takara Biomedicals). Human $\alpha_v\beta_3$, $\alpha_v\beta_5$, $\alpha_5\beta_1$ and $\alpha_1\beta_1$ integrins (Immunological Sciences); streptavidin-peroxidase (Società Prodotti Antibiotici).

Preparation and Characterization of Recombinant FN-I$_{4-5}$ and FN-I$_{4-5}$SGS The cDNA coding for human fibronectin 4-5$^{th}$ type I repeats (FN-I$_{4-5}$; residue 184-273 of fibronectin) was prepared by RT-PCR on MSR-3-mel cells total RNA (Tanzarella et al., 1999) using the following primers: 5'-CTGGATC-CGAGAAGTGTTTTGATCATGCTGCTGGG (forward) (SEQ ID NO: 37) and 5' TATATTAAGCTTTCAGTGC-CTCTCACACTTCC (reverse) (SEQ ID NO: 38). A control fragment with NGR replaced with SGS (FN-I$_{4-5}$SGS), was generated by PCR on FN-I$_{4-5}$ plasmid using the above forward primer and the following reverse primer: 5'-TATAT-TAAGCTTTCAGTGCCTCTCACACTTC-CACTCTCCACTGCCGCTG (SEQ ID NO: 39). Amplified fragments were cloned into a pRSET-A plasmid (Invitrogen), expressed in BL21(DE3)pLysS E. coli cells as soluble proteins (with an His-tag at the N-terminus) and purified from cell extracts by metal-chelate affinity chromatography.

Preparation and Characterization of Synthetic Peptides

Various peptides (biotinylated and non biotinylated) were prepared by chemical synthesis using an Applied Biosystem model 433A peptide synthesizer. Aminoacids in L-configuration were used except when indicated. A synthetic peptide corresponding to the 5$^{th}$ type I repeat of human fibronectin (FN-I$_5$), residues 230-274 of mature protein (accession number P02751, Swiss-Prot), was also synthesized with an additional N-terminal acetyl-glycine and with Glu$^{250}$ in place of Asp$^{250}$. To promote disulfide formation between Cys$^{258}$-Cys$^{270}$ and Cys$^{231}$-Cys$^{260}$ in FN-I$_5$ (see FIG. 1), Cys$^{258}$ and Cys$^{270}$ were protected with S-trityl groups (removable by trifluoroacetic acid after side-chain deprotection and cleavage from the resin), whereas Cys$^{231}$ and Cys$^{260}$ were protected with S-acetamidomethyl groups (removable by treatment with iodine). After RP-HPLC purification of peptide, the Cys$^{258}$-Cys$^{270}$ disulfide bridge was formed by incubating 20 µmoles of peptide in 300 ml of 8% DMSO at pH 7 (room temperature, overnight). The peptide was then purified by RP-HPLC and lyophilized. To form the second Cys$^{231}$-Cys$^{260}$ disulfide bridge, 13.5 µmoles of peptide was dissolved in 67 ml of 80% v/v acetic acid and mixed with 0.135 ml of 1 N hydrochloric acid. Then, 21 mg of iodine, dissolved in 2 ml of methanol, was added to the peptide solution under stirring. After 90 min, 1 mmole of ascorbic acid was added, to quench iodine. The peptide was then purified by RP-HPLC.

All peptides were dissolved in sterile water and stored in aliquots at −20° C. Peptide purity was analyzed by RP-HPLC. Free sulfhydryl groups in all peptide preparations were <0.1% as checked by titration with Ellman's reagent (Pierce, Rockford, Ill.). Peptide identity was checked by MALDI-TOF or ESI-MS mass spectrometry. The molecular mass of peptides used throughout this work was similar to the expected value. ESI-MS analysis of FN-I$_5$ showed the presence of an additional component of +144 Da, corresponding to FN-I$_5$ with unremoved acetamidomethyl groups.

Preparation and Characterization of CNGRC-TNF, CDGRC-TNF and CNGRC-TNF$_{1-11}$ Conjugates Murine TNF and CNGRC-TNF (consisting of murine TNF fused with the C-terminus of CNGRCG) were prepared by recombinant DNA technology as described (Curnis et al., 2000).

The cDNA coding for CDGRC-TNF (murine TNF fused with the C-terminus of CDGRCG) was prepared by PCR on CNGRC-TNF plasmid (Curnis et al., 2000) using the following primers: 5'-CACCATGGGCAACGGCCGTGGCG-GCGTC (forward) (SEQ ID NO: 40); 5'-TCAGGATCCT-CACAGGGCAATGATCCCAAAGTAGAC (reverse) (SEQ ID NO: 41). The amplified cDNA was cloned into the pET101/D-TOPO plasmid (Invitrogen), expressed in BL21 (DE3) E. coli cells (Novagen) and purified from cell extracts by affinity chromatography on soluble p75-TNF receptor—Sepharose essentially as described previously for CNGRC-TNF (Colombo et al., 2002). Both CNGRC-TNF and CDGRC-TNF were subjected to a refolding procedure as described previously (Curnis et al., 2000).

Protein purity and identity were checked by SDS-PAGE, electrospray mass spectrometry and gel-filtration chromatography. The in vitro cytolytic activity of CNGRC-TNF and CDGRC-TNF, measured by standard cytolytic assay with L-M mouse fibroblasts (Corti et al., 1994), were 2.96 (±0.56)×10$^8$ U/mg and 2.59 (±0.69)×10$^8$ U/mg, respectively.

CNGRC-TNF$_{1-11}$, corresponding to the N-terminal sequence of NGR-TNF (lacking TNF activity) and CARAC-TNF$_{1-11}$ peptide, were prepared by chemical synthesis as described above.

Accelerated Aging (Heat Treatment) of Fibronectin Fragments and Peptides

Fibronectin fragments, peptides and peptide-TNF conjugates were diluted in 0.1 M ammonium bicarbonate buffer, pH 8.5, incubated for 16 h at 37° C., and stored at −20° C. until analysis. These products are hereinafter referred to as "heat treated".

Isoaspartate (isoAsp) Quantification

IsoAsp content in untreated and "heat treated" CNGRC (SEQ ID NO: 6)—TNF and peptides was quantified by using the ISOQUANT™ Isoaspartate Detection Kit (Promega).

Cell Adhesion Assay and PIMT Treatment

Untreated and "heat treated" fibronectin fragments, peptides and peptide-TNF conjugates were diluted at the desired concentration with 150 mM sodium chloride, 50 mM sodium phosphate, pH 7.3, and added to 96-well polyvinyl chloride microtiter plates (Falcon, Becton Dickinson). After overnight incubation at 4° C., the plates were washed, seeded with EA.hy926 cell in DMEM containing 0.1% BSA (40000 cells/well) and left to incubate for 2-3 h at 37° C., 5% $CO_2$. Adherent cells were fixed and stained with crystal violet as described (Curnis et al., 2005).

The effect of protein$\overline{L}$-isoAsp/D-Asp$\overline{O}$-methyltransferase (PIMT) on the pro-adhesive properties of different fragments was investigated as follows: microtiter plates were coated with various products as described above and washed with 0.9% sodium chloride. Each well was then filled with 45 µl of a solution containing 0.02 mM S-adenosyl-L-methionine in 150 mM sodium chloride, 50 mM sodium phosphate buffer, pH 6.8, and 5 µl of PIMT solution (from the Isoquant Isoaspartate Detection kit, Promega) (final volume 50 µl/well) and incubated at 37° C. for 16 h. After incubation the plates were washed with 0.9% sodium chloride and cell adhesion assay was performed as described above.

Binding of Peptides and Proteins to Integrins

Human $\alpha_v\beta_3$, $\alpha_v\beta_5$, $\alpha_5\beta_1$ and $\alpha_1\beta_1$ integrins solutions, 0.5-2 µg/ml in phosphate buffered saline with $Ca^{2+}$ and $Mg^{2+}$ (DPBS, Cambrex), were added to 96-well polyvinylchloride microtiter plates (50 µl/well) and left to incubate overnight at 4° C. All subsequent steps were carried out at room temperature. The plates were washed with DPBS and further incubated with DPBS containing 3% BSA (200 µl/well, 1 h). The plates were then washed and filled with CNGRC (SEQ ID NO: 6)—TNF or TNF solutions (5 µg/ml, 50 µl/well in 3% BSA-DPBS) and left to incubate for 2 h. After washing with DPBS, each well was incubated with purified rabbit anti-murine TNF IgGs in 3% BSA-DPBS containing 1% normal goat serum (10 µg/ml, 50 µl/well, 1 h) followed by a goat anti-rabbit peroxidase conjugate in the same buffer (50 µl/well, 1 h). Bound peroxidase was detected by adding o-phenylendiammine chromogenic substrate.

Binding of biotinylated peptides (CNGRC (SEQ ID NO: 6)-$TNF_{1-11}$, CARAC (SEQ ID NO: 36)-$TNF_{1-11}$ and FN-$I_5$) to purified integrins was studied using streptavidin-peroxidase conjugate complexes. Complexes were prepared by mixing various quantities (0.5-1 µg) of heat-treated biotinylated peptides in DPBS containing 3% BSA with 0.03 units of streptavidinperoxidase (binding capacity: 1 µg of biotin/unit of streptavidin-peroxidase) (final volume 15 µl). Complexes were diluted in 3% BSA-DPBS (1:500), added to microtiterplates coated with integrins as described above, and incubated for 2 h at room temperature. After washing with DPBS, bound peroxidase was detected by chromogenic reaction as described above. Each assay was carried out in triplicate.

In Vivo Studies

Studies on animal models were approved by the Ethical Committee of the San Raffaele H Scientific Institute and performed according to the prescribed guidelines. C57BL/6N mice (Charles River Laboratories, Calco, Italy) weighing 16-18 g were challenged with subcutaneous injection in the left flank of 7×10⁴ RMA living cells; 4 days later, the mice were treated daily with 200 µg of heat-treated FN-$I_5$ (100 µl) in 0.9% sodium chloride (i.p.). Tumor growth was monitored by measuring the tumors with calipers as previously described (Gasparri et al., 1999). Animals were sacrificed before the tumors reached 1.0-1.3 cm in diameter. Tumor sizes are shown as mean±SE (5 animals/group).

EXAMPLE 2

Accelerated Aging of Fibronectin Fragments Generates NGR-Dependent Adhesion Sites Accelerated Aging of Fibronectin Fragments Generates NGR-Dependent Adhesion Sites The adhesion of EA.hy926 cells to natural, recombinant and synthetic fibronectin fragments containing the NGR motif was studied. First, the following proteolytic fragments of fibronectin were studied: a) FN-70 KDa, containing the FN-$I_{1-9}$ and FN-$II_{1-2}$ repeats; b) FN-30 KDa, containing the FN-$I_{1-5}$ repeats; c) FN-45 KDa, containing the FN-$I_{6-9}$ and FN-$II_{1-2}$ (see FIG. 1 for a schematic representation). All fragments, after adsorption to microtiterplates, induced cell adhesion and spreading (FIG. 2), suggesting the presence of pro-adhesive sites in these regions.

Figure 3:
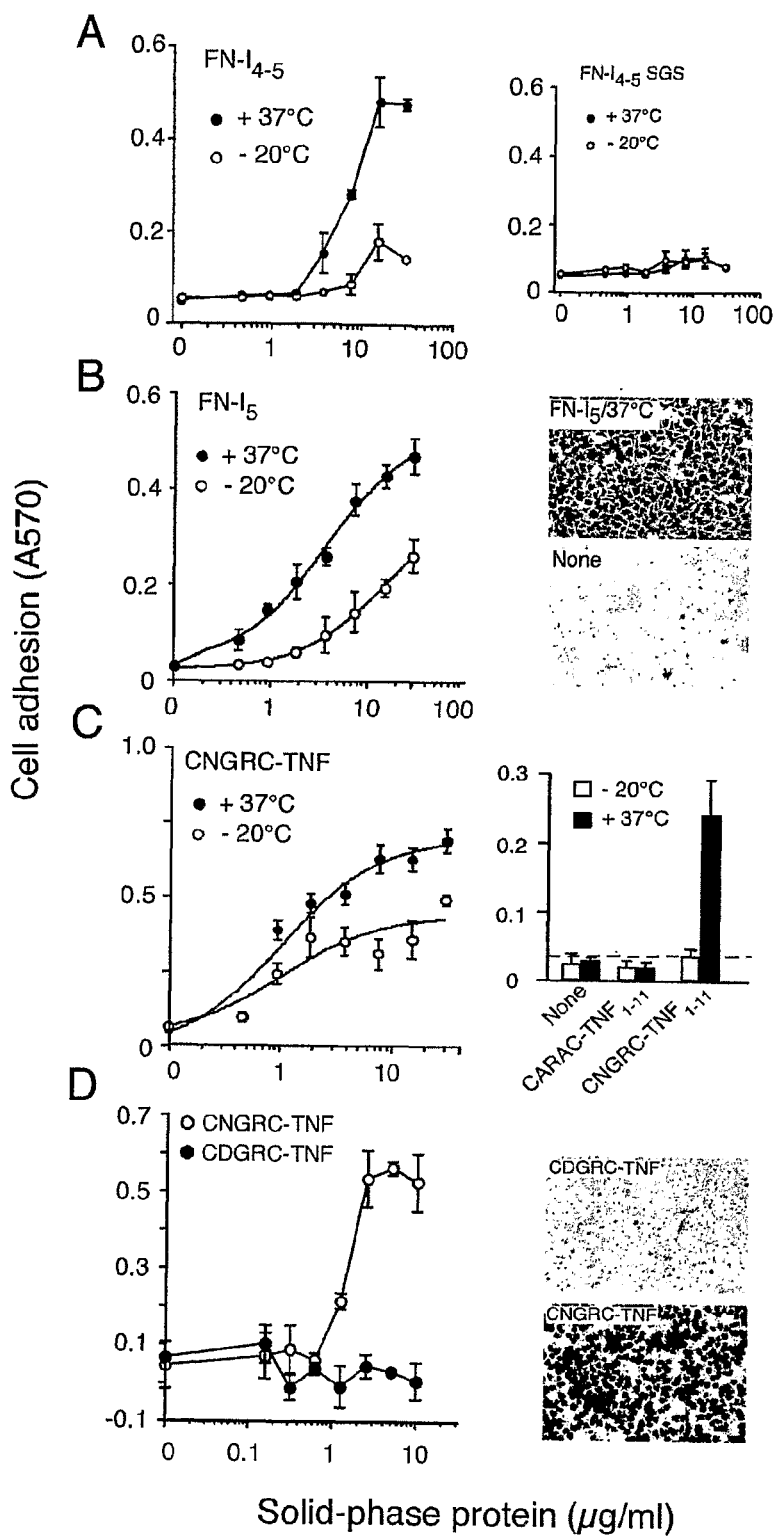

To investigate the role of the NGR motif in the FN-$I_5$ repeat, we then analyzed the pro-adhesive properties of FN-$I_5$, FN-$I_{4-5}$ and FN-$I_{4-5}$SGS fragments, the latter corresponding to a mutant with SGS in place of NGR (residues 263-265). Recombinant FN-$I_{4-5}$, but not the SGS mutant, promoted cell adhesion (FIG. 3A). When we incubated these fragments in 0.1 M ammonium bicarbonate buffer, pH 8.5, for 16 h at 37° C. (from now on this treatment called "heat-treatment") we observed an increase of cell adhesion to FN-$I_{4-5}$, but not to FN-$I_{4-5}$SGS (FIG. 3A). This suggests that a cell adhesion site, somehow related to the NGR sequence, was generated by accelerated aging. Similar results were obtained with synthetic FN-$I_5$ (FIG. 3B).

To assess whether the NGR motif was sufficient for mediating this phenomenon, we investigated the pro-adhesive properties of short peptides containing the NGR-motif, before and after heat treatment. Since the NGR tripeptide is unlikely to fold and to bind to microtiterplates, we introduced two flanking cysteines. The rationale for using flanking cysteines was based on the fact that the predicted conformation of CNGRC (SEQ ID NO: 6) peptide, by molecular dynamic simulation, is similar to that of the GNGRG (SEQ ID NO: 4) loop of FN-$I_5$ repeat (Colombo et al., 2002). Furthermore, we fused this peptide to TNF (CNGRC (SEQ ID NO: 6)-TNF) or to the first eleven residues of TNF (CNGRC (SEQ ID NO: 6)-D-$TNF_{1-11}$, devoid of TNF activity) to enable adsorption to microtiterplates. As expected heat treatment of CNGRC (SEQ ID NO: 6)-TNF increased cell adhesion (FIG. 3C). No adhesion was observed to TNF alone either before or after heat treatment (data not shown). Similarly, heat treatment of CNGRC (SEQ ID NO: 6)-$TNF_{1-11}$, but not of CARAC (SEQ ID NO: 36)-$TNF_{1-11}$ (a control peptide), increased cell adhesion (FIG. 3C, right).

These results support the hypothesis that the NGR motif is sufficient for promoting cell adhesion after heat treatment.

Interestingly, a CDGRC (SEQ ID NO: 23)-TNF conjugate, prepared by recombinant DNA technology, was completely inactive (FIG. 3D) even after heat treatment (not shown), suggesting that Asn is a crucial residue for the enhanced activity. In conclusion these results suggest that structural changes somehow related to the Asn residue of NGR motif in FN-I$_5$ lead to generation of a pro-adhesive site.

EXAMPLE 3

Deamidation of the NGR is Associated with Increased Cell Adhesion

It is well known that the Asn residues, particularly when followed by Gly, can undergo non-enzymatic deamidation at physiological pH (Robinson and Robinson, 2001; Robinson et al., 2004; Stephenson and Clarke, 1989; Tyler-Cross and Schirch, 1991). This reaction leads to formation of Asp or isoAsp, L-Asp ($_L$D), L-isoAsp, ($_L$isoD), D-Asp ($_D$D), and D-isoAsp ($_D$isoD), although the L-configuration predominates (Geiger and Clarke, 1987). Accordingly we found that the molecular mass of FN-I$_5$, CNGRC (SEQ ID NO: 6)-TNF and CNGRC (SEQ ID NO: 6) peptides was increased by about 1 Da, by mass spectrometry analysis, after heat treatment. Furthermore, isoAsp analysis of CNGRC (SEQ ID NO: 6)-TNF showed the presence of >0.5 pmol isoAsp/mol of CNGRC (SEQ ID NO: 6)-TNF subunit after heat treatment.

To assess whether the enhanced adhesive properties of FN-I$_5$ after heat-treatment depended on NGR deamidation, we incubated the "heat treated" FN-I$_5$ and CNGRC (SEQ ID NO: 6)-TNF with the proteinL-isoAsp/D-AspO-methyltransferase (PIMT), an enzyme that converts L-isoAsp and D-Asp residues to L-Asp (Aswad, 1984; Galletti et al., 1988; Lowenson and Clarke, 1992; McFadden and Clarke, 1987; Murray and Clarke, 1984). PIMT almost completely inhibited the pro-adhesive activity of heat-treated FN-I$_5$ and CNGRC fSEQ ID NO: 6)-TNF (FIG. 4A). Moreover, this enzymatic treatment partially inhibited the pro-adhesive properties of natural FN-30 KDa (FIG. 4B) and FN-45 KDa fragment (not shown) suggesting that Asn deamidation can occur also in natural fibronectin fragments. To assess the specificity of this reaction we evaluated also the effect of PIMT on retronectin, a FN fragment that is known to promote cell adhesion via RGD (see FIG. 1). As expected, in this case no inhibition was observed after enzymatic treatment (FIG. 4B). Conversely, in this case we observed a modest but significant increase. This was not totally unexpected as also RGD can undergo isomerization of Asp residues, with formation of isoAsp and loss of function (Geiger and Clarke, 1987; Lanthier and Desrosiers, 2004; Reissner and Aswad, 2003; Stephenson and Clarke, 1989). Thus, in this case PIMT is expected to "repair" RGD and increase cell adhesion. In conclusion, these results suggest that NGR deamidation, in contrast to RGD isomerization, is associated with a "gain of function" in cell adhesion assays.

EXAMPLE 4

Kinetics of NGR Deamidation

The stability of NGR and the kinetics of $_L$isoDGR or $_D$DGR formation at pH 7.3 (DMEM) and pH 8.5 (ammonium bicarbonate), were then investigated. To this aim the CNGRCGVRY (SEQ ID NO: 42) peptide (called NGR-pep) was synthesized and analyzed by reverse-phase HPLC, before and after incubation at 37° C. Residues GVRY (SEQ ID NO: 72) were added to the C-terminus of CNGRC (SEQ ID NO: 6) to enable column adsorption. In addition five peptides called, DGR-pep, $_D$-DGR-pep, isoDGR-pep, $_D$-isoDGR and SGR-pep, corresponding to the same sequence of NGR-pep except for the presence of D, $_D$-D, $_L$-isoD, $_D$-isoD and S, respectively in place of N were prepared. The half-life of NGR-pep at pH 7.3 and 8.5, estimated from the height of the main chromatographic peak (peak 1), was about 4 and 2 h, respectively (FIG. 5A, inset). Peptides corresponding to deamidation products were stable under these conditions (FIG. 5B).

To identify peaks and to verify that the measured half-life correspond to Asn deamidation, and not to other structural changes, we analyzed heat-treated NGR-pep peptide spiked with fresh NGR-pep, or DGR-pep or isoDGR-pep peptides. The results showed that peak 1, 2 and 3 observed after NGR-pep incubation correspond to NGR-pep, DGR-pep and isoDGR-pep peptides, respectively. Of note the NGR-pep was stable for more than one week at 37° C. when stored in water.

EXAMPLE 5

$\alpha_v\beta_3$ is a Receptor of $_D$isoDGR and $_D$DGR Motifs

The binding of heat-treated FN-I$_5$, CNGRC (SEQ ID NO: 6)-TNF and short peptides to purified $\alpha_v\beta_3$, $\alpha_v\beta_5$, $\alpha_5\beta_1$ and $\alpha_1\beta_1$ integrins was then investigated by direct and competitive ELISA with integrins adsorbed on microtiterplates.

We observed binding of all NGR-containing molecules (heat-treated) to $\alpha_v\beta_3$, but little, or not at all, to the other integrins (FIGS. 6A and B). No binding was observed with heat-treated TNF or with a control CARAC (SEQ ID NO: 36)-TNF$_{1-11}$ peptide (FIGS. 6A and B), suggesting that NGR was critical. Of note, we observed binding of CNGRC (SEQ ID NO: 6)-TNF to $\alpha_v\beta_3$ even before heat treatment (data not shown), although to a lower extent, possibly due to deamidation occurring during preparation and/or assay incubation.

To verify the importance of the NGR loop of FN-I$_5$ for integrin binding we performed competitive binding experiments with recombinant FN-I$_{45}$ and FN-I$_{4-5}$SGS, the latter lacking NGR. As expected only the fragment with NGR could compete the binding of FN-I$_5$ to $\alpha_v\beta_3$ (FIG. 6C). Binding competition was observed also with a peptide corresponding to the entire 256-271 loop of FN-I$_5$ (see FIG. 1C), but not with a control peptide with a scrambled sequence at the GNGRG (SEQ ID NO: 4) site (FIG. 6 C).

Accordingly this binding was efficiently competed with $_D$DGR-pep and isoDGR-pep (EC$_{50}$, 0.1 µM) and heat-treated FN-I$_5$ (EC$_{50}$, 0.4 µM) and less efficiently with $_D$isoDGR-pep or DGR-pep, NGR-pep, SGR-pep (EC$_{50}$, >10 µM) (FIG. 7).

Considering that the isoDGR-pep or $_D$DGR-pep peptides are stable under these assay conditions these results suggest that isoDGR-pep or $_D$DGR-pep motives new ligands of $\alpha_v\beta_3$.

EXAMPLE 6

Kinetics of Integrin Binding Site Formation in FN-I$_5$

To investigate the kinetics of integrin binding site in FN-I$_5$ we have performed additional competitive binding studies with various doses of FN-I$_5$, incubated for different times at 37° C. in DMEM. Interestingly, when we plotted the inhibitory concentration (IC$_{50}$) versus the incubation times we observed that maximal competitive binding activity was reached after 24-48 h of incubation (half life 3.4 h) (FIG. 7B). This value corresponds very well to the half fife of NGR-pep deamidation described above, and further support the concept that the integrin binding proprieties of heat treated FN-I$_5$ were indeed related to the NGR-deamidation.

EXAMPLE 7

Deamidated FN-I$_5$ Fragments Inhibits In Vitro Cell Adhesion to Vitronectin and Tumor Growth in a Mouse Model It is well known that $\alpha_v\beta_3$ integrin, the vitronectin receptor, plays a critical role in angiogenesis (Hynes, 2002). Compounds able to inhibit the interaction of this integrin with ECM proteins are known to inhibit angiogenesis and tumor growth (Brooks et al., 1994; Brooks et al., 1995; Friedlander et al., 1995; Friedlander et al., 1996; Hammes et al., 1996). We have observed that deamidated FN-I$_5$ fragments could inhibit the adhesion of EA.hy926 cells to vitronectin (FIG. 8A). Furthermore, this fragment, when was daily administered to RMA lymphoma bearing mice, significantly inhibited tumor growth in vivo (FIG. 8B). These results suggest that deamidated fragments of FN could play a role in cell adhesion and tumor biology.

EXAMPLE 8

Isolation of a Deamidated form of NGR-TNF

To prepare murine Cys-Asp-Gly-Arg-Cys-Gly-(SEQ ID NO: 24)TNF (DGR-TNF) and Cys-isoAsp-Gly-Arg-Cys-Gly-(SEQ ID NO: 60)TNF (isoDGR-TNF) we cloned and expressed Cys-Asn-Gly-Arg-Cys-Gly-(SEQ ID NO: 7)TNF (NGR-TNF) in *E. coli* cells and purified deamidated forms (spontaneously produced during the production process) from this product.

The cDNA coding for NGR-TNF (consisting of TNF fused with the C-terminus of CNGRCG (SEQ ID NO: 7)) was first prepared by recombinant DNA technology using *E. coli* cells and purified as described (Curnis et al., 2000). To isolate the deamidated forms from this preparation we performed a further purification step based on reversed phase chromatography (RP-HPLC) on a C-4 column (Hi-pore Reversed Phase column, 250×4.6 mm, Biorad), as follows: mobile phase A; 5 mM sodium phosphate buffer, pH 6.8, containing 5% acetonitrile in water, mobile phase B, 5 mM sodium phosphate buffer, pH 6.8, containing 70% acetonitrile in water; 0% B for 10 min, 30% B for 5 min, linear gradient 30-65% B in 35 min, 100% B for 10 min, 0% B for 10 min, flow rate 2 ml/min. The elution was monitored at 214 nm and 280 nm (HPLC, LC-126 nM, Beckman Coulter). RP-HPLC of NGR-TNF revealed two major peaks, called F2 and F4, and two minor peaks called F1 and F3 (FIG. 9). The presence of deamidated forms in these peaks was identified by measuring the amount of isoAsp in these fraction. The results showed that F2 contained much more isoAsp then F4 (Table 1).

Re-chromatography of F2 and F4 by RP-HPLC showed that the retention time did not change after separation, suggesting that these products were stable. Coomassie staining of non-reducing SDS-PAGE revealed a major band of 17-18 kDa in both F2 and F4 products, as expected for TNF monomers (FIG. 10, inset)

The biochemical and biological properties of F2 and F4 were further characterized (Table 1). Electrospray mass spectrometry analysis showed that molecular mass of F2 was 1 Da greater than that of F4. Moreover, the cytolytic activities of F2 and F4 against L-M cell were similar. This result, together with the data on isoAsp content, suggests that F2 corresponds to a deamidated form of NGR-TNF.

To assess whether deamidation took place in the N-terminal CNGRC (SEQ ID NO: 6) domain we performed sequence analysis of the N-terminus by the Edman degradation method (not shown). The results confirmed that deamidation took place at the N-terminus, as Asp$^2$ was detected in place of Asn$^2$. This and the above data suggest that F2 was a mixture of isoDGR-TNF (75%) and DGR-TNF, with isoaspartyl and aspartyl residues in position 2.

The in vivo anti-tumor properties of F2 were then investigated using the RMA lymphoma model. Studies on animals were approved by the Ethical Committee of the San Raffaele H Scientific Institute and performed according to the prescribed guidelines. C57BL/6 mice (Charles River Laboratories, Calco, Italy) weighing 16-18 g were challenged with subcutaneous injection in the left flank of 7×10$^4$ RMA living cells; 10 days later, mice were treated with 0, 25 or 100 pg of F2 (100 µl) followed 2 h later by administration of melphalan (50 µg in 100 µl) (Glaxo Wellcome Operations, Dartford, Great Britain). All drugs, diluted with 0.9% sodium chloride containing 100 µg/ml endotoxin-free human serum albumin (Farma-Biagini SpA, Lucca, Italy), were administered intraperitoneally. Tumor growth was monitored daily by measuring the tumors with calipers as previously described (34). Animals were sacrificed before the tumors reached 1.0-1.3 cm in diameter. Tumor sizes are shown as mean±SE (5 animals/group).

The results showed that very low doses (25 pg) of F2 could induce anti-tumor effects when administered in combination with melphalan (FIG. 11).

EXAMPLE 9

Preparation of isoDGR-TNF/DGR-TNF by Treatment of NGR-TNF with 0.1 M Ammonium Bicarbonate Buffer Buffer composition, ionic strength, pH and temperature can increased the deamidation/isomerization rate of the Asn residue. Thus, to develop a rapid method for the preparation of F2 (iDGR-TNF/DGR-TNF) we have diluted NGR-TNF in 0.1 M ammonium bicarbonate buffer, pH 8.5 and incubated at 37° C. for various times. The heat treated NGR-TNF was analyzed by RP-HPLC. FIG. 12 shows that F4 was rapidly converted into F2 after this treatment. Remarkably, no loss of cytolytic activity was observed after 4 h of treatment, indicating that this process can be exploited for producing isoDGR-TNF/DGR-TNF.

EXAMPLE 10

Preparation of DGR-TNF by Recombinant DNA Technology

The cDNA coding for DGR-TNF (mouse TNF fused with the C-terminus of CDGRCG (SEQ ID NO: 24)) was obtained by PCR on NGR-TNF plasmid, using the following primers: 5' <u>CACCATG</u>TGCGACGGCCGTTGCGGC 3' (SEQ ID NO: 43) (5' primer); 5' CTGGATCC<u>TCA</u>CAGAGCAATGATCCCAAAG '3 (SEQ ID NO: 44) (3' primer). Both primers were designed to allow the directional cloning into a pET101/D-TOPO plasmid expression kit (Invitrogen). The underlined sequence in 5' primer contains the sequence necessary to enable the directional cloning and the initial translation codon whereas the 3' primer contains the stop codon (underlined). The PCR reaction and the cloning procedure were performed as recommended by the manufacturer's instruction. The DGR-TNF cDNA was expressed in BL21(DE3) *E. coli* cells (Novagen) and purified from cell extracts by affinity chromatography on soluble p75-TNF receptor—Sepharose as follows: 10 mg of commercially available recombinant p75-TNF receptor (Embrel) were coupled to 2.5 ml of activated-CH-Sepharose (Amersham Biosciences Europe GmbH, Freiburg, Germany) according to the manufacturer's instruction. The column was washed extensively 100 mM Tris-HCl buffer containing pH 8.0, loaded with DGR-TNF crude extract, diluted in 20 mM Tris-HCl buffer conatining 2 mM EDTA pH 8.0, and desorbed by elution with 7 M urea, 100 mM Tris-HCl, pH 8.0. DGR-TNF was then refolded as described (1). Briefly, the denatured products were dialyzed against 2.33 M urea, 100 mM Tris-HCl, pH 8.0 at 4° C. (140 min), followed by 1.55 M urea, 100 mM Tris-HCl, pH 8.0 (140 min), and 1 M urea, 100 mM Tris-HCl, pH 8 (140 min). Finally the products were dialyzed against 100 mM Tris-HCl, pH 8.0 (48 h). The products were centrifuged at 13000×g (10 min, 4° C.) and concentrated by ultra-filtration through a 10 KDa cut-off filter. All solutions used in the purification and refolding steps were prepared with sterile and endotoxin-free water (S.A.L.F. Laboratorio Farmacologico SpA, Bergamo, Italy). Protein concentration was measured using the BCA Protein Assay Reagent (Pierce, Rockford, Ill.). Protein purity and identity were checked by SDS-PAGE, electrospray mass spectrometry (ESI-MS) and analytical gel-filtration chromatography. The results confirmed the identity of the product (data not shown). The in vitro cytolytic activity of DGR-TNF ($2.5 \times 10^8$ U/mg) was measured by standard cytolytic assay with L-M mouse fibroblasts.

RP-HPLC of DGR-TNF showed that its retention time was similar to that of F2 obtained from NGR-TNF (FIG. 13).

TABLE 1

Molecular mass, cytolytic activity and isoAsp content of F2 and F4.

| Sample | Molecular mass (Da) [a] | Cytolytic Activity (U/mg) [b] | isoAsp (%) [c] |
|---|---|---|---|
| NGR-TNF | — | $2.9 \times 10^8$ | 29.8 |
| F2 | 17844.5 | $(3.5 \pm 0.6) \times 10^8$ | 75 |
| F4 | 17843.5 | $(2.9 \pm 0.7) \times 10^8$ | 14 |
| TNF | — | $8 \times 10^8$ | 2.6 |

[a] By electrospray mass-spectrometry
[b] By cytolytic assay using L-M murine fibroblasts (1).
[c] Isoaspartyl residues were quantified by enzymatic assay (ISOQUANT, protein deamidation detection kit, Promega) and expressed as pmol of isoAsp/pmol of peptide (%).

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

REFERENCES

Aswad, D. W. (1984). Stoichiometric methylation of porcine adrenocorticotropin by protein carboxyl methyltransferase requires deamidation of asparagine 25. Evidence for methylation at the alpha-carboxyl group of atypical L-isoaspartyl residues. J Biol Chem 259, 10714-10721.

Blood et al., (1990) Bioch. Biophys. Acta, 1032:89-118.

Boehm, U., T. Klamp, M. Groot, and J. C. Howard. (1997) Cellular responses to interferon-gamma. *Annu. Rev. Immunol.* 15:749-795

Borgia and Fields, (2000) TibTech 18: 243-251

Brooks, P. C., Montgomery, A. M., Rosenfeld, M., Reisfeld, R. A., Hu, T., Klier, G., and Cheresh, D. A. (1994). Integrin alpha v beta 3 antagonists promote tumor regression by inducing apoptosis of angiogenic blood vessels. Cell 79, 1157-1164.

Brooks, P. C., Stromblad, S., Klemke, R., Visscher, D., Sarkar, F. H., and Cheresh, D. A. (1995). Antiintegrin alpha v beta 3 blocks human breast cancer growth and angiogenesis in human skin. J Clin Invest 96, 1815-1822.

Busk, M., Pytela, R., and Sheppard, D. (1992). Characterization of the integrin alpha v beta 6 as a fibronectin-binding protein. J Biol Chem 267, 5790-5796.

Carswell, E. A., et al., (1975) An endotoxin-induced serum factor that causes necrosis of tumors. Proc. Natl. Acad. Sci. USA. 72:3666-70.

Colombo, G., Curnis, F., De Mori, G. M., Gasparri, A., Longoni, C., Sacchi, A., Longhi, R., and Corti, A. (2002). Structure-activity relationships of linear and cyclic peptides containing the NGR tumor-homing motif. Journal of Biological Chemistry 277, 47891-47897.

Colombo, P., et al., (1993) Immunoscintigraphy with anti-chromogranin A antibodies in patients with endocrine/neuroendocrine tumors. J. Endocr. Invest. 16:841-3.

Corti, A., Poiesi, C., Merli, S., and Cassani, G. (1994). Tumor necrosis factor (TNF) alpha quantification by ELISA and bioassay: effects of TNF alpha-soluble TNF receptor (p55) complex dissociation during assay incubations. Journal of Immunological Methods 177, 191-198.

Corti, A., et al., (1998) Tumor targeting with biotinylated tumor necrosis factor alpha: Structure activity relationships and mechanism of action on avidin pretargeted tumor cells. Cancer Res. 58:3866-3872.

Curnis, F., Gasparri, A., Sacchi, A., Cattaneo, A., Magni, F., and Corti, A. (2005). Targeted delivery of IFNgamma to tumor vessels uncouples antitumor from counterregulatory mechanisms. Cancer Res 65, 2906-2913.

Curnis, F., Sacchi, A., Borgna, L., Magni, F., Gasparri, A., and Corti, A. (2000). Enhancement of tumor necrosis factor alpha antitumor immunotherapeutic properties by targeted delivery to aminopeptidase N (CD13). Nature Biotechnology 18, 1185-1190.

Debs, R. J., et al., (1989) Liposome-associated tumor necrosis factor retains bioactivity in the presence of neutralizing anti-tumor necrosis factor antibodies. J. Immunol. 143: 1192-7.

Debs, R. J., et al., Immunomodulatory and toxic effects of free and liposome-encapsulated tumor necrosis factor alpha in rats. Cancer Res. 1990. 50:375-80.

Dedhar, S., and Gray, V. (1990). Isolation of a novel integrin receptor mediating Arg-Gly-Asp-directed cell adhesion to fibronectin and type I collagen from human neuroblastoma cells. Association of a novel beta 1-related subunit with alpha v. J Cell Biol 110, 2185-2193.

Devos et al., (1982) Nucleic Acids Res. 10:2487-2501.

Di Matteo, P., Curnis, F., Longhi, R., Colombo, G., Sacchi, A., Crippa, L., Protti, M. P., Ponzoni, M., Toma, S., and A., C. Immunogenic and structural properties of the Asn-Gly-Arg (NGR) tumor neovasculature-homing motif. Molecular Immunology (in press).

Ealick et al., (1991) Science 252:698-702.

Eggermont, A. M., et al., (1996) Isolated limb perfusion with tumor necrosis factor and melphalan for limb salvage in 186 patients with locally advanced soft tissue extremity sarcomas. The cumulative multicenter European experience. Ann. Surg. 224:756-65.

Farrar, M. A., and R. D. Schreiber. (1993). The molecular cell biology of interferon-gamma and its receptor. *Annu. Rev. Immunol.* 11:571-611;

Fraker, D. L., Alexander, H. R. & Pass, H. I., (1995). Biologic therapy with TNF: systemic administration and isolation-perfusion. In *Biologic therapy of cancer: principles and practice*, De Vita, V., Hellman, S. & Rosenberg, S. (eds) pp. 329-345. J.B. Lippincott Company: Philadelphia.

Fiers, W. Biologic therapy with TNF: preclinical studies. In V. De Vita, S. Hellman, and S. Rosenberg Eds. Biologic therapy of cancer: principles and practice. J.B. Lippincott Company, Philadelphia, 1995. P. 295-327.

Friedlander, M., Brooks, P. C., Shaffer, R. W., Kincaid, C. M., Varner, J. A., and Cheresh, D. A. (1995). Definition of two angiogenic pathways by distinct alpha v integrins. Science 270, 1500-1502.

Friedlander, M., Theesfeld, C. L., Sugita, M., Fruttiger, M., Thomas, M. A., Chang, S., and Cheresh, D. A. (1996). Involvement of integrins alpha v beta 3 and alpha v beta 5 in ocular neovascular diseases. Proc Natl Acad Sci USA 93, 9764-9769.

Galletti, P., Ingrosso, D., Manna, C., Sica, F., Capasso, S., Pucci, P., and Marino, G. (1988). Enzymatic methyl esterification of synthetic tripeptides: structural requirements of the peptide substrate. Detection of the reaction products by fast-atom-bombardment mass spectrometry. Eur J Biochem 177, 233-239.

Gardner, J. M., and Hynes, R. O. (1985). Interaction of fibronectin with its receptor on platelets. Cell 42, 439-448.

Gasparri, A., Moro, M., Curnis, F., Sacchi, A., Pagano, S., Veglia, F., Casorati, G., Siccardi, A. G., Dellabona, P., and Corti, A. (1999). Tumor pretargeting with avidin improves the therapeutic index of biotinylated tumor necrosis factor alpha in mouse models. Cancer Research 59, 2917-2923.

Gately et al. (1998) Ann. Rev. Immunol. 16:495-521

Geiger, T., and Clarke, S. (1987). Deamidation, isomerization, and racemization at asparaginyl and aspartyl residues in peptides. Succinimide-linked reactions that contribute to protein degradation. J Biol Chem 262, 785-794.

Gray et al. Nature 298:859-863, 1982

Hammes, H. P., Brownlee, M., Jonczyk, A., Sutter, A., and Preissner, K. T. (1996). Subcutaneous injection of a cyclic peptide antagonist of vitronectin receptor-type integrins inhibits retinal neovascularization. Nat Med 2, 529-533.

Helson, L., et al., Effect of tumor necrosis factor on cultured human melanoma cells. Nature 1975. 258:731-732.

Hill, S., et al., Low-dose tumour necrosis factor alpha and melphalan in hyperthermic isolated limb perfusion. Br. J. Sugr. 1993. 80:995-7.

Hocking, D. C., Sottile, J., and McKeown-Longo, P. J. (1998). Activation of distinct alpha5beta1-mediated signaling pathways by fibronectin's cell adhesion and matrix assembly domains. J Cell Biol 141, 241-253.

Humphries, M. J., Obara, M., Olden, K., and Yamada, K. M. (1989). Role of fibronectin in adhesion, migration, and metastasis. Cancer Invest 7, 373-393.

Hynes, R. O. (2002). A reevaluation of integrins as regulators of angiogenesis. Nat Med 8, 918-921.

Johansson, S., Svineng, G., Wennerberg, K., Armulik, A., and Lohikangas, L. (1997). Fibronectin-integrin interactions. Front Biosci 2, dl 26-146.

Kobayashi, et al. (1989) J: Exp Med. 170:827-845

Koivunen, E., Gay, D. A., and Ruoslahti, E. (1993). Selection of peptides binding to the alpha 5 beta 1 integrin from phage display library. Journal of Biological Chemistry 268, 20205-20210.

Lanthier, J., and Desrosiers, R. R. (2004). Protein L-isoaspartyl methyltransferase repairs abnormal aspartyl residues accumulated in vivo in type-I collagen and restores cell migration. Exp Cell Res 293, 96-105.

Lienard, D., et al., In transit metastases of malignant melanoma treated by high dose rTNF alpha in combination with interferon-gamma and melphalan in isolation perfusion. World Journal of Surgery 1992. 16:234-40.

Ling, et al (1995) J. Exp Med. 154:116-127

Ljunggren, H. G., and Karre, K. (1985). Host resistance directed selectively against H-2-deficient lymphoma variants. Analysis of the mechanism. Journal of Experimental Medicine 162, 1745-1759.

Loetscher, H., et al., Human tumor necrosis factor alpha (TNF alpha) mutants with exclusive specificity for the 55-kDa or 75 kDa TNF receptors. J. Biol. Chem. 1993. 268:26350-7.

Lowenson, J. D., and Clarke, S. (1992). Recognition of D-aspartyl residues in polypeptides by the erythrocyte L-isoaspartyl/D-aspartyl protein methyltransferase. Implications for the repair hypothesis. J Biol Chem 267, 5985-5995.

McFadden, P. N., and Clarke, S. (1987). Conversion of isoaspartyl peptides to normal peptides: implications for the cellular repair of damaged proteins. Proc Natl Acad Sci USA 84, 2595-2599.

Modorati, G., et al., Immunoscintigraphy with three step monoclonal pretargeting technique in diagnosis of uveal melanoma: preliminary results. Br. J. Ophtalm. 1994. 78:19-23.

Mohri, H. (1997). Interaction of fibronectin with integrin receptors: evidence by use of synthetic peptides. Peptides 18, 899-907.

Moro, M., et al., Tumor cell targeting with antibody-avidin complexes and biotinylated tumor necrosis factor alpha. Cancer Res. 1997.57:1922-8.

Moyano, J. V., Carnemolla, B., Dominguez-Jimenez, C., Garcia-Gila, M., Albar, J. P., Sanchez-Aparicio, P., Leprini, A., Querze, G., Zardi, L., and Garcia-Pardo, A. (1997). Fibronectin type III5 repeat contains a novel cell adhesion sequence, KLDAPT, which binds activated alpha4beta1 and alpha4beta7 integrins. J Biol Chem 272, 24832-24836.

Murray, E. D., Jr., and Clarke, S. (1984). Synthetic peptide substrates for the erythrocyte protein carboxyl methyltransferase. Detection of a new site of methylation at isomerized L-aspartyl residues. J Biol Chem 259, 10722-10732.

Pankov, R., and Yamada, K. M. (2002). Fibronectin at a glance. J Cell Sci 115, 3861-3863.

Paganelli, G., et al., Clinical application of the avidin-biotin system for tumor targeting. In D. Goldenberg Ed. Cancer therapy with radiolabeled antibodies. CRC Press, Boca Raton, 1995. P. 239-253.

Pennica, D., et al., (1984). Human tumor necrosis factor: precursor, structure, expression and homology to lymphotoxin. *Nature,* 321, 724-729.

Plow, E. F., Haas, T. A., Zhang, L., Loftus, J., and Smith, J. W. (2000). Ligand binding to integrins. J Biol Chem 275, 21785-21788.

Plow, E. F., McEver, R. P., Coller, B. S., Woods, V. L., Jr., Marguerie, G. A., and Ginsberg, M. H. (1985). Related binding mechanisms for fibrinogen, fibronectin, von Willebrand factor, and thrombospondin on thrombin-stimulated human platelets. Blood 66, 724-727.

Podlaski, et al. (1992) Arch. Biochem. Biophys. 294:230-237

Pytela, R., Pierschbacher, M. D., and Ruoslahti, E. (1985). Identification and isolation of a 140 kd cell surface glycoprotein with properties expected of a fibronectin receptor. Cell 40, 191-198.

Rathjen, D. A., et al., (1992). Selective enhancement of the tumour necrotic activity of TNF alpha with monoclonal antibody. Brit. J. Cancer 65:852.

Reissner, K. J., and Aswad, D. W. (2003). Deamidation and isoaspartate formation in proteins: unwanted alterations or surreptitious signals? Cell Mol Life Sci 60, 1281-1295.

Rinderknecht et al. (J. Biol. Chem. 259:6790-6797, 1984

Robert, B., et al., 1996. Cytokine targeting in tumors using a bispecific antibody directed against carcinoembryonic antigen and tumor necrosis factor alpha. Cancer Res. 56:4758.

Robinson, A. B., McKerrow, J. H., and Cary, P. (1970). Controlled deamidation of peptides and proteins: an experimental hazard and a possible biological timer. Proc Natl Acad Sci USA 66, 753-757.

Robinson, N. E., and Robinson, A. B. (2001). Molecular clocks. Proc Natl Acad Sci USA 98, 944-949.

Robinson, N. E., Robinson, Z. W., Robinson, B. R., Robinson, A. L., Robinson, J. A., Robinson, M. L., and Robinson, A. B. (2004). Structure-dependent nonenzymatic deamidation of glutaminyl and asparaginyl pentapeptides. J Pept Res 63, 426-436.

Schraffordt Koops, et al., (1998) Hyperthermic isolated limb perfusion with tumour necrosis factor and melphalan as treatment of locally advanced or recurrent soft tissue sarcomas of the extremities. Radiothepray & Oncology. 48:1-4.

Seder, et al. (1993) Proc. Natl. Acad. Sci. 90:10188-10192

Smith, J. W., Vestal, D. J., Irwin, S. V., Burke, T. A., and Cheresh, D. A. (1990). Purification and functional characterization of integrin alpha v beta 5. An adhesion receptor for vitronectin. J Biol Chem 265, 11008-11013.

Stephenson, R. C., and Clarke, S. (1989). Succinimide formation from aspartyl and asparaginyl peptides as a model for the spontaneous degradation of proteins. J Biol Chem 264, 6164-6170.

Takada, Y., Huang, C., and Hemler, M. E. (1987). Fibronectin receptor structures in the VLA family of heterodimers. Nature 326, 607-609.

Tanzarella, S., Russo, V., Lionello, I., Dalerba, P., Rigatti, D., Bordignon, C., and Traversari, C. (1999). Identification of a promiscuous T-cell epitope encoded by multiple members of the MAGE family. Cancer Res 59, 2668-2674.

Taya et al., (1982) EMBO J. 1:953-958.

Tracey, K. J., and A. Cerami. (1993) Tumor necrosis factor, other cytokines and disease. Ann. Rev. Cell Biol, 9:317-43.

Tyler-Cross, R., and Schirch, V. (1991). Effects of amino acid sequence, buffers, and ionic strength on the rate and mechanism of deamidation of asparagine residues in small peptides. J Biol Chem 266, 22549-22556.

Van Ostade, X., et al., (1993) Human TNF mutants with selective activity on the p55 receptor. Nature. 361:266-9.

Vogel, B. E., Tarone, G., Giancotti, F. G., Gailit, J., and Ruoslahti, E. (1990). A novel fibronectin receptor with an unexpected subunit composition (alpha v beta 1). J Biol Chem 265, 5934-5937.

Weber, D. J., and McFadden, P. N. (1997b). Injury-induced enzymatic methylation of aging collagen in the extracellular matrix of blood vessels. J Protein Chem 16, 269-281.

Weinacker, A., Chen, A., Agrez, M., Cone, R. I., Nishimura, S., Wayner, E., Pytela, R., and Sheppard, D. (1994). Role of the integrin alpha v beta 6 in cell attachment to fibronectin. Heterologous expression of intact and secreted forms of the receptor. J Biol Chem 269, 6940-6948.

Wood and Wetzel, (1992), Int'l J. Peptide Protein Res. 39: 533-39

Yamada, K. M. (1989). Fibronectins: structure, functions and receptors. Curr Opin Cell Biol 1, 956-963.

Yang, J., et al., (1995) A genetically engineered single-chain FV/TNF molecule possesses the anti-tumor immunoreactivity of FV as well as the cytotoxic activity of tumor necrosis factor. Mol. Immunol. 32:873-81.

The invention claimed is:

1. An isolated peptide comprising an isoDGR motif, wherein the peptide selectively inhibits αvβ3 integrin.

2. A peptide according to claim 1 comprising the sequence XisoDGRX' (SEQ ID NO: 54) wherein:
(a) X is selected form the group consisting of L, V, A, C, G, Y, P, H, K, Q and I; and
(b) X' is selected from the group consisting of C, G, H, L, E, T, Q, R, S and P.

3. A peptide according to claim 1, wherein the peptide comprises a sequence selected from the group consisting of CisoDGRCVSGCAGRC (SEQ ID NO: 55), isoDGRAHA (SEQ ID NO: 56), GisoDGRG (SEQ ID NO: 57), CVLiso DGRMEC (SEQ ID NO: 58), CisoDGRC (SEQ ID NO: 59), CisoDGRCG (SEQ ID NO: 60), LisoDGRE (SEQ ID NO: 61), YisoDGRT (SEQ ID NO: 62), LQCICTGiso DGRGEWKCE (SEQ ID NO: 63), LQCISTGiso DGRGEWKCE (SEQ ID NO: 64), CICTGisoDGRGEWKC (SEQ ID NO: 65), CISTGisoDGRGEWKC (SEQ ID NO: 66), MRCTCVGisoDGRGEWTCY (SEQ ID NO: 67), MRCTSVGisoDGRGEWTCY (SEQ ID NO: 68), CTCVGisoDGRGEWTC (SEQ ID NO: 69) and CTSVGiso DGRGEWTC (SEQ ID NO: 70).

4. A peptide according to claim 3, wherein the peptide comprises cycloCVLisoDGRMEC (SEQ ID NO: 58), linear CisoDGRC (SEQ ID NO: 59), cyclic CisoDGRC (SEQ ID NO: 59), linear CisoDGRCG (SEQ ID NO: 60) or cyclic CisoDGRCG (SEQ ID NO: 60).

5. A peptide according to claim 1, wherein isoDGR is $_L$isoDGR.

6. A peptide according to claim 1, wherein the peptide comprises a deamidation product of an extracellular matrix protein or of a fragment or derivative thereof.

7. A peptide according to claim 6, wherein the peptide comprises a deamidation product of fibronectin, vitronectin, collagen, laminin, or of a fragment or derivative thereof.

8. A peptide according to claim 7, wherein the peptide comprises a deamidation product of the FN-I$_5$, FN-I$_7$, FN-II$_1$ or FN-III$_9$ module of fibronectin or of a fragment or derivative thereof.

9. A peptide according to claim 1, wherein the peptide inhibits tumor growth.

10. A peptide according to claim 1, wherein the peptide inhibits angiogenisis.

11. A peptide according to claim 1, wherein the peptide does not comprise an additional therapeutic agent.

12. A peptide according to claim 11, wherein the additional therapeutic agent is an anti-cancer peptide.

13. A peptide according to claim 11, wherein the additional therapeutic agent is a cytokine.

14. A peptide according to claim 1, wherein the peptide comprises a turn involving the G and R residues of the DGR motif.

15. A peptide according to claim 1, wherein the peptide comprises up to 350 amino acids.

16. A conjugation product comprising a peptide as defined in claim 1, and a drug, cytokine, cytokine fragment, toxin, apoptotic peptide, biological response modifier, radionuclide, viral particle, gene or an imaging compound.

17. A pharmaceutical composition comprising an effective amount of a peptide as defined in claim 1.

18. A composition according to claim 17 together with a pharmaceutically acceptable carrier, diluent or excipient.

19. A composition according to claim 17 comprising essentially no peptide having a corresponding NGR motif.

20. A conjugation product between a peptide as defined claim 1 and a cytokine.

21. A conjugation product between a cytokine and a targeting moiety comprising the DGR motif.

22. A conjugation product according to claim 21 wherein the DGR is isoDGR.

23. A conjugation product according to claim 16 wherein the DGR is $_L$isoDGR.

24. A conjugation product according to claim 20, wherein the cytokine is derivatized with polyethylene glycol or an acyl residue.

25. A conjugation product according to claim 20, wherein the cytokine is further conjugated with a compound selected from the group consisting of an antibody, an antibody fragment, and biotin, wherein said antibody or fragment thereof is directed to a compound selected from the group consisting of a tumoral antigen, a tumoral angiogenic marker, and a component of the extracellular matrix.

26. A conjugation product according to claim 25, wherein the cytokine is TNF and is conjugated to both the targeting moiety and a compound selected from the group consisting of an antibody, and antibody fragment, and biotin.

27. A conjugation product according to claim 20, other than when formed in vivo by metabolism of a peptide comprising the NGR motif.

28. A conjugation product according to claim 20, wherein the cytokine is linked to the peptide or targeting moiety through a spacer.

29. A conjugation product according to claim 28 wherein the spacer is a glycine (D).

30. A conjugation product according to claim 20, wherein the cytokine is selected from the group consisting of TNF, IFNγ, IL-12, IP-10, IL-7 and EMAP II.

31. A conjugation product according to claim 20, wherein the cytokine is TNF or IFNγ.

32. A conjugation product according to claim 31, wherein the cytokine is TNF.

33. A conjugation product according to claim 32, wherein the cytokine is TNFα or TNFβ.

34. A pharmaceutical composition comprising an effective amount of a conjugation product as claimed in claim 20, together with a pharmaceutically acceptable carrier, diluent or excipient.

35. A pharmaceutical composition comprising an effective amount of a conjugation product of TNF and a peptide as defined in any claim 1, and an effective amount of IFNγ.

36. A pharmaceutical composition comprising an effective amount of a conjugation product of claim 32 and an effective amount of IFNγ or a polynucleotide encoding therefor.

37. A composition according to claim 17, in the form of an injectable solution or suspension or a liquid for infusions.

38. A composition according to claim 17, in the form of liposomes.

39. A composition according to claim 17, further comprising another antitumor agent or a diagnostic tumor-imaging compound.

40. A composition according to claim 39, wherein the other antitumor agent is doxorubicin, melphalan, cis-platin, gemcitabine or taxol.

* * * * *